US005428145A

United States Patent [19]

Okamoto et al.

[11] Patent Number: 5,428,145
[45] Date of Patent: Jun. 27, 1995

[54] NON-A, NON-B, HEPATITIS VIRUS GENOME, POLYNUCLEOTIDES, POLYPEPTIDES, ANTIGEN, ANTIBODY AND DETECTION SYSTEMS

[75] Inventors: Hiroaki Okamoto, Minami Kawachi; Tetsuo Nakamura, Tokyo, both of Japan

[73] Assignee: Immuno Japan, Inc., Tokyo, Japan

[21] Appl. No.: 925,695

[22] Filed: Aug. 7, 1992

Related U.S. Application Data

[63] Continuation-in-part of Ser. No. 866,045, Apr. 9, 1992, abandoned.

[30] Foreign Application Priority Data

Aug. 9, 1991 [JP] Japan ............................ 3-287402
Dec. 5, 1991 [JP] Japan ............................ 3-360441

[51] Int. Cl.$^6$ .................... A61K 39/29; C12N 15/51
[52] U.S. Cl. ........................... 536/23.72; 536/23.1; 424/185.1; 424/186.1; 424/189.1; 424/228.1; 424/225.1; 435/69.3; 435/172.3; 530/350; 530/826
[58] Field of Search .................... 435/69.3, 172.3; 536/27, 23.72, 23.1; 424/185.1, 186.1, 189.1, 228.1, 225.1; 530/350, 826

[56] References Cited

FOREIGN PATENT DOCUMENTS

| | | |
|---|---|---|
| 0414475 | 2/1991 | European Pat. Off. . |
| 0516859 | 11/1991 | European Pat. Off. . |
| 0468657 | 1/1992 | European Pat. Off. . |
| 0485209 | 5/1992 | European Pat. Off. . |
| WO91/14779 | 3/1991 | WIPO . |
| WO92/19743 | 5/1992 | WIPO . |

OTHER PUBLICATIONS

Enomoto, N., et al., "There Are Two Major Types of Hepatitis C Virus in Japan", Biochemical and Biophysical Research Communications (1990), vol. 170, pp. 1021–1025.
Bauie, J. U et al. Science 247:1306–1310 (1990).
Kumar, V. et al. Proc. Natl. Acad. Sci. 87:1337–1341 (1990).
Enomoto et al. 1990 "There are two major types of hepatitis C virus in Japan" Biochem. Biophys. Res. Comm. 170(3):1021–25.
Kato, N. et al. 1990 "Molecular Cloning of the human hepatitis C virus opniome from Japanese patents with non-A, non-B hepatitis." Proc. Natl. Acad Sci. 87:9524–9528.
Okamoto et al. 1991 "Nucleotide sequence of the genomic RNA of hepatitis C virus isolated from a human carrier: comparison with reported isolates for conserved and divergent regions." J. Gen Virol. 72: 2697–2704.
Okamoto et al, 1992 "Full-length sequence of a hepatitis C Virus genome having poor homology to reported isolates: Comparative study of from distinct genotypes" Virol. 188: 331–341.

Primary Examiner—Hazel F. Sidberry
Assistant Examiner—Michael S. Tuscan
Attorney, Agent, or Firm—Beveridge, DeGrandi, Weilacher & Young

[57] ABSTRACT

Non-A, non-B hepatitis (NANB hepatitis) virus RNA and its corresponding polypeptide, related antigen, antibody, and detection systems for detecting NANB hepatitis antigen or antibodies.

6 Claims, 6 Drawing Sheets

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
( A ) LENGTH: 9589 base pairs (B) TYPE: nucleic acid
(C) STRANDEDNESS: single
(D) TOPOLOGY: linear (xi) SEQUENCE DESCRIPTION: SEQ ID NO:1:

| | | | | | | |
|---|---|---|---|---|---|---|
| ACCCGCCCCU | AAUAGGGGCG | ACACUCCGCC | AUGAACCACU | CCCCUGUGAG | GAACUACUGU | 60 |
| CUUCACGCAG | AAAGCGUCUA | GCCAUGGCGU | UAGUAUGAGU | GUCGUACAGC | CUCCAGGCCC | 120 |
| CCCCCUCCCG | GGAGAGCCAU | AGUGGUCUGC | GGAACCGGUG | AGUACACCGG | AAUUGCCGGG | 180 |
| AAGACUGGGU | CCUUUCUUGG | AUAAACCCAC | UCUAUGCCCG | GUCAUUGGG | CGUGCCCCG | 240 |
| CAAGACUGCU | AGCCGAGUAG | CGUUGGGUUG | CGAAAGGCCU | UGUGGUACUG | CCUGAUAGGG | 300 |
| UGCUUGCGAG | UGCCCCGGGA | GGUCUCGUAG | ACCGUGCACC | AUGAGCACAA | AUCCUAAACC | 360 |
| UCAAAGAAAA | ACCAAAAGAA | ACACCAACCG | UCGCCCACAA | GACGUUAAGU | UCCGGGCGG | 420 |
| CGGCCAGAUC | GUUGGCGGAG | UAUACUUGUU | GCCGCGCAGG | GGCCCCAGGU | UGGGUGUGCG | 480 |
| CGCGACAAGG | AAGACUUCGG | AGCGGUCCCA | GCCACGUGGA | AGGCGCCAGC | CCAUCCCUAA | 540 |
| GGAUCGGCGC | UCCACUGGCA | AAUCCUGGGG | AAAACCAGGA | UACCCCUGGC | CCCUAUACGG | 600 |
| GAAUGAGGGA | CUCGGCUGGG | CAGGAUGGCU | CCUGUCCCCC | CGAGGUUCCC | GUCCCUCUUG | 660 |
| GGGCCCCAAU | GACCCCCGGC | AUAGGUCCCG | CAACGUGGGU | AAGGUCAUCG | AUACCCUAAC | 720 |
| GUGCGGCUUU | GCCGACCUCA | UGGGGUACAU | CCCUGUCGUA | GGCGCCCCGC | UCGGCGGCGU | 780 |
| CGCCAGAGCU | CUCGCGCAUG | GCGUGAGAGU | CCUGGAGGAC | GGGGUUAAUU | UUGCAACAGG | 840 |
| GAACUUACCC | GGUUGCUCCU | UUUCUAUCUU | CUUGCUGGCC | CUGCUGUCCU | GCAUCACCAC | 900 |
| CCCGGUCUCC | GCUGCCGAAG | UGAAGAACAU | CAGUACCGGC | UACAUGGUGA | CCAACGACUG | 960 |
| CACCAAUGAU | AGCAUUACCU | GGCAACUCCA | GGCUGCUGUC | CUCCACGUCC | CCGGGUGCGU | 1020 |
| CCCGUGCGAG | AAAGUGGGGA | AUACAUCUCG | GUGCUGGAUA | CCGGUCUCAC | CGAAUGUGGC | 1080 |
| CGUGCAGCAG | CCCGGCGCCC | UCACGCAGGG | CUUACGGACG | CACAUUGACA | UGGUUGUGAU | 1140 |
| GUCCGCCACG | CUCUGCUCCG | CUCUUUACGU | GGGGGACCUC | UGCGGUGGGG | UGAUGCUUGC | 1200 |
| AGCCCAGAUG | UUCAUUGUCU | CGCCACAGCA | CCACUGGUUU | GUGCAAGACU | GCAAUUGCUC | 1260 |
| CAUCUACCCU | GGUACCAUCA | CUGGACACCG | CAUGGCGUGG | GACAUGAUGA | UGAACUGGUC | 1320 |
| GCCCACGGCU | ACCAUGAUCC | UGGCGUACGC | GAUGCGCGUC | CCCGAGGUCA | UCAUAGACAU | 1380 |
| CAUUGGCGGG | GCUCAUUGGG | GCGUCAUGUU | CGGCUUAGCC | UACUUCUCUA | UGCAGGGAGC | 1440 |
| GUGGGCAAAA | GUCGUUGUCA | UUCUUUUGCU | GGCCGCCGGG | GUGGACGCGC | AAACCCAUAC | 1500 |
| CGUUGGGGGU | UCUACCGCGC | AUAACGCCAG | GACCCUCACC | GGCAUGUUCU | CCCUUGGUGC | 1560 |
| CAGGCAGAAA | AUCCAGCUCA | UCAACACCAA | UGGCAGUUGG | CACAUCAACC | GCACCGCCCU | 1620 |
| GAACUGCAAU | GACUCUUUGC | ACACCGGCUU | CCUCGCGUCA | CUGUUCUACA | CCCACAGCUU | 1680 |
| CAACUCGUCA | GGAUGUCCCG | AACGCAUGUC | CGCCUGCCGC | AGUAUCGAGG | CCUUUCGGGU | 1740 |
| GGGAUGGGGC | GCCUUACAAU | AUGAGGACAA | UGUCACCAAU | CCAGAGGAUA | UGAGACCGUA | 1800 |
| UUGCUGGCAC | UACCCACCAA | GACAGUGUGG | UGUAGUCUCC | GCGAGCUCUG | UGUGGGCCC | 1860 |
| AGUGUACUGU | UUCACCCCCA | GCCCAGUAGU | AGUGGGUACG | ACCGAUAGAC | UUGGAGCGCC | 1920 |
| CACUUACACG | UGGGGGGAGA | AUGAGACAGA | UGUCUUCCUA | UUGAACAGCA | CUCGACCACC | 1980 |
| GCAGGGGUCA | UGGUUCGGCU | GCACGUGGAU | GAACUCCACU | GGCUACACCA | AGACUUGCGG | 2040 |
| CGCACCACCC | UGCCGCAUUA | GAGCUGACUU | CAAUGCCAGC | AUGGACUUGU | UGUGCCCCAC | 2100 |
| GGACUGUUUU | AGGAAGCAUC | CUGAUACCAC | CUACAUCAAA | UGUGGCUCUG | GCCCUGGCU | 2160 |
| CACGCCAAGG | UGCCUGAUCG | ACUACCCCUA | CAGGCUCUGG | CAUUACCCCU | GCACAGUUAA | 2220 |
| CUAUACCAUC | UUCAAAAUAA | GGAUGUAUGU | GGGGGGGUC | GAGCACAGGC | UCACGGCUGC | 2280 |

```
GUGCAAUUUC ACUCGUGGGG AUCGUUGCAA CUUGGAGGAC AGAGACAGAA GUCAACUGUC    2340
UCCUUUGCUG CACUCCACCA CGGAGUGGGC CAUUUUACCU UGCACUUACU CGGACCUGCC    2400
CGCCUUGUCG ACUGGUCUUC UCCACCUCCA CCAAAACAUC GUGGACGUGC AAUUCAUGUA    2460
UGGCCUAUCA CCUGCUCUCA CAAAAUACAU CGUCCGAUGG GAGUGGGUAG UACUCUUAUU    2520
CCUGCUCUUA GCGGACGCCA GGGUUUGCGC CUGCUUAUGG AUGCUCAUCU UGUUGGGCCA    2580
GGCCGAAGCA GCACUAGAGA AGUUGGUCGU CUUGCACGCU GCGAGCGCAG CUAGCUGCAA    2640
UGGCUUCCUA UACUUGUCA UCUUUUCGU GGCUGCUUGG UACAUCAAGG GUCGGGUAGU      2700
CCCCUUGGCU ACUUAUCCC UCACUGGCCU AUGGUCCUUU GGCCUACGC UCCUAGCAUU      2760
GCCCCAACAG GCUUAUGCUU AUGACGCAUC UGUACAUGGU CAGAUAGGAG CAGCUCUGUU    2820
GGUACUGAUC ACUCUCUUUA CACUCACCCC CGGGUAUAAG ACCCUUCUCA GCCGGUUUCU    2880
GUGGUGGUUG UGCUAUCUUC UGACCCUGGC GGAAGCUAUG GUCCAGGAGU GGGCACCACC    2940
UAUGCAGGUG CGCGGUGGCC GUGAUGGGAU CAUAUGGGCC GUCGCCAUAU CUGCCCGGG     3000
UGUGGUGUUU GACAUAACCA AGUGGCUCUU GGCGGUGCUU GGGCCUGCUU AUCUCCUAAA    3060
AGGUGCUUUG ACGCGUGUGC CGUACUUCGU CAGGGCUCAC GCUCUACUAA GGAUGUGCAC    3120
CAUGGUAAGG CAUCUCGCGG GGGUAGGUA CGUCCAGAUG GUGCUACUAG CCCUUGGCAG     3180
GUGGACUGGC ACUUACAUCU AUGACCACCU CACCCCUAUG UCGGAUUGGG CUGCUAAUGG    3240
CCUGCGGGAC UUGGCGGUCG CCGUGGAGCC UAUCAUCUUC AGUCCGAUGG AGAAAAAAGU    3300
CAUCGUCUGG GGAGCGGAGA CAGCUGCUUG CGGGGAUAUC UUACACGGAC UUCCCGUGUC    3360
CGCCCGACUU GGCCGGGAGG UCCUCCUUGG CCCAGCUGAU GGCUAUACCU CCAAGGGGUG    3420
GAGUCUUCUC GCCCCCAUCA CUGCUUAUGC CCAGCAGACA CGCGGCCUUU UGGGCACCAU    3480
AGUGGUGAGC AUGACGGGGC GCGACAAGAC AGAACAGGCC GGGGAGAUUC AGGUCCUGUC    3540
CACGGUCACU CAGUCCUUCC UCGGAACAAC CAUCUCGGGG GUCUUAUGGA CUGUCUACCA    3600
UGGAGCUGGC AACAAGACUC UAGCCGGCUC ACGGGGUCCG GUCACACAGA UGUACUCCAG    3660
UGCUGAGGGG GACUUAGUGG GGUGGCCCAG CCCCCCCGGG ACCAAAUCUU GGAGCCGUG     3720
CACGUGUGGA GCGGUCGACC UAUACCGGGU CACGCGAAAC GCUGAUGUCA UCCCGGCUCG    3780
AAGACGCGGG GACAAGCGAG GAGCGCUACU CUCCCCGAGA CCUCUUUCCA CCUUGAAGGG    3840
GUCCUCGGGG GGCCCGGUGC UCUGCCCCAG AGGCCACGCU GUCGGGGUCU UCCGGGCAGC    3900
CGUGUGCUCC CGGGGCGUGG CCAAGUCCAU AGAUUUUAUC CCCGUUGAGA CACUUGACAU    3960
CGUCACUCGG UCCCCACCU UUAGUGACAA CAGCACACCA CCUGCUGUGC CCCAAACUUA     4020
UCAGGUCGGG UACUUACAUG CCCCGACUGG UAGUGGAAAG AGCACCAAAG UCCCUGUCGC    4080
GUAUGCCGCU CAGGGGUACA AAGUGCUAGU GCUUAAUCCC UCGGUGGCUG CCACCCUGGG    4140
GUUUGGGGCG UACUUGUCCA AGGCACAUGG CAUCAAUCCC AACAUUAGGA CUGGGGUCAG    4200
GACUGUGACG ACCGGGGCGC CAUCACGUA CUCCACAUAU GGCAAAUUCC UCGCCGAUGG     4260
GGGCUGCGCA GGCGGCGCCU AUGACAUCAU CAUAUGCGAU GAAUGCCAUG CCGUGGACUC    4320
UACCACCAUU CUCGGCAUCG GAACAGUCCU CGAUCAAGCA GAGACAGCCG GGUCAGGCU     4380
AACUGUACUG GCUACGGCUA CGCCCCCCGG GUCAGUGACA ACCCCCCACC CCAACAUAGA    4440
GGAGGUGGCC CUCGGGCAGG AGGGUGAGAU CCCUUCUAU GGGAGGGCGA UUCCCCUGUC     4500
AUACAUCAAG GGAGGAAGAC ACUUGAUCUU CUGCCACUCA AAGAAAAGU GUGACGAGCU     4560
CGCGGCGGCC CUUCGGGUA UGGGCUUGAA CGCAGUGGCA UACUACAGAG GCUGGACGU     4620
CUCCGUAAUA CCAACUCAGG GAGACGUAGU GGUCGUCGCC ACCGACGCCC UCAUGACGGG    4680
GUUUACUGGA GACUUUGACU CCGUGAUCGA CUGCAACGUA GCGGUCACUC AAGUUGAGA     4740
```

| | | | | | | |
|---|---|---|---|---|---|---|
| CUUCAGCUUG | GACCCCACAU | UCACCAUAAC | CACACAGACU | GUCCCUCAAG | ACGCUGUCUC | 4800 |
| ACGUAGCCAG | CGCCGGGGCC | GCACGGGCAG | GGGAAGACUG | GGUAUUUAUA | GGUAUGUUUC | 4860 |
| CACUGGUGAG | CGAGCCUCAG | GAAUGUUUGA | CAGUGUAGUG | CUCUGCGAGU | GCUACGAUGC | 4920 |
| AGGGGCCGCA | UGGUAUGAGC | UCACACCAGC | GGAGACCACC | GUCAGGCUCA | GAGCAUAUUU | 4980 |
| CAACACACCU | GGUUUGCCUG | UGUGCCAAGA | CCAUCUUGAG | UUUGGGAGG | CAGUUUUCAC | 5040 |
| CGGCCUCACA | CACAUAGAUG | CCCACUUCCU | UUCCAAACA | AAGCAAUCGG | GGGAAAAUUU | 5100 |
| CGCAUACUUA | ACAGCCUACC | AGGCUACAGU | GUGCGCUAGG | GCCAAAGCCC | CCCCCCGUC | 5160 |
| CUGGGACGUC | AUGUGGAAGU | GUUGACUCG | ACUCAAGCCC | ACACUCGUGG | GCCCCACACC | 5220 |
| UCUCCUGUAC | CGCUUGGGCU | CUGUUACCAA | CGAGGUCACC | CUCACGCAUC | CUGUGACGAA | 5280 |
| AUACAUCGCC | ACCUGCAUGC | AAGCCGACCU | UGAGGUCAUG | ACCAGCACGU | GGGUCUUAGC | 5340 |
| UGGGGGGGUC | UUGGCGGCCG | UCGCCGCGUA | CUGCCUGGCG | ACCGGGUGUG | UUUGCAUCAU | 5400 |
| CGGCCGCUUG | CACGUUAACC | AGCGAGCCGU | CGUUGCACCG | GACAAGGAGG | UCCUCUAUGA | 5460 |
| GGCUUUUGAU | GAGAUGGAGG | AAUGUGCCUC | UAGAGCGGCU | CUCAUUGAAG | AGGGGCAGCG | 5520 |
| GAUAGCCGAG | AUGCUGAAGU | CCAAGAUCCA | AGGCUUAUUG | CAGCAAGCUU | CCAAACAAGC | 5580 |
| UCAAGACAUA | CAACCCGCUG | UGCAGGCUUC | UUGGCCCAAG | GUAGAGCAAU | UCUGGGCCAA | 5640 |
| ACACAUGUGG | AACUUCAUCA | GCGGCAUUCA | AUACCUCGCA | GGACUAUCAA | CACUGCCAGG | 5700 |
| GAACCCUGCU | GUAGCUUCCA | UGAUGGCAUU | CAGUGCCGCC | CUCACCAGUC | CGUUGUCAAC | 5760 |
| UAGCACCACU | AUCCUUCUCA | ACAUUUGGGG | GGGCUGGCUA | GCAUCCCAAA | UUGCGCCUCC | 5820 |
| CGCGGGGGCU | ACCGGCUUCG | UCGUCAGUGG | CCUGGUGGGG | GCUGCCGUAG | GCAGCAUAGG | 5880 |
| CUUGGGUAAG | GUGCUGGUGG | ACAUCCUGGC | AGGGUAUGGU | GCGGGCAUUU | CGGGGGCUCU | 5940 |
| CGUCGCAUUC | AAGAUCAUGU | CUGGCGAGAA | GCCCUCCAUG | GAGGAUGUUG | UCAACCUGCU | 6000 |
| GCCUGGAAUU | CUGUCUCCGG | GUGCCCUGGU | GGUGGGAGUC | AUCUGCGCGG | CCAUCCUGCG | 6060 |
| CCGACACGUG | GGACCGGGGG | AAGGCGCUGU | CCAAUGGAUG | AAUAGGCUCA | UUGCCUUUGC | 6120 |
| UUCCAGAGGA | AACCACGUCG | CCCCCACCCA | CUACGUGACG | GAGUCGGAUG | CGUCGCAGCG | 6180 |
| UGUGACCCAA | CUACUUGGCU | CCCUUACCAU | AACCAGCCUG | UCAGGAGAC | UCCACAACUG | 6240 |
| GAUUACUGAA | GACUGCCCCA | UCCCAUGCAG | CGGCUCGUGG | CUCCGCGAUG | UGUGGGAUUG | 6300 |
| GGUUUGCACC | AUCCUAACAG | ACUUUAAAAA | CUGGCUGACC | UCCAAAUUGU | CCCAAAGAU | 6360 |
| GCCUGGUCUC | CCCUUUAUCU | CUUGUCAAAA | GGGGUACAAG | GGCGUGUGGG | CUGGCACUGG | 6420 |
| UAUCAUGACC | ACACGGUGUC | CUUGCGGCGC | CAAUAUCUCU | GGCAAUGUCC | GCCUGGGCUC | 6480 |
| CAUGAGAAUU | ACGGGCCCA | AAACCUGCAU | GAAUACUGG | CAGGGGACCU | UUCCCAUCAA | 6540 |
| UUGUUACACG | GAGGGCCAGU | GCGUGCCGAA | ACCCGCACCA | AACUUUAAGA | UCGCCAUCUG | 6600 |
| GAGGGUGGCG | GCCUCAGAGU | ACGCGGAGGU | GACGCAGCAC | GGGUCAUACC | ACUACAUAAC | 6660 |
| AGGACUUACC | ACUGAUAACU | UGAAAGUUCC | UUGCCAACUA | CCUUCUCCAG | AGUUCUUUUC | 6720 |
| CUGGGUGGAC | GGAGUGCAGA | UCCAUAGGUU | UGCCCCCAUA | CCGAAGCCGU | UUUUCGGGA | 6780 |
| UGAGGUCUCG | UUCUGCGUUG | GGCUUAAUUC | AUUUGUCGUC | GGGUCUCAGC | UCCCUUGCGA | 6840 |
| UCCUGAACCU | GACACAGACG | UAUUGACGUC | CAUGCUAACA | GACCCAUCCC | AUAUCACGGC | 6900 |
| GGAGACUGCA | GCGCGGCGUU | UGGCACGGGG | GUCACCCCG | UCCGAGGCAA | GCUCCUCAGC | 6960 |
| GAGCCAGCUA | UCGGCACCAU | CGCUGCGAGC | CACCUGCACC | ACCCACGGCA | AGGCCUAUGA | 7020 |
| UGUGGACAUG | GUGGAUGCCA | ACCUGUUCAU | GGGGGGCGAU | GUGACCCGGA | UAGAGUCUGA | 7080 |
| GUCCAAAGUG | GUCGUUCUGG | ACUCUCUCGA | CCCAAUGGUC | GAAGAAAGGA | GCGACCUUGA | 7140 |
| GCCUUCGAUA | CCAUCGGAAU | AUAUGCUCCC | CAAGAAGAGA | UUCCCACCAG | CCUUACCGGC | 7200 |

-continued

| | | | | | | |
|---|---|---|---|---|---|---|
| UUGGGCACGG | CCUGAUUACA | ACCCACCGCU | UGUGGAAUCG | UGGAAGAGGC | CAGAUUACCA | 7260 |
| ACCGGCCACU | GUUGCGGGCU | GCGCUCUCCC | CCCCCCUAAG | AAAACCCCGA | CGCCUCCCCC | 7320 |
| AAGGAGACGC | CGGACAGUGG | GUCUGAGUGA | GAGCUCCAUA | GCAGAUGCCC | UACAACAGCU | 7380 |
| GGCCAUCAAG | UCCUUUGGCC | AGCCCCCCCC | AAGCGGCGAU | UCAGGCCUUU | CCACGGGGGC | 7440 |
| GGACGCAGCC | GAUUCCGGCA | GUCGGACGCC | CCCCGAUGAG | UUGGCCCUUU | CGGAGACAGG | 7500 |
| UUCCAUCUCC | UCCAUGCCCC | CUCUCGAGGG | GGAGCCUGGA | GAUCCAGACU | GGAGCCUGA | 7560 |
| GCAGGUAGAG | CUUCAACCUC | CCCCCCAGGG | GGGGUGGUA | ACCCCCGGCU | CAGGCUCGGG | 7620 |
| GUCUUGGUCU | ACUUGCUCCG | AGGAGGACGA | CUCCGUCGUG | UGCUGCUCCA | UGUCAUACUC | 7680 |
| CUGGACCGGG | GCUCUAAUAA | CUCCUUGUAG | CCCCGAAGAG | GAAAAGUUGC | CAAUUGGCCC | 7740 |
| CUUGAGCAAC | UCCCUGUUGC | GAUAUCACAA | CAAGGUGUAC | UGUACCACAU | CAAAGAGCGC | 7800 |
| CUCAUUAAGG | GCUAAAAAGG | UAACUUUUGA | UAGGAUGCAA | GCGCUCGACG | CUCAUUAUGA | 7860 |
| CUCAGUCUUG | AAGGACAUUA | AGCUAGCGGC | CUCCAAGGUC | ACCGCAAGGC | UUCUCACUUU | 7920 |
| AGAGGAGGCC | UGCCAGUUAA | CUCCACCCCA | CUCUGCAAGA | UCCAAGUAUG | GGUUUGGGGC | 7980 |
| UAAGGAGGUC | CGCAGCUUGU | CCGGGAGAGC | CGUUAACCAC | AUCAAGUCCG | UGUGGAAGGA | 8040 |
| CCUCCUGGAA | GACACACAAA | CACCAAUUCC | UACAACCAUC | AUGGCCAAAA | AUGAGGUGUU | 8100 |
| CUGCGUGGAC | CCCACCAAGG | GGGUAAGAA | AGCAGCUCGC | CUUAUCGUUU | ACCCUGACCU | 8160 |
| CGGCGUCAGG | GUCUGCGAGA | AAAUGGCCCU | UUAUGAUAUC | ACACAAAAGC | UUCCUCAGGC | 8220 |
| GGUGAUGGGG | GCUUCUUAUG | GAUUCCAGUA | CUCCCCCGCU | CAGCGGGUGG | AGUUUCUCUU | 8280 |
| GAAGGCAUGG | GCGGAAAAGA | AAGACCCUAU | GGGUUUUUCG | UAUGAUACCC | GAUGCUUUGA | 8340 |
| CUCAACCGUC | ACUGAGAGAG | ACAUCAGGAC | UGAGGAGUCC | AUAUAUCGGG | CUUGUUCCUU | 8400 |
| GCCCGAGGAG | GCCCACACUG | CCAUACACUC | ACUGACUGAG | AGACUUUACG | UGGGAGGGCC | 8460 |
| CAUGUUCAAC | AGCAAGGGCC | AGACCUGCGG | GUACAGGCGU | UGCCGCGCCA | GCGGGGUGCU | 8520 |
| UACCACUAGC | AUGGGGAACA | CCAUCACAUG | CUAUGUGAAA | GCCUUAGCGG | CCUGUAAGGC | 8580 |
| UGCAGGGAUA | AUUGCGCCCA | CAAUGCUGGU | AUGCGGCGAU | GACUUGGUUG | UCAUCUCAGA | 8640 |
| GAGCCAGGGG | ACCGAGGAGG | ACGAGCGGAA | CCUGAGAGCC | UUCACGGAGG | CUAUGACCAG | 8700 |
| GUAUUCUGCC | CCUCCUGGUG | ACCCCCCAG | ACCGGAAUAU | GACCUGGAGC | UGAUAACAUC | 8760 |
| UUGCUCCUCA | AAUGUGUCUG | UGGCGUUGGG | CCCACAAGGC | CGCCGCAGAU | ACUACCUGAC | 8820 |
| CAGAGACCCU | ACCACUCCAA | UCGCCCGGGC | UGCCUGGAA | ACAGUUAGAC | ACUCCCCUGU | 8880 |
| CAAUUCAUGG | CUAGGAAACA | UCAUCCAGUA | CGCCCCAACC | AUAUGGGCUC | GCAUGGUCCU | 8940 |
| GAUGACACAC | UUCUUCUCCA | UUCUCAUGGC | CCAAGAUACU | CUGGACCAGA | ACCUCAACUU | 9000 |
| UGAGAUGUAC | GGAGCGGUGU | ACUCCGUGAG | UCCCUUGGAC | CUCCAGCCA | UAAUUGAAAG | 9060 |
| GUUACACGGG | CUUGACGCUU | UCUCUCUGCA | CACAUACACU | CCCACGAAC | UGACACGGGU | 9120 |
| GGCUUCAGCC | CUCAGAAAAC | UUGGGGCGCC | ACCCUCAGA | GCGUGGAAGA | GCCGGGCACG | 9180 |
| UGCAGUCAGG | GCGUCCCUCA | UCUCCGUGG | GGGAGAGCG | GCCGUUUGCG | GCCGAUAUCU | 9240 |
| CUUCAACUGG | GCGGUGAAGA | CCAAGCUCAA | ACUCACUCCA | UUGCCGGAAG | CGCGCCUCCU | 9300 |
| GGAUUUAUCC | AGCUGGUUCA | CUGUCGGCGC | CGGCGGGGGC | GACAUUUAUC | ACAGCGUGUC | 9360 |
| GCGUGCCCGA | CCCCGCUUAU | UACUCCUUGG | CCUACUCCUA | CUUUUUGUAG | GGGUAGGCCU | 9420 |
| UUUCCUACUC | CCCGCUCGGU | AGAGCGGCAC | ACAUUAGCUA | CACUCCAUAG | CUAACUGUCC | 9480 |
| CUUUUUUUUU | UUUUUUUUUU | UUUUUUUUUU | UUUUUUUUUU | UUUUUUUUUU | UUUUUUUUUU | 9540 |
| UUUUUUUUUU | UUUUUUUUUU | UUUUUUUUUU | UUUUUUUUUU | UUUUUUUU | | 9589 |

( 2 ) INFORMATION FOR SEQ ID NO:2:

(i) SEQUENCE CHARACTERISTICS:
    (A) LENGTH: 9589 base pairs
    (B) TYPE: nucleic acid
    (C) STRANDEDNESS: single
    (D) TOPOLOGY: linear (xi) SEQUENCE DESCRIPTION: SEQ ID NO:2:

| | | | | | | |
|---|---|---|---|---|---|---|
| ACCCGCCCCT | AATAGGGGCG | ACACTCCGCC | ATGAACCACT | CCCCTGTGAG | GAACTACTGT | 60 |
| CTTCACGCAG | AAAGCGTCTA | GCCATGGCGT | TAGTATGAGT | GTCGTACAGC | CTCCAGGCCC | 120 |
| CCCCCTCCCG | GGAGAGCCAT | AGTGGTCTGC | GGAACCGGTG | AGTACACCGG | AATTGCCGGG | 180 |
| AAGACTGGGT | CCTTTCTTGG | ATAAACCCAC | TCTATGCCCG | GTCATTTGGG | CGTGCCCCCG | 240 |
| CAAGACTGCT | AGCCGAGTAG | CGTTGGGTTG | CGAAAGGCCT | TGTGGTACTG | CCTGATAGGG | 300 |
| TGCTTGCGAG | TGCCCCGGGA | GGTCTCGTAG | ACCGTGCACC | ATGAGCACAA | ATCCTAAACC | 360 |
| TCAAAGAAAA | ACCAAAAGAA | ACACCAACCG | TCGCCCACAA | GACGTTAAGT | TTCCGGGCGG | 420 |
| CGGCCAGATC | GTTGGCGGAG | TATACTTGTT | GCCGCGCAGG | GGCCCCAGGT | TGGGTGTGCG | 480 |
| CGCGACAAGG | AAGACTTCGG | AGCGGTCCCA | GCCACGTGGA | AGGCGCCAGC | CCATCCCTAA | 540 |
| GGATCGGCGC | TCCACTGGCA | AATCCTGGGG | AAAACCAGGA | TACCCCTGGC | CCCTATACGG | 600 |
| GAATGAGGGA | CTCGGCTGGG | CAGGATGGCT | CCTGTCCCCC | CGAGGTTCCC | GTCCCTCTTG | 660 |
| GGGCCCCAAT | GACCCCCGGC | ATAGGTCCCG | CAACGTGGGT | AAGGTCATCG | ATACCCTAAC | 720 |
| GTGCGGCTTT | GCCGACCTCA | TGGGGTACAT | CCCTGTCGTA | GGCGCCCCGC | TCGGCGGCGT | 780 |
| CGCCAGAGCT | CTCGCGCATG | GCGTGAGAGT | CCTGGAGGAC | GGGGTTAATT | TTGCAACAGG | 840 |
| GAACTTACCC | GGTTGCTCCT | TTTCTATCTT | CTTGCTGGCC | CTGCTGTCCT | GCATCACCAC | 900 |
| CCCGGTCTCC | GCTGCCGAAG | TGAAGAACAT | CAGTACCGGC | TACATGGTGA | CCAACGACTG | 960 |
| CACCAATGAT | AGCATTACCT | GGCAACTCCA | GGCTGCTGTC | CTCCACGTCC | CCGGGTGCGT | 1020 |
| CCCGTGCGAG | AAAGTGGGGA | ATACATCTCG | GTGCTGGATA | CCGGTCTCAC | CGAATGTGGC | 1080 |
| CGTGCAGCAG | CCCGGCGCCC | TCACGCAGGG | CTTACGGACG | CACATTGACA | TGGTTGTGAT | 1140 |
| GTCCGCCACG | CTCTGCTCCG | CTCTTTACGT | GGGGGACCTC | TGCGGTGGGG | TGATGCTTGC | 1200 |
| AGCCCAGATG | TTCATTGTCT | CGCCACAGCA | CCACTGGTTT | GTGCAAGACT | GCAATTGCTC | 1260 |
| CATCTACCCT | GGTACCATCA | CTGGACACCG | CATGGCGTGG | GACATGATGA | TGAACTGGTC | 1320 |
| GCCCACGGCT | ACCATGATCC | TGGCGTACGC | GATGCGCGTC | CCCGAGGTCA | TCATAGACAT | 1380 |
| CATTGGCGGG | GCTCATTGGG | GCGTCATGTT | CGGCTTAGCC | TACTTCTCTA | TGCAGGGAGC | 1440 |
| GTGGGCAAAA | GTCGTTGTCA | TTCTTTTGCT | GGCCGCCGGG | GTGGACGCGC | AAACCCATAC | 1500 |
| CGTTGGGGGT | TCTACCGCGC | ATAACGCCAG | GACCCTCACC | GGCATGTTCT | CCCTTGGTGC | 1560 |
| CAGGCAGAAA | ATCCAGCTCA | TCAACACCAA | TGGCAGTTGG | CACATCAACC | GCACCGCCCT | 1620 |
| GAACTGCAAT | GACTCTTTGC | ACACCGGCTT | CCTCGCGTCA | CTGTTCTACA | CCCACAGCTT | 1680 |
| CAACTCGTCA | GGATGTCCCG | AACGCATGTC | CGCCTGCCGC | AGTATCGAGG | CCTTTCGGGT | 1740 |
| GGGATGGGGC | GCCTTACAAT | ATGAGGACAA | TGTCACCAAT | CCAGAGGATA | TGAGACCGTA | 1800 |
| TTGCTGGCAC | TACCCACCAA | GACAGTGTGG | TGTAGTCTCC | GCGAGCTCTG | TGTGTGGCCC | 1860 |
| AGTGTACTGT | TTCACCCCCA | GCCCAGTAGT | AGTGGGTACG | ACCGATAGAC | TTGGAGCGCC | 1920 |
| CACTTACACG | TGGGGGGAGA | ATGAGACAGA | TGTCTTCCTA | TTGAACAGCA | CTCGACCACC | 1980 |
| GCAGGGGTCA | TGGTTCGGCT | GCACGTGGAT | GAACTCCACT | GGCTACACCA | AGACTTGCGG | 2040 |
| CGCACCACCC | TGCCGCATTA | GAGCTGACTT | CAATGCCAGC | ATGGACTTGT | TGTGCCCCAC | 2100 |
| GGACTGTTTT | AGGAAGCATC | CTGATACCAC | CTACATCAAA | TGTGGCTCTG | GCCCTGGCT | 2160 |
| CACGCCAAGG | TGCCTGATCG | ACTACCCCTA | CAGGCTCTGG | CATTACCCCT | GCACAGTTAA | 2220 |

| | | | | | |
|---|---|---|---|---|---|
| CTATACCATC | TTCAAAATAA | GGATGTATGT | GGGGGGGGTC | GAGCACAGGC | TCACGGCTGC | 2280 |
| GTGCAATTTC | ACTCGTGGGG | ATCGTTGCAA | CTTGGAGGAC | AGAGACAGAA | GTCAACTGTC | 2340 |
| TCCTTTGCTG | CACTCCACCA | CGGAGTGGGC | CATTTTACCT | TGCACTTACT | CGGACCTGCC | 2400 |
| CGCCTTGTCG | ACTGGTCTTC | TCCACCTCCA | CCAAAACATC | GTGGACGTGC | AATTCATGTA | 2460 |
| TGGCCTATCA | CCTGCTCTCA | CAAAATACAT | CGTCCGATGG | GAGTGGGTAG | TACTCTTATT | 2520 |
| CCTGCTCTTA | GCGGACGCCA | GGGTTTGCGC | CTGCTTATGG | ATGCTCATCT | TGTTGGGCCA | 2580 |
| GGCCGAAGCA | GCACTAGAGA | AGTTGGTCGT | CTTGCACGCT | GCGAGCGCAG | CTAGCTGCAA | 2640 |
| TGGCTTCCTA | TACTTTGTCA | TCTTTTTCGT | GGCTGCTTGG | TACATCAAGG | GTCGGGTAGT | 2700 |
| CCCCTTGGCT | ACTTATTCCC | TCACTGGCCT | ATGGTCCTTT | GCCTACTGC | TCCTAGCATT | 2760 |
| GCCCCAACAG | GCTTATGCTT | ATGACGCATC | TGTACATGGT | CAGATAGGAG | CAGCTCTGTT | 2820 |
| GGTACTGATC | ACTCTCTTTA | CACTCACCCC | CGGGTATAAG | ACCCTTCTCA | GCCGGTTTCT | 2880 |
| GTGGTGGTTG | TGCTATCTTC | TGACCCTGGC | GGAAGCTATG | GTCCAGGAGT | GGGCACCACC | 2940 |
| TATGCAGGTG | CGCGGTGGCC | GTGATGGGAT | CATATGGGCC | GTCGCCATAT | TCTGCCCGGG | 3000 |
| TGTGGTGTTT | GACATAACCA | AGTGGCTCTT | GGCGGTGCTT | GGGCTGCTT | ATCTCCTAAA | 3060 |
| AGGTGCTTTG | ACGCGTGTGC | CGTACTTCGT | CAGGGCTCAC | GCTCTACTAA | GGATGTGCAC | 3120 |
| CATGGTAAGG | CATCTCGCGG | GGGGTAGGTA | CGTCCAGATG | GTGCTACTAG | CCCTTGGCAG | 3180 |
| GTGGACTGGC | ACTTACATCT | ATGACCACCT | CACCCCTATG | TCGGATTGGG | CTGCTAATGG | 3240 |
| CCTGCGGGAC | TTGGCGGTCG | CCGTGGAGCC | TATCATCTTC | AGTCCGATGG | AGAAAAAGT | 3300 |
| CATCGTCTGG | GGAGCGGAGA | CAGCTGCTTG | CGGGGATATC | TTACACGGAC | TTCCCGTGTC | 3360 |
| CGCCCGACTT | GGCCGGGAGG | TCCTCCTTGG | CCCAGCTGAT | GGCTATACCT | CCAAGGGGTG | 3420 |
| GAGTCTTCTC | GCCCCCATCA | CTGCTTATGC | CCAGCAGACA | CGCGGCCTTT | TGGGCACCAT | 3480 |
| AGTGGTGAGC | ATGACGGGGC | GCGACAAGAC | AGAACAGGCC | GGGGAGATTC | AGGTCCTGTC | 3540 |
| CACGGTCACT | CAGTCCTTCC | TCGGAACAAC | CATCTCGGGG | GTCTTATGGA | CTGTCTACCA | 3600 |
| TGGAGCTGGC | AACAAGACTC | TAGCCGGCTC | ACGGGGTCCG | GTCACACAGA | TGTACTCCAG | 3660 |
| TGCTGAGGGG | GACTTAGTGG | GGTGGCCCAG | CCCCCCCGGG | ACCAAATCTT | GGAGCCGTG | 3720 |
| CACGTGTGGA | GCGGTCGACC | TATACCTGGT | CACGCGAAAC | GCTGATGTCA | TCCCGGCTCG | 3780 |
| AAGACGCGGG | GACAAGCGAG | GAGCGCTACT | CTCCCCGAGA | CCTCTTTCCA | CCTTGAAGGG | 3840 |
| GTCCTCGGGG | GGCCCGGTGC | TCTGCCCCAG | AGGCCACGCT | GTCGGGGTCT | TCCGGGCAGC | 3900 |
| CGTGTGCTCC | CGGGGCGTGG | CCAAGTCCAT | AGATTTTATC | CCCGTTGAGA | CACTTGACAT | 3960 |
| CGTCACTCGG | TCCCCCACCT | TTAGTGACAA | CAGCACACCA | CCTGCTGTGC | CCCAAACTTA | 4020 |
| TCAGGTCGGG | TACTTACATG | CCCCGACTGG | TAGTGGAAAG | AGCACCAAAG | TCCCTGTCGC | 4080 |
| GTATGCCGCT | CAGGGGTACA | AAGTGCTAGT | GCTTAATCCC | TCGGTGGCTG | CCACCCTGGG | 4140 |
| GTTTGGGGCG | TACTTGTCCA | AGGCACATGG | CATCAATCCC | AACATTAGGA | CTGGGGTCAG | 4200 |
| GACTGTGACG | ACCGGGGCGC | CCATCACGTA | CTCCACATAT | GGCAAATTCC | TCGCCGATGG | 4260 |
| GGGCTGCGCA | GGCGGCGCCT | ATGACATCAT | CATATGCGAT | GAATGCCATG | CCGTGGACTC | 4320 |
| TACCACCATT | CTCGGCATCG | GAACAGTCCT | CGATCAAGCA | GAGACAGCCG | GGTCAGGCT | 4380 |
| AACTGTACTG | GCTACGGCTA | CGCCCCCCGG | GTCAGTGACA | ACCCCCCACC | CCAACATAGA | 4440 |
| GGAGGTGGCC | CTCGGGCAGG | AGGGTGAGAT | CCCCTTCTAT | GGGAGGGCGA | TTCCCCTGTC | 4500 |
| ATACATCAAG | GGAGGAAGAC | ACTTGATCTT | CTGCCACTCA | AGAAAAAGT | GTGACGAGCT | 4560 |
| CGCGGCGGCC | CTTCGGGGTA | TGGGCTTGAA | CGCAGTGGCA | TACTACAGAG | GGCTGGACGT | 4620 |
| CTCCGTAATA | CCAACTCAGG | GAGACGTAGT | GGTCGTCGCC | ACCGACGCCC | TCATGACGGG | 4680 |

```
GTTTACTGGA  GACTTTGACT  CCGTGATCGA  CTGCAACGTA  GCGGTCACTC  AAGTTGTAGA   4740
CTTCAGCTTG  GACCCCACAT  TCACCATAAC  CACACAGACT  GTCCCTCAAG  ACGCTGTCTC   4800
ACGTAGCCAG  CGCCGGGGCC  GCACGGGCAG  GGGAAGACTG  GGTATTTATA  GGTATGTTTC   4860
CACTGGTGAG  CGAGCCTCAG  GAATGTTTGA  CAGTGTAGTG  CTCTGCGAGT  GCTACGATGC   4920
AGGGGCCGCA  TGGTATGAGC  TCACACCAGC  GGAGACCACC  GTCAGGCTCA  GAGCATATTT   4980
CAACACACCT  GGTTTGCCTG  TGTGCCAAGA  CCATCTTGAG  TTTTGGGAGG  CAGTTTTCAC   5040
CGGCCTCACA  CACATAGATG  CCCACTTCCT  TTCCCAAACA  AAGCAATCGG  GGGAAAATTT   5100
CGCATACTTA  ACAGCCTACC  AGGCTACAGT  GTGCGCTAGG  GCCAAAGCCC  CCCCCCCGTC   5160
CTGGGACGTC  ATGTGGAAGT  GTTTGACTCG  ACTCAAGCCC  ACACTCGTGG  GCCCCACACC   5220
TCTCCTGTAC  CGCTTGGGCT  CTGTTACCAA  CGAGGTCACC  CTCACGCATC  CTGTGACGAA   5280
ATACATCGCC  ACCTGCATGC  AAGCCGACCT  TGAGGTCATG  ACCAGCACGT  GGGTCTTAGC   5340
TGGGGGGGTC  TTGGCGGCCG  TCGCCGCGTA  CTGCCTGGCG  ACCGGGTGTG  TTTGCATCAT   5400
CGGCCGCTTG  CACGTTAACC  AGCGAGCCGT  CGTTGCACCG  GACAAGGAGG  TCCTCTATGA   5460
GGCTTTTGAT  GAGATGGAGG  AATGTGCCTC  TAGAGCGGCT  CTCATTGAAG  AGGGGCAGCG   5520
GATAGCCGAG  ATGCTGAAGT  CCAAGATCCA  AGGCTTATTG  CAGCAAGCTT  CCAAACAAGC   5580
TCAAGACATA  CAACCCGCTG  TGCAGGCTTC  TTGGCCCAAG  GTAGAGCAAT  TCTGGGCCAA   5640
ACACATGTGG  AACTTCATCA  GCGGCATTCA  ATACCTCGCA  GGACTATCAA  CACTGCCAGG   5700
GAACCCTGCT  GTAGCTTCCA  TGATGGCATT  CAGTGCCGCC  CTCACCAGTC  CGTTGTCAAC   5760
TAGCACCACT  ATCCTTCTCA  ACATTTTGGG  GGGCTGGCTA  GCATCCCAAA  TTGCGCCTCC   5820
CGCGGGGGCT  ACCGGCTTCG  TCGTCAGTGG  CCTGGTGGGG  CTGCCGTAG  GCAGCATAGG   5880
CTTGGGTAAG  GTGCTGGTGG  ACATCCTGGC  AGGGTATGGT  GCGGGCATTT  CGGGGGCTCT   5940
CGTCGCATTC  AAGATCATGT  CTGGCGAGAA  GCCCTCCATG  GAGGATGTTG  TCAACCTGCT   6000
GCCTGGAATT  CTGTCTCCGG  GTGCCCTGGT  GGTGGGAGTC  ATCTGCGCGG  CCATCCTGCG   6060
CCGACACGTG  GGACCGGGGG  AAGGCGCTGT  CCAATGGATG  AATAGGCTCA  TTGCCTTTGC   6120
TTCCAGAGGA  AACCACGTCG  CCCCCACCCA  CTACGTGACG  GAGTCGGATG  CGTCGCAGCG   6180
TGTGACCCAA  CTACTTGGCT  CCCTTACCAT  AACCAGCCTG  CTCAGGAGAC  TCCACAACTG   6240
GATTACTGAA  GACTGCCCCA  TCCCATGCAG  CGGCTCGTGG  CTCCGCGATG  TGTGGGATTG   6300
GGTTTGCACC  ATCCTAACAG  ACTTTAAAAA  CTGGCTGACC  TCCAAATTGT  TCCCAAAGAT   6360
GCCTGGTCTC  CCCTTTATCT  CTTGTCAAAA  GGGGTACAAG  GGCGTGTGGG  CTGGCACTGG   6420
TATCATGACC  ACACGGTGTC  CTTGCGGCGC  CAATATCTCT  GGCAATGTCC  GCCTGGGCTC   6480
CATGAGAATT  ACGGGGCCCA  AAACCTGCAT  GAATATCTGG  CAGGGGACCT  TTCCCATCAA   6540
TTGTTACACG  GAGGGCCAGT  GCGTGCCGAA  ACCCGCACCA  AACTTTAAGA  TCGCCATCTG   6600
GAGGGTGGCG  GCCTCAGAGT  ACGCGGAGGT  GACGCAGCAC  GGGTCATACC  ACTACATAAC   6660
AGGACTTACC  ACTGATAACT  TGAAAGTTCC  TTGCCAACTA  CCTTCTCCAG  AGTTCTTTTC   6720
CTGGGTGGAC  GGAGTGCAGA  TCCATAGGTT  TGCCCCCATA  CCGAAGCCGT  TTTTTCGGGA   6780
TGAGGTCTCG  TTCTGCGTTG  GGCTTAATTC  ATTTGTCGTC  GGGTCTCAGC  TCCCTTGCGA   6840
TCCTGAACCT  GACACAGACG  TATTGACGTC  CATGCTAACA  GACCCATCCC  ATATCACGGC   6900
GGAGACTGCA  GCGCGGCGTT  TGGCACGGGG  GTCACCCCCG  TCCGAGGCAA  GCTCCTCAGC   6960
GAGCCAGCTA  TCGGCACCAT  CGCTGCGAGC  CACCTGCACC  ACCCACGGCA  AGGCCTATGA   7020
TGTGGACATG  GTGGATGCCA  ACCTGTTCAT  GGGGGGCGAT  GTGACCCGGA  TAGAGTCTGA   7080
GTCCAAAGTG  GTCGTTCTGG  ACTCTCTCGA  CCCAATGGTC  GAAGAAAGGA  GCGACCTTGA   7140
```

```
GCCTTCGATA CCATCGGAAT ATATGCTCCC CAAGAAGAGA TTCCCACCAG CCTTACCGGC    7200
TTGGGCACGG CCTGATTACA ACCCACCGCT TGTGGAATCG TGGAAGAGGC CAGATTACCA    7260
ACCGGCCACT GTTGCGGGCT GCGCTCTCCC CCCCCCTAAG AAAACCCCGA CGCCTCCCCC    7320
AAGGAGACGC CGGACAGTGG GTCTGAGTGA GAGCTCCATA GCAGATGCCC TACAACAGCT    7380
GGCCATCAAG TCCTTTGGCC AGCCCCCCCC AAGCGGCGAT TCAGGCCTTT CCACGGGGGC    7440
GGACGCAGCC GATTCCGGCA GTCGGACGCC CCCCGATGAG TTGGCCCTTT CGGAGACAGG    7500
TTCCATCTCC TCCATGCCCC CTCTCGAGGG GGAGCCTGGA GATCCAGACT GGAGCCTGA    7560
GCAGGTAGAG CTTCAACCTC CCCCCCAGGG GGGGTGGTA ACCCCCGGCT CAGGCTCGGG    7620
GTCTTGGTCT ACTTGCTCCG AGGAGGACGA CTCCGTCGTG TGCTGCTCCA TGTCATACTC    7680
CTGGACCGGG GCTCTAATAA CTCCTTGTAG CCCCGAAGAG GAAAGTTGC CAATTGGCCC    7740
CTTGAGCAAC TCCCTGTTGC GATATCACAA CAAGGTGTAC TGTACCACAT CAAAGAGCGC    7800
CTCATTAAGG GCTAAAAAGG TAACTTTTGA TAGGATGCAA GCGCTCGACG CTCATTATGA    7860
CTCAGTCTTG AAGGACATTA AGCTAGCGGC CTCCAAGGTC ACCGCAAGGC TTCTCACTTT    7920
AGAGGAGGCC TGCCAGTTAA CTCCACCCCA CTCTGCAAGA TCCAAGTATG GGTTGGGGC    7980
TAAGGAGGTC CGCAGCTTGT CCGGGAGAGC CGTTAACCAC ATCAAGTCCG TGTGGAAGGA    8040
CCTCCTGGAA GACACACAAA CACCAATTCC TACAACCATC ATGGCCAAAA ATGAGGTGTT    8100
CTGCGTGGAC CCCACCAAGG GGGTAAGAA AGCAGCTCGC CTTATCGTTT ACCCTGACCT    8160
CGGCGTCAGG GTCTGCGAGA AAATGGCCCT TTATGATATC ACACAAAAGC TTCCTCAGGC    8220
GGTGATGGGG GCTTCTTATG GATTCCAGTA CTCCCCCGCT CAGCGGGTGG AGTTTCTCTT    8280
GAAGGCATGG GCGGAAAAGA AAGACCCTAT GGGTTTTTCG TATGATACCC GATGCTTTGA    8340
CTCAACCGTC ACTGAGAGAG ACATCAGGAC TGAGGAGTCC ATATATCGGG CTTGTTCCTT    8400
GCCCGAGGAG GCCCACACTG CCATACACTC ACTGACTGAG AGACTTTACG TGGGAGGGCC    8460
CATGTTCAAC AGCAAGGGCC AGACCTGCGG GTACAGGCGT TGCCGCGCCA GCGGGGTGCT    8520
TACCACTAGC ATGGGGAACA CCATCACATG CTATGTGAAA GCCTTAGCGG CCTGTAAGGC    8580
TGCAGGGATA ATTGCGCCCA CAATGCTGGT ATGCGGCGAT GACTTGGTTG TCATCTCAGA    8640
GAGCCAGGGG ACCGAGGAGG ACGAGCGGAA CCTGAGAGCC TTCACGGAGG CTATGACCAG    8700
GTATTCTGCC CCTCCTGGTG ACCCCCCAG ACCGGAATAT GACCTGGAGC TGATAACATC    8760
TTGCTCCTCA AATGTGTCTG TGGCGTTGGG CCCACAAGGC CGCCGCAGAT ACTACCTGAC    8820
CAGAGACCCT ACCACTCCAA TCGCCCGGGC TGCCTGGGAA ACAGTTAGAC ACTCCCTGT    8880
CAATTCATGG CTAGGAAACA TCATCCAGTA CGCCCCAACC ATATGGGCTC GCATGGTCCT    8940
GATGACACAC TTCTTCTCCA TTCTCATGGC CCAAGATACT CTGGACCAGA ACCTCAACTT    9000
TGAGATGTAC GGAGCGGTGT ACTCCGTGAG TCCCTTGGAC CTCCCAGCCA TAATTGAAAG    9060
GTTACACGGG CTTGACGCTT TCTCTCTGCA CACATACACT CCCCACGAAC TGACACGGGT    9120
GGCTTCAGCC CTCAGAAAAC TTGGGGCGCC ACCCCTCAGA GCGTGGAAGA GCCGGGCACG    9180
TGCAGTCAGG GCGTCCCTCA TCTCCCGTGG GGGAGAGCG GCCGTTTGCG GCCGATATCT    9240
CTTCAACTGG GCGGTGAAGA CCAAGCTCAA ACTCACTCCA TTGCCGGAAG CGCGCCTCCT    9300
GGATTTATCC AGCTGGTTCA CTGTCGGCGC CGGCGGGGGC GACATTTATC ACAGCGTGTC    9360
GCGTGCCCGA CCCCGCTTAT TACTCCTTGG CCTACTCCTA CTTTTGTAG GGGTAGGCCT    9420
TTTCCTACTC CCCGCTCGGT AGAGCGGCAC ACATTAGCTA CACTCCATAG CTAACTGTCC    9480
CTTTTTTTTT TTTTTTTTTT TTTTTTTTTT TTTTTTTTTT TTTTTTTTTT TTTTTTTTTT    9540
TTTTTTTTTT TTTTTTTTTT TTTTTTTTTT TTTTTTTTTT TTTTTTTTT               9589
```

( 2 ) INFORMATION FOR SEQ ID NO:3:

( i ) SEQUENCE CHARACTERISTICS:
        ( A ) LENGTH: 3970 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

| | | | | | | |
|---|---|---|---|---|---|---|
| GGCATTACCC | CTGCACAGTT | AACTATACCA | TCTTCAAAAT | AAGGATGTAT | GTGGGGGGGG | 60 |
| TCGAGCACAG | GCTCACGGCT | GCGTGCAATT | TCACTCGTGG | GGATCGTTGC | AACTTGGAGG | 120 |
| ACAGAGACAG | AAGTCAACTG | TCTCCTTTGC | TGCACTCCAC | CACGGAGTGG | GCCATTTTAC | 180 |
| CTTGCACTTA | CTCGGACCTG | CCCGCCTTGT | CGACTGGTCT | TCTCCACCTC | CACCAAAACA | 240 |
| TCGTGGACGT | GCAATTCATG | TATGGCCTAT | CACCTGCTCT | CACAAATAC | ATCGTCCGAT | 300 |
| GGGAGTGGGT | AGTACTCTTA | TTCCTGCTCT | TAGCGGACGC | CAGGGTTTGC | GCCTGCTTAT | 360 |
| GGATGCTCAT | CTTGTTGGGC | CAGGCCGAAG | CAGCACTAGA | GAAGTTGGTC | GTCTTGCACG | 420 |
| CTGCGAGCGC | AGCTAGCTGC | AATGGCTTCC | TATACTTTGT | CATCTTTTC | GTGGCTGCTT | 480 |
| GGTACATCAA | GGGTCGGGTA | GTCCCCTTGG | CTACTTATTC | CCTCACTGGC | CTATGGTCCT | 540 |
| TTGGCCTACT | GCTCCTAGCA | TTGCCCCAAC | AGGCTTATGC | TTATGACGCA | TCTGTACATG | 600 |
| GTCAGATAGG | AGCAGCTCTG | TTGGTACTGA | TCACTCTCTT | TACACTCACC | CCCGGGTATA | 660 |
| AGACCCTTCT | CAGCCGGTTT | CTGTGGTGGT | TGTGCTATCT | TCTGACCCTG | GCGGAAGCTA | 720 |
| TGGTCCAGGA | GTGGGCACCA | CCTATGCAGG | TGCGCGGTGG | CCGTGATGGG | ATCATATGGG | 780 |
| CCGTCGCCAT | ATTCTGCCCG | GGTGTGGTGT | TTGACATAAC | CAAGTGGCTC | TTGGCGGTGC | 840 |
| TTGGGCCTGC | TTATCTCCTA | AAAGGTGCTT | TGACGCGTGT | GCCGTACTTC | GTCAGGGCTC | 900 |
| ACGCTCTACT | AAGGATGTGC | ACCATGGTAA | GGCATCTCGC | GGGGGGTAGG | TACGTCCAGA | 960 |
| TGGTGCTACT | AGCCCTTGGC | AGGTGGACTG | GCACTTACAT | CTATGACCAC | CTCACCCCTA | 1020 |
| TGTCGGATTG | GGCTGCTAAT | GGCCTGCGGG | ACTTGGCGGT | CGCCGTGGAG | CCTATCATCT | 1080 |
| TCAGTCCGAT | GGAGAAAAAA | GTCATCGTCT | GGGGAGCGGA | GACAGCTGCT | TGCGGGGATA | 1140 |
| TCTTACACGG | ACTTCCCGTG | TCCGCCCGAC | TTGGCCGGGA | GGTCCTCCTT | GGCCCAGCTG | 1200 |
| ATGGCTATAC | CTCCAAGGGG | TGGAGTCTTC | TCGCCCCCAT | CACTGCTTAT | GCCCAGCAGA | 1260 |
| CACGCGGCCT | TTTGGGCACC | ATAGTGGTGA | GCATGACGGG | GCGCGACAAG | ACAGAACAGG | 1320 |
| CCGGGGAGAT | TCAGGTCCTG | TCCACGGTCA | CTCAGTCCTT | CCTCGGAACA | ACCATCTCGG | 1380 |
| GGGTCTTATG | GACTGTCTAC | CATGGAGCTG | GCAACAAGAC | TCTAGCCGGC | TCACGGGGTC | 1440 |
| CGGTCACACA | GATGTACTCC | AGTGCTGAGG | GGGACTTAGT | GGGGTGGCCC | AGCCCCCCCG | 1500 |
| GGACCAAATC | TTTGGAGCCG | TGCACGTGTG | GAGCGGTCGA | CCTATACCTG | GTCACGCGAA | 1560 |
| ACGCTGATGT | CATCCCGGCT | CGAAGACGCG | GGGACAAGCG | AGGAGCGCTA | CTCTCCCCGA | 1620 |
| GACCTCTTTC | CACCTTGAAG | GGGTCCTCGG | GGGCCCGGT | GCTCTGCCCC | AGAGGCCACG | 1680 |
| CTGTCGGGGT | CTTCCGGGCA | GCCGTGTGCT | CCCGGGGCGT | GGCCAAGTCC | ATAGATTTTA | 1740 |
| TCCCCGTTGA | GACACTTGAC | ATCGTCACTC | GGTCCCCCAC | CTTTAGTGAC | AACAGCACAC | 1800 |
| CACCTGCTGT | GCCCCAAACT | TATCAGGTCG | GGTACTTACA | TGCCCCGACT | GGTAGTGGAA | 1860 |
| AGAGCACCAA | AGTCCCTGTC | GCGTATGCCG | CTCAGGGGTA | CAAAGTGCTA | GTGCTTAATC | 1920 |
| CCTCGGTGGC | TGCCACCCTG | GGGTTTGGGG | CGTACTTGTC | CAAGGCACAT | GGCATCAATC | 1980 |
| CCAACATTAG | GACTGGGGTC | AGGACTGTGA | CGACCGGGGC | GCCCATCACG | TACTCCACAT | 2040 |
| ATGGCAAATT | CCTCGCCGAT | GGGGGCTGCG | CAGGCGGCGC | CTATGACATC | ATCATATGCG | 2100 |

```
ATGAATGCCA TGCCGTGGAC TCTACCACCA TTCTCGGCAT CGGAACAGTC CTCGATCAAG    2160
CAGAGACAGC CGGGGTCAGG CTAACTGTAC TGGCTACGGC TACGCCCCCC GGGTCAGTGA    2220
CAACCCCCCA CCCCAACATA GAGGAGGTGG CCCTCGGGCA GGAGGGTGAG ATCCCCTTCT    2280
ATGGGAGGGC GATTCCCCTG TCATACATCA AGGGAGGAAG ACACTTGATC TTCTGCCACT    2340
CAAAGAAAAA GTGTGACGAG CTCGCGGCGG CCCTTCGGGG TATGGGCTTG AACGCAGTGG    2400
CATACTACAG AGGGCTGGAC GTCTCCGTAA TACCAACTCA GGGAGACGTA GTGGTCGTCG    2460
CCACCGACGC CCTCATGACG GGGTTACTG GAGACTTTGA CTCCGTGATC GACTGCAACG     2520
TAGCGGTCAC TCAAGTTGTA GACTTCAGCT TGGACCCCAC ATTCACCATA ACCACACAGA    2580
CTGTCCCTCA AGACGCTGTC TCACGTAGCC AGCGCCGGGG CCGCACGGGC AGGGGAAGAC    2640
TGGGTATTTA TAGGTATGTT TCCACTGGTG AGCGAGCCTC AGGAATGTTT GACAGTGTAG    2700
TGCTCTGCGA GTGCTACGAT GCAGGGGCCG CATGGTATGA GCTCACACCA GCGGAGACCA    2760
CCGTCAGGCT CAGAGCATAT TTCAACACAC CTGGTTTGCC TGTGTGCCAA GACCATCTTG    2820
AGTTTTGGGA GGCAGTTTTC ACCGGCCTCA CACACATAGA TGCCCACTTC CTTTCCCAAA    2880
CAAAGCAATC GGGGGAAAAT TTCGCATACT TAACAGCCTA CCAGGCTACA GTGTGCGCTA    2940
GGGCCAAAGC CCCCCCCCG TCCTGGGACG TCATGTGGAA GTGTTTGACT CGACTCAAGC     3000
CCACACTCGT GGGCCCCACA CCTCTCCTGT ACCGCTTGGG CTCTGTTACC AACGAGGTCA    3060
CCCTCACGCA TCCTGTGACG AAATACATCG CCACCTGCAT GCAAGCCGAC CTTGAGGTCA    3120
TGACCAGCAC GTGGGTCTTA GCTGGGGGGG TCTTGGCGGC CGTCGCCGCG TACTGCCTGG    3180
CGACCGGGTG TGTTTGCATC ATCGGCCGCT TGCACGTTAA CCAGCGAGCC GTCGTTGCAC    3240
CGGACAAGGA GGTCCTCTAT GAGGCTTTTG ATGAGATGGA GGAATGTGCC TCTAGAGCGG    3300
CTCTCATTGA AGAGGGGCAG CGGATAGCCG AGATGCTGAA GTCCAAGATC CAAGGCTTAT    3360
TGCAGCAAGC TTCCAAACAA GCTCAAGACA TACAACCCGC TGTGCAGGCT TCTTGGCCCA    3420
AGGTAGAGCA ATTCTGGGCC AAACACATGT GGAACTTCAT CAGCGGCATT CAATACCTCG    3480
CAGGACTATC AACACTGCCA GGGAACCCTG CTGTAGCTTC CATGATGGCA TTCAGTGCCG    3540
CCCTCACCAG TCCGTTGTCA ACTAGCACCA CTATCCTTCT CAACATTTTG GGGGGCTGGC    3600
TAGCATCCCA AATTGCGCCT CCCGCGGGGG CTACCGGCTT CGTCGTCAGT GGCCTGGTGG    3660
GGGCTGCCGT AGGCAGCATA GGCTTGGGTA AGGTGCTGGT GGACATCCTG GCAGGGTATG    3720
GTGCGGGCAT TTCGGGGGCT CTCGTCGCAT TCAAGATCAT GTCTGGCGAG AAGCCCTCCA    3780
TGGAGGATGT TGTCAACCTG CTGCCTGGAA TTCTGTCTCC GGGTGCCCTG GTGGTGGGAG    3840
TCATCTGCGC GGCCATCCTG CGCCGACACG TGGGACCGGG GGAAGGCGCT GTCCAATGGA    3900
TGAATAGGCT CATTGCCTTT GCTTCCAGAG GAAACCACGT CGCCCCCACC CACTACGTGA    3960
CGGAGTCGGA                                                          3970
```

( 2 ) INFORMATION FOR SEQ ID NO:4:

( i ) SEQUENCE CHARACTERISTICS:
        ( A ) LENGTH: 2693 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

```
ATTCTGTCTC CGGGTGCCCT GGTGGTGGGA GTCATCTGCG CGGCCATCCT GCGCCGACAC     60
GTGGGACCGG GGAAGGCGC TGTCCAATGG ATGAATAGGC TCATTGCCTT TGCTTCCAGA     120
GGAAACCACG TCGCCCCCAC CCACTACGTG ACGGAGTCGG ATGCGTCGCA GCGTGTGACC    180
CAACTACTTG GCTCCCTTAC CATAACCAGC CTGCTCAGGA GACTCCACAA CTGGATTACT    240
```

```
GAAGACTGCC CCATCCCATG CAGCGGCTCG TGGCTCCGCG ATGTGTGGGA TTGGGTTTGC      300
ACCATCCTAA CAGACTTTAA AAACTGGCTG ACCTCCAAAT TGTTCCCAAA GATGCCTGGT      360
CTCCCCTTTA TCTCTTGTCA AAAGGGGTAC AAGGGCGTGT GGGCTGGCAC TGGTATCATG      420
ACCACACGGT GTCCTTGCGG CGCCAATATC TCTGGCAATG TCCGCCTGGG CTCCATGAGA      480
ATTACGGGGC CCAAAACCTG CATGAATATC TGGCAGGGGA CCTTTCCCAT CAATTGTTAC      540
ACGGAGGGCC AGTGCGTGCC GAAACCCGCA CCAAACTTTA AGATCGCCAT CTGGAGGGTG      600
GCGGCCTCAG AGTACGCGGA GGTGACGCAG CACGGGTCAT ACCACTACAT AACAGGACTT      660
ACCACTGATA ACTTGAAAGT TCCTTGCCAA CTACCTTCTC CAGAGTTCTT TTCCTGGGTG      720
GACGGAGTGC AGATCCATAG GTTTGCCCCC ATACCGAAGC CGTTTTTTCG GGATGAGGTC      780
TCGTTCTGCG TTGGGCTTAA TTCATTTGTC GTCGGGTCTC AGCTCCCTTG CGATCCTGAA      840
CCTGACACAG ACGTATTGAC GTCCATGCTA ACAGACCCAT CCCATATCAC GGCGGAGACT      900
GCAGCGCGGC GTTTGGCACG GGGTCACCC CCGTCCGAGG CAAGCTCCTC AGCGAGCCAG       960
CTATCGGCAC CATCGCTGCG AGCCACCTGC ACCACCCACG GCAAGGCCTA TGATGTGGAC     1020
ATGGTGGATG CCAACCTGTT CATGGGGGGC GATGTGACCC GGATAGAGTC TGAGTCCAAA     1080
GTGGTCGTTC TGGACTCTCT CGACCCAATG GTCGAAGAAA GGAGCGACCT TGAGCCTTCG     1140
ATACCATCGG AATATATGCT CCCCAAGAAG AGATTCCCAC CAGCCTTACC GGCTTGGGCA     1200
CGGCCTGATT ACAACCCACC GCTTGTGGAA TCGTGGAAGA GGCCAGATTA CCAACCGGCC     1260
ACTGTTGCGG GCTGCGCTCT CCCCCCCCCT AAGAAACCC CGACGCCTCC CCAAGGAGA       1320
CGCCGGACAG TGGGTCTGAG TGAGAGCTCC ATAGCAGATG CCCTACAACA GCTGGCCATC     1380
AAGTCCTTTG CCAGCCCCC CCCAAGCGGC GATTCAGGCC TTTCCACGGG GGCGGACGCA      1440
GCCGATTCCG GCAGTCGGAC GCCCCCCGAT GAGTTGGCCC TTTCGGAGAC AGGTTCCATC     1500
TCCTCCATGC CCCCTCTCGA GGGGGAGCCT GGAGATCCAG ACTTGGAGCC TGAGCAGGTA     1560
GAGCTTCAAC CTCCCCCCCA GGGGGGGGTG GTAACCCCCG GCTCAGGCTC GGGGTCTTGG     1620
TCTACTTGCT CCGAGGAGGA CGACTCCGTC GTGTGCTGCT CCATGTCATA CTCCTGGACC     1680
GGGGCTCTAA TAACTCCTTG TAGCCCCGAA GAGGAAAAGT TGCCAATTGG CCCCTTGAGC     1740
AACTCCCTGT TGCGATATCA CAACAAGGTG TACTGTACCA CATCAAAGAG CGCCTCATTA     1800
AGGGCTAAAA AGGTAACTTT TGATAGGATG CAAGCGCTCG ACGCTCATTA TGACTCAGTC     1860
TTGAAGGACA TTAAGCTAGC GGCCTCCAAG GTCACCGCAA GGCTTCTCAC TTTAGAGGAG     1920
GCCTGCCAGT TAACTCCACC CCACTCTGCA AGATCCAAGT ATGGGTTTGG GGCTAAGGAG     1980
GTCCGCAGCT TGTCCGGGAG AGCCGTTAAC CACATCAAGT CCGTGTGGAA GGACCTCCTG     2040
GAAGACACAC AAACACCAAT TCCTACAACC ATCATGGCCA AAAATGAGGT GTTCTGCGTG     2100
GACCCCACCA AGGGGGGTAA GAAAGCAGCT CGCCTTATCG TTTACCCTGA CCTCGGCGTC     2160
AGGGTCTGCG AGAAAATGGC CCTTTATGAT ATCACACAAA AGCTTCCTCA GGCGGTGATG     2220
GGGGCTTCTT ATGGATTCCA GTACTCCCCC GCTCAGCGGG TGGAGTTTCT CTTGAAGGCA     2280
TGGGCGGAAA AGAAAGACCC TATGGGTTTT TCGTATGATA CCCGATGCTT TGACTCAACC     2340
GTCACTGAGA GAGACATCAG GACTGAGGAG TCCATATATC GGGCTTGTTC CTTGCCCGAG     2400
GAGGCCCACA CTGCCATACA CTCACTGACT GAGAGACTTT ACGTGGGAGG GCCCATGTTC     2460
AACAGCAAGG GCCAGACCTG CGGGTACAGG CGTTGCCGCG CCAGCGGGGT GCTTACCACT     2520
AGCATGGGGA ACACCATCAC ATGCTATGTG AAAGCCTTAG CGGCCTGTAA GGCTGCAGGG     2580
ATAATTGCGC CCACAATGCT GGTATGCGGC GATGACTTGG TTGTCATCTC AGAGAGCCAG     2640
GGGACCGAGG AGGACGAGCG GAACCTGAGA GCCTTCACGG AGGCTATGAC CAG            2693
```

( 2 ) INFORMATION FOR SEQ ID NO:5:

( i ) SEQUENCE CHARACTERISTICS:
        ( A ) LENGTH: 3033 amino acids
        ( B ) TYPE: amino acid
        ( C ) STRANDEDNESS: unknown
        ( D ) TOPOLOGY: linear ( x i ) SEQUENCE DESCRIPTION: SEQ ID NO:5:

```
Met Ser Thr Asn Pro Lys Pro Gln Arg Lys Thr Lys Arg Asn Thr Asn
  1               5                  10                  15
Arg Arg Pro Gln Asp Val Lys Phe Pro Gly Gly Gly Gln Ile Val Gly
             20                  25                  30
Gly Val Tyr Leu Leu Pro Arg Arg Gly Pro Arg Leu Gly Val Arg Ala
             35                  40                  45
Thr Arg Lys Thr Ser Glu Arg Ser Gln Pro Arg Gly Arg Arg Gln Pro
 50                  55                  60
Ile Pro Lys Asp Arg Arg Ser Thr Gly Lys Ser Trp Gly Lys Pro Gly
 65                  70                  75                  80
Tyr Pro Trp Pro Leu Tyr Gly Asn Glu Gly Leu Gly Trp Ala Gly Trp
                 85                  90                  95
Leu Leu Ser Pro Arg Gly Ser Arg Pro Ser Trp Gly Pro Asn Asp Pro
            100                 105                 110
Arg His Arg Ser Arg Asn Val Gly Lys Val Ile Asp Thr Leu Thr Cys
            115                 120                 125
Gly Phe Ala Asp Leu Met Gly Tyr Ile Pro Val Val Gly Ala Pro Leu
            130                 135                 140
Gly Gly Val Ala Arg Ala Leu Ala His Gly Val Arg Val Leu Glu Asp
145                 150                 155                 160
Gly Val Asn Phe Ala Thr Gly Asn Leu Pro Gly Cys Ser Phe Ser Ile
                165                 170                 175
Phe Leu Leu Ala Leu Leu Ser Cys Ile Thr Thr Pro Val Ser Ala Ala
            180                 185                 190
Glu Val Lys Asn Ile Ser Thr Gly Tyr Met Val Thr Asn Asp Cys Thr
            195                 200                 205
Asn Asp Ser Ile Thr Trp Gln Leu Gln Ala Ala Val Leu His Val Pro
210                 215                 220
Gly Cys Val Pro Cys Glu Lys Val Gly Asn Thr Ser Arg Cys Trp Ile
225                 230                 235                 240
Pro Val Ser Pro Asn Val Ala Val Gln Gln Pro Gly Ala Leu Thr Gln
                245                 250                 255
Gly Leu Arg Thr His Ile Asp Met Val Val Met Ser Ala Thr Leu Cys
            260                 265                 270
Ser Ala Leu Tyr Val Gly Asp Leu Cys Gly Gly Val Met Leu Ala Ala
            275                 280                 285
Gln Met Phe Ile Val Ser Pro Gln His His Trp Phe Val Gln Asp Cys
            290                 295                 300
Asn Cys Ser Ile Tyr Pro Gly Thr Ile Thr Gly His Arg Met Ala Trp
305                 310                 315                 320
Asp Met Met Met Asn Trp Ser Pro Thr Ala Thr Met Ile Leu Ala Tyr
                325                 330                 335
Ala Met Arg Val Pro Glu Val Ile Ile Asp Ile Ile Gly Gly Ala His
            340                 345                 350
Trp Gly Val Met Phe Gly Leu Ala Tyr Phe Ser Met Gln Gly Ala Trp
            355                 360                 365
Ala Lys Val Val Val Ile Leu Leu Leu Ala Ala Gly Val Asp Ala Gln
```

-continued

|   |   |   | 370 |   |   |   | 375 |   |   |   |   | 380 |   |   |
|---|---|---|---|---|---|---|---|---|---|---|---|---|---|---|
| Thr | His | Thr | Val | Gly | Gly | Ser | Thr | Ala | His | Asn | Ala | Arg | Thr | Leu | Thr |
| 385 | | | | 390 | | | | | 395 | | | | | | 400 |
| Gly | Met | Phe | Ser | Leu | Gly | Ala | Arg | Gln | Lys | Ile | Gln | Leu | Ile | Asn | Thr |
| | | | | 405 | | | | | 410 | | | | | 415 | |
| Asn | Gly | Ser | Trp | His | Ile | Asn | Arg | Thr | Ala | Leu | Asn | Cys | Asn | Asp | Ser |
| | | | 420 | | | | | 425 | | | | | 430 | | |
| Leu | His | Thr | Gly | Phe | Leu | Ala | Ser | Leu | Phe | Tyr | Thr | His | Ser | Phe | Asn |
| | | 435 | | | | | 440 | | | | | 445 | | | |
| Ser | Ser | Gly | Cys | Pro | Glu | Arg | Met | Ser | Ala | Cys | Arg | Ser | Ile | Glu | Ala |
| | 450 | | | | | 455 | | | | | 460 | | | | |
| Phe | Arg | Val | Gly | Trp | Gly | Ala | Leu | Gln | Tyr | Glu | Asp | Asn | Val | Thr | Asn |
| 465 | | | | | 470 | | | | | 475 | | | | | 480 |
| Pro | Glu | Asp | Met | Arg | Pro | Tyr | Cys | Trp | His | Tyr | Pro | Pro | Arg | Gln | Cys |
| | | | | 485 | | | | | 490 | | | | | 495 | |
| Gly | Val | Val | Ser | Ala | Ser | Ser | Val | Cys | Gly | Pro | Val | Tyr | Cys | Phe | Thr |
| | | | | 500 | | | | | 505 | | | | | 510 | |
| Pro | Ser | Pro | Val | Val | Val | Gly | Thr | Thr | Asp | Arg | Leu | Gly | Ala | Pro | Thr |
| | | | 515 | | | | | 520 | | | | | 525 | | |
| Tyr | Thr | Trp | Gly | Glu | Asn | Glu | Thr | Asp | Val | Phe | Leu | Leu | Asn | Ser | Thr |
| | | 530 | | | | | 535 | | | | | 540 | | | |
| Arg | Pro | Pro | Gln | Gly | Ser | Trp | Phe | Gly | Cys | Thr | Trp | Met | Asn | Ser | Thr |
| 545 | | | | | 550 | | | | | 555 | | | | | 560 |
| Gly | Tyr | Thr | Lys | Thr | Cys | Gly | Ala | Pro | Pro | Cys | Arg | Ile | Arg | Ala | Asp |
| | | | | 565 | | | | | 570 | | | | | 575 | |
| Phe | Asn | Ala | Ser | Met | Asp | Leu | Leu | Cys | Pro | Thr | Asp | Cys | Phe | Arg | Lys |
| | | | | 580 | | | | | 585 | | | | | 590 | |
| His | Pro | Asp | Thr | Thr | Tyr | Ile | Lys | Cys | Gly | Ser | Gly | Pro | Trp | Leu | Thr |
| | | | 595 | | | | | 600 | | | | | 605 | | |
| Pro | Arg | Cys | Leu | Ile | Asp | Tyr | Pro | Tyr | Arg | Leu | Trp | His | Tyr | Pro | Cys |
| | 610 | | | | | 615 | | | | | 620 | | | | |
| Thr | Val | Asn | Tyr | Thr | Ile | Phe | Lys | Ile | Arg | Met | Tyr | Val | Gly | Gly | Val |
| 625 | | | | | 630 | | | | | 635 | | | | | 640 |
| Glu | His | Arg | Leu | Thr | Ala | Ala | Cys | Asn | Phe | Thr | Arg | Gly | Asp | Arg | Cys |
| | | | | 645 | | | | | 650 | | | | | 655 | |
| Asn | Leu | Glu | Asp | Arg | Asp | Arg | Ser | Gln | Leu | Ser | Pro | Leu | Leu | His | Ser |
| | | | 660 | | | | | 665 | | | | | 670 | | |
| Thr | Thr | Glu | Trp | Ala | Ile | Leu | Pro | Cys | Thr | Tyr | Ser | Asp | Leu | Pro | Ala |
| | | | 675 | | | | | 680 | | | | | 685 | | |
| Leu | Ser | Thr | Gly | Leu | Leu | His | Leu | His | Gln | Asn | Ile | Val | Asp | Val | Gln |
| | 690 | | | | | 695 | | | | | 700 | | | | |
| Phe | Met | Tyr | Gly | Leu | Ser | Pro | Ala | Leu | Thr | Lys | Tyr | Ile | Val | Arg | Trp |
| 705 | | | | | 710 | | | | | 715 | | | | | 720 |
| Glu | Trp | Val | Val | Leu | Leu | Phe | Leu | Leu | Leu | Ala | Asp | Ala | Arg | Val | Cys |
| | | | | 725 | | | | | 730 | | | | | 735 | |
| Ala | Cys | Leu | Trp | Met | Leu | Ile | Leu | Leu | Gly | Gln | Ala | Glu | Ala | Ala | Leu |
| | | | 740 | | | | | 745 | | | | | 750 | | |
| Glu | Lys | Leu | Val | Val | Leu | His | Ala | Ala | Ser | Ala | Ala | Ser | Cys | Asn | Gly |
| | | 755 | | | | | 760 | | | | | 765 | | | |
| Phe | Leu | Tyr | Phe | Val | Ile | Phe | Phe | Val | Ala | Ala | Trp | Tyr | Ile | Lys | Gly |
| | | 770 | | | | | 775 | | | | | 780 | | | |
| Arg | Val | Val | Pro | Leu | Ala | Thr | Tyr | Ser | Leu | Thr | Gly | Leu | Trp | Ser | Phe |
| 785 | | | | | 790 | | | | | 795 | | | | | 800 |
| Gly | Leu | Leu | Leu | Leu | Ala | Leu | Pro | Gln | Gln | Ala | Tyr | Ala | Tyr | Asp | Ala |
| | | | | 805 | | | | | 810 | | | | | 815 | |

```
Ser  Val  His  Gly  Gln  Ile  Gly  Ala  Ala  Leu  Leu  Val  Leu  Ile  Thr  Leu
              820                 825                      830

Phe  Thr  Leu  Thr  Pro  Gly  Tyr  Lys  Thr  Leu  Leu  Ser  Arg  Phe  Leu  Trp
              835                 840                      845

Trp  Leu  Cys  Tyr  Leu  Leu  Thr  Leu  Ala  Glu  Ala  Met  Val  Gln  Glu  Trp
     850                      855                 860

Ala  Pro  Pro  Met  Gln  Val  Arg  Gly  Gly  Arg  Asp  Gly  Ile  Ile  Trp  Ala
865                      870                 875                           880

Val  Ala  Ile  Phe  Cys  Pro  Gly  Val  Val  Phe  Asp  Ile  Thr  Lys  Trp  Leu
               885                      890                      895

Leu  Ala  Val  Leu  Gly  Pro  Ala  Tyr  Leu  Lys  Gly  Ala  Leu  Thr  Arg
               900                 905                      910

Val  Pro  Tyr  Phe  Val  Arg  Ala  His  Ala  Leu  Leu  Arg  Met  Cys  Thr  Met
          915                      920                      925

Val  Arg  His  Leu  Ala  Gly  Gly  Arg  Tyr  Val  Gln  Met  Val  Leu  Leu  Ala
          930                 935                      940

Leu  Gly  Arg  Trp  Thr  Gly  Thr  Tyr  Ile  Tyr  Asp  His  Leu  Thr  Pro  Met
945                      950                      955                      960

Ser  Asp  Trp  Ala  Ala  Asn  Gly  Leu  Arg  Asp  Leu  Ala  Val  Ala  Val  Glu
               965                      970                      975

Pro  Ile  Ile  Phe  Ser  Pro  Met  Glu  Lys  Lys  Val  Ile  Val  Trp  Gly  Ala
               980                 985                      990

Glu  Thr  Ala  Ala  Cys  Gly  Asp  Ile  Leu  His  Gly  Leu  Pro  Val  Ser  Ala
          995                      1000                     1005

Arg  Leu  Gly  Arg  Glu  Val  Leu  Leu  Gly  Pro  Ala  Asp  Gly  Tyr  Thr  Ser
     1010                     1015                     1020

Lys  Gly  Trp  Ser  Leu  Leu  Ala  Pro  Ile  Thr  Ala  Tyr  Ala  Gln  Gln  Thr
1025                     1030                     1035                     1040

Arg  Gly  Leu  Leu  Gly  Thr  Ile  Val  Val  Ser  Met  Thr  Gly  Arg  Asp  Lys
               1045                     1050                     1055

Thr  Glu  Gln  Ala  Gly  Glu  Ile  Glu  Val  Leu  Ser  Thr  Val  Thr  Gln  Ser
               1060                     1065                     1070

Phe  Leu  Gly  Thr  Thr  Ile  Ser  Gly  Val  Leu  Trp  Thr  Val  Tyr  His  Gly
          1075                     1080                     1085

Ala  Gly  Asn  Lys  Thr  Leu  Ala  Gly  Ser  Arg  Gly  Pro  Val  Thr  Gln  Met
     1090                     1095                     1100

Tyr  Ser  Ser  Ala  Glu  Gly  Asp  Leu  Val  Gly  Trp  Pro  Ser  Pro  Pro  Gly
1105                     1110                     1115                     1120

Thr  Lys  Ser  Leu  Glu  Pro  Cys  Thr  Cys  Gly  Ala  Val  Asp  Leu  Tyr  Leu
               1125                     1130                     1135

Val  Thr  Arg  Asn  Ala  Asp  Val  Ile  Pro  Ala  Arg  Arg  Arg  Gly  Asp  Lys
               1140                     1145                     1150

Arg  Gly  Ala  Leu  Leu  Ser  Pro  Arg  Pro  Leu  Ser  Thr  Leu  Lys  Gly  Ser
     1155                     1160                     1165

Ser  Gly  Gly  Pro  Val  Leu  Cys  Pro  Arg  Gly  His  Ala  Val  Gly  Val  Phe
     1170                     1175                     1180

Arg  Ala  Ala  Val  Cys  Ser  Arg  Gly  Val  Ala  Lys  Ser  Ile  Asp  Phe  Ile
1185                     1190                     1195                     1200

Pro  Val  Glu  Thr  Leu  Asp  Ile  Val  Thr  Arg  Ser  Pro  Thr  Phe  Ser  Asp
               1205                     1210                     1215

Asn  Ser  Thr  Pro  Pro  Ala  Val  Pro  Gln  Thr  Tyr  Gln  Val  Gln  Tyr  Leu
          1220                     1225                     1230

His  Ala  Pro  Thr  Gly  Ser  Gly  Lys  Ser  Thr  Lys  Val  Pro  Val  Ala  Tyr
          1235                     1240                     1245
```

```
Ala Ala Gln Gly Tyr Lys Val Leu Val Leu Asn Pro Ser Val Ala Ala
1250                 1255              1260

Thr Leu Gly Phe Gly Ala Tyr Leu Ser Lys Ala His Gly Ile Asn Pro
1265             1270             1275              1280

Asn Ile Arg Thr Gly Val Arg Thr Val Thr Thr Gly Ala Pro Ile Thr
             1285              1290              1295

Tyr Ser Thr Tyr Gly Lys Phe Leu Ala Asp Gly Gly Cys Ala Gly Gly
            1300             1305              1310

Ala Tyr Asp Ile Ile Ile Cys Asp Glu Cys His Ala Val Asp Ser Thr
            1315             1320              1325

Thr Ile Leu Gly Ile Gly Thr Val Leu Asp Gln Ala Glu Thr Ala Gly
            1330             1335              1340

Val Arg Leu Thr Val Leu Ala Thr Ala Thr Pro Pro Gly Ser Val Thr
1345             1350              1355              1360

Thr Pro His Pro Asn Ile Glu Glu Val Ala Leu Gly Gln Glu Gly Glu
                 1365             1370              1375

Ile Pro Phe Tyr Gly Arg Ala Ile Pro Leu Ser Tyr Ile Lys Gly Gly
            1380             1385              1390

Arg His Leu Ile Phe Cys His Ser Lys Lys Lys Cys Asp Glu Leu Ala
            1395             1400              1405

Ala Ala Leu Arg Gly Met Gly Leu Asn Ala Val Ala Tyr Tyr Arg Gly
            1410             1415              1420

Leu Asp Val Ser Val Ile Pro Thr Gln Gly Asp Val Val Val Val Ala
1425             1430              1435              1440

Thr Asp Ala Leu Met Thr Gly Phe Thr Gly Asp Phe Asp Ser Val Ile
                 1445             1450              1455

Asp Cys Asn Val Ala Val Thr Gln Val Val Asp Phe Ser Leu Asp Pro
             1460              1465              1470

Thr Phe Thr Ile Thr Thr Gln Thr Val Pro Gln Asp Ala Val Ser Arg
            1475             1480              1485

Ser Gln Arg Arg Gly Arg Thr Gly Arg Gly Arg Leu Gly Ile Tyr Arg
            1490             1495              1500

Tyr Val Ser Thr Gly Glu Arg Ala Ser Gly Met Phe Asp Ser Val Val
1505             1510              1515              1520

Leu Cys Glu Cys Tyr Asp Ala Gly Ala Ala Trp Tyr Glu Leu Thr Pro
                 1525             1530              1535

Ala Glu Thr Thr Val Arg Leu Arg Ala Tyr Phe Asn Thr Pro Gly Leu
            1540             1545              1550

Pro Val Cys Gln Asp His Leu Glu Phe Trp Glu Ala Val Phe Thr Gly
            1555             1560              1565

Leu Thr His Ile Asp Ala His Phe Leu Ser Gln Thr Lys Gln Ser Gly
            1570             1575              1580

Glu Asn Phe Ala Tyr Leu Thr Ala Tyr Gln Ala Thr Val Cys Ala Arg
1585             1590              1595              1600

Ala Lys Ala Pro Pro Pro Ser Trp Asp Val Met Trp Lys Cys Leu Thr
                 1605             1610              1615

Arg Leu Lys Pro Trp Leu Val Gly Pro Thr Pro Leu Leu Tyr Arg Leu
            1620             1625              1630

Gly Ser Val Thr Asn Glu Val Thr Leu Thr His Pro Val Thr Lys Tyr
            1635             1640              1645

Ile Ala Thr Cys Met Gln Ala Asp Leu Glu Val Met Thr Ser Thr Trp
            1650             1655              1660

Val Leu Ala Gly Gly Val Leu Ala Ala Val Ala Ala Tyr Cys Leu Ala
1665             1670              1675              1680

Thr Gly Cys Val Cys Ile Ile Gly Arg Leu His Val Asn Gln Arg Ala
```

```
                         1685                      1690                      1695
Val  Val  Ala  Pro  Asp  Lys  Glu  Val  Leu  Tyr  Glu  Ala  Phe  Asp  Glu  Met
               1700                      1705                      1710
Glu  Glu  Cys  Ala  Ser  Arg  Ala  Ala  Leu  Ile  Glu  Glu  Gly  Gln  Arg  Ile
               1715                      1720                      1725
Ala  Glu  Met  Leu  Lys  Ser  Lys  Ile  Gln  Gly  Leu  Leu  Gln  Gln  Ala  Ser
               1730                      1735                      1740
Lys  Gln  Ala  Gln  Asp  Ile  Gln  Pro  Ala  Val  Gln  Ala  Ser  Trp  Pro  Lys
1745                     1750                      1755                      1760
Val  Glu  Gln  Phe  Trp  Ala  Lys  His  Met  Trp  Asn  Phe  Ile  Ser  Gly  Ile
               1765                      1770                      1775
Gln  Tyr  Leu  Ala  Gly  Leu  Ser  Thr  Leu  Pro  Gly  Asn  Pro  Ala  Val  Ala
               1780                      1785                      1790
Ser  Met  Met  Ala  Phe  Ser  Ala  Ala  Leu  Thr  Ser  Pro  Leu  Ser  Thr  Ser
               1795                      1800                      1805
Thr  Thr  Ile  Leu  Leu  Asn  Ile  Leu  Gly  Gly  Trp  Leu  Ala  Ser  Gln  Ile
               1810                      1815                      1820
Ala  Pro  Pro  Ala  Gly  Ala  Thr  Gly  Phe  Val  Val  Ser  Gly  Leu  Val  Gly
1825                     1830                      1835                      1840
Ala  Ala  Val  Gly  Ser  Ile  Gly  Leu  Gly  Lys  Val  Leu  Val  Asp  Ile  Leu
               1845                      1850                      1855
Ala  Gly  Tyr  Gly  Ala  Gly  Ile  Ser  Gly  Ala  Leu  Val  Ala  Phe  Lys  Ile
               1860                      1865                      1870
Met  Ser  Gly  Glu  Lys  Pro  Ser  Met  Glu  Asp  Val  Val  Asn  Leu  Leu  Pro
               1875                      1880                      1885
Gly  Ile  Leu  Ser  Pro  Gly  Ala  Leu  Val  Val  Gly  Val  Ile  Cys  Ala  Ala
               1890                      1895                      1900
Ile  Leu  Arg  Arg  His  Val  Gly  Pro  Gly  Glu  Gly  Ala  Val  Gln  Trp  Met
1905                     1910                      1915                      1920
Asn  Arg  Leu  Ile  Ala  Phe  Ala  Ser  Arg  Gly  Asn  His  Val  Ala  Pro  Thr
               1925                      1930                      1935
His  Tyr  Val  Thr  Glu  Ser  Asp  Ala  Ser  Gln  Arg  Val  Thr  Gln  Leu  Leu
               1940                      1945                      1950
Gly  Ser  Leu  Thr  Ile  Thr  Ser  Leu  Leu  Arg  Arg  Leu  His  Asn  Trp  Ile
               1955                      1960                      1965
Thr  Glu  Asp  Cys  Pro  Ile  Pro  Cys  Ser  Gly  Ser  Trp  Leu  Arg  Asp  Val
               1970                      1975                      1980
Trp  Asp  Trp  Val  Cys  Thr  Ile  Leu  Thr  Asp  Phe  Lys  Asn  Trp  Leu  Thr
1985                     1990                      1995                      2000
Ser  Lys  Leu  Phe  Pro  Lys  Met  Pro  Gly  Leu  Pro  Phe  Ile  Ser  Cys  Gln
               2005                      2010                      2015
Lys  Gly  Tyr  Lys  Gly  Val  Trp  Ala  Gly  Thr  Gly  Ile  Met  Thr  Thr  Arg
               2020                      2025                      2030
Cys  Pro  Cys  Gly  Ala  Asn  Ile  Ser  Gly  Asn  Val  Arg  Leu  Gly  Ser  Met
               2035                      2040                      2045
Arg  Ile  Thr  Gly  Pro  Lys  Thr  Cys  Met  Asn  Ile  Trp  Gln  Gly  Thr  Phe
2050                     2055                      2060
Pro  Ile  Asn  Cys  Tyr  Thr  Glu  Gly  Gln  Cys  Val  Pro  Lys  Pro  Ala  Pro
2065                     2070                      2075                      2080
Asn  Phe  Lys  Ile  Ala  Ile  Trp  Arg  Val  Ala  Ala  Ser  Glu  Tyr  Ala  Glu
               2085                      2090                      2095
Val  Thr  Gln  His  Gly  Ser  Tyr  His  Tyr  Ile  Thr  Gly  Leu  Thr  Thr  Asp
               2100                      2105                      2110
Asn  Leu  Lys  Val  Pro  Cys  Gln  Leu  Pro  Ser  Pro  Glu  Phe  Phe  Ser  Trp
               2115                      2120                      2125
```

```
Val Asp Gly Val Gln Ile His Arg Phe Ala Pro Ile Pro Lys Pro Phe
    2130                2135                2140

Phe Arg Asp Glu Val Ser Phe Cys Val Gly Leu Asn Ser Phe Val Val
2145                2150                2155                2160

Gly Ser Gln Leu Pro Cys Asp Pro Glu Pro Asp Thr Asp Val Leu Thr
                2165                2170                2175

Ser Met Leu Thr Asp Pro Ser His Ile Thr Ala Glu Thr Ala Ala Arg
            2180                2185                2190

Arg Leu Ala Arg Gly Ser Pro Ser Glu Ala Ser Ser Ser Ala Ser
    2195                2200                2205

Gln Leu Ser Ala Pro Ser Leu Arg Ala Thr Cys Thr Thr His Gly Lys
    2210                2215                2220

Ala Tyr Asp Val Asp Met Val Asp Ala Asn Leu Phe Met Gly Gly Asp
2225                2230                2235                2240

Val Thr Arg Ile Glu Ser Glu Ser Lys Val Val Val Leu Asp Ser Leu
                2245                2250                2255

Asp Pro Met Val Glu Glu Arg Ser Asp Leu Glu Pro Ser Ile Pro Ser
            2260                2265                2270

Glu Tyr Met Leu Pro Lys Lys Arg Phe Pro Pro Ala Leu Pro Ala Trp
        2275                2280                2285

Ala Arg Pro Asp Tyr Asn Pro Pro Leu Val Glu Ser Trp Lys Arg Pro
2290                2295                2300

Asp Tyr Gln Pro Ala Thr Val Ala Gly Cys Ala Leu Pro Pro Pro Lys
2305                2310                2315                2320

Lys Thr Pro Thr Pro Pro Pro Arg Arg Arg Arg Thr Val Gly Leu Ser
                2325                2330                2335

Glu Ser Ser Ile Ala Asp Ala Leu Gln Gln Leu Ala Ile Lys Ser Phe
            2340                2345                2350

Gly Gln Pro Pro Pro Ser Gly Asp Ser Gly Leu Ser Thr Gly Ala Asp
        2355                2360                2365

Ala Ala Asp Ser Gly Ser Arg Thr Pro Pro Asp Glu Leu Ala Leu Ser
2370                2375                2380

Glu Thr Gly Ser Ile Ser Ser Met Pro Pro Leu Glu Gly Glu Pro Gly
2385                2390                2395                2400

Asp Pro Asp Leu Glu Pro Glu Gln Val Glu Leu Gln Pro Pro Pro Gln
                2405                2410                2415

Gly Gly Val Val Thr Pro Gly Ser Gly Ser Gly Ser Trp Ser Thr Cys
            2420                2425                2430

Ser Glu Glu Asp Asp Ser Val Val Cys Cys Ser Met Ser Tyr Ser Trp
        2435                2440                2445

Thr Gly Ala Leu Ile Thr Pro Cys Ser Pro Glu Glu Glu Lys Leu Pro
2450                2455                2460

Ile Asn Pro Leu Ser Asn Ser Leu Leu Arg Tyr His Asn Lys Val Tyr
2465                2470                2475                2480

Cys Thr Thr Ser Lys Ser Ala Ser Leu Arg Ala Lys Lys Val Thr Phe
                2485                2490                2495

Asp Arg Met Gln Ala Leu Asp Ala His Tyr Asp Ser Val Leu Lys Asp
            2500                2505                2510

Ile Lys Leu Ala Ala Ser Lys Val Thr Ala Arg Leu Leu Thr Leu Glu
        2515                2520                2525

Glu Ala Cys Gln Leu Thr Pro Pro His Ser Ala Arg Ser Lys Tyr Gly
    2530                2535                2540

Phe Gly Ala Lys Glu Val Arg Ser Leu Ser Gly Arg Ala Val Asn His
2545                2550                2555                2560
```

```
Ile Lys Ser Val Trp Lys Asp Leu Leu Glu Asp Thr Gln Thr Pro Ile
            2565                2570                2575

Pro Thr Thr Ile Met Ala Lys Asn Glu Val Phe Cys Val Asp Pro Thr
            2580                2585                2590

Lys Gly Gly Lys Lys Ala Ala Arg Leu Ile Val Tyr Pro Asp Leu Gly
            2595                2600                2605

Val Arg Val Cys Glu Lys Met Ala Leu Tyr Asp Ile Thr Gln Lys Leu
    2610                2615                2620

Pro Gln Ala Val Met Gly Ala Ser Tyr Gly Phe Gln Tyr Ser Pro Ala
2625                2630                2635                2640

Gln Arg Val Glu Phe Leu Leu Lys Ala Trp Ala Glu Lys Lys Asp Pro
            2645                2650                2655

Met Gly Phe Ser Tyr Asp Thr Arg Cys Phe Asp Ser Thr Val Thr Glu
            2660                2665                2670

Arg Asp Ile Arg Thr Glu Glu Ser Ile Tyr Arg Ala Cys Ser Leu Pro
    2675                2680                2685

Glu Glu Ala His Thr Ala Ile His Ser Leu Thr Glu Arg Leu Tyr Val
    2690                2695                2700

Gly Gly Pro Met Phe Asn Ser Lys Gly Gln Thr Cys Gly Tyr Arg Arg
2705                2710                2715                2720

Cys Arg Ala Ser Gly Val Leu Thr Thr Ser Met Gly Asn Thr Ile Thr
            2725                2730                2735

Cys Tyr Val Lys Ala Leu Ala Ala Cys Lys Ala Ala Gly Ile Ile Ala
            2740                2745                2750

Pro Thr Met Leu Val Cys Gly Asp Asp Leu Val Val Ile Ser Glu Ser
            2755                2760                2765

Gln Gly Thr Glu Glu Asp Glu Arg Asn Leu Arg Ala Phe Thr Glu Ala
            2770                2775                2780

Met Thr Arg Tyr Ser Ala Pro Pro Gly Asp Pro Pro Arg Pro Glu Tyr
2785                2790                2795                2800

Asp Leu Glu Leu Ile Thr Ser Cys Ser Ser Asn Val Ser Val Ala Leu
            2805                2810                2815

Gly Pro Gln Gly Arg Arg Arg Tyr Tyr Leu Thr Arg Asp Pro Thr Thr
            2820                2825                2830

Pro Ile Ala Arg Ala Ala Trp Glu Thr Val Arg His Ser Pro Val Asn
            2835                2840                2845

Ser Trp Leu Gly Asn Ile Ile Gln Tyr Ala Pro Thr Ile Trp Ala Arg
    2850                2855                2860

Met Val Leu Met Thr His Phe Phe Ser Ile Leu Met Ala Gln Asp Thr
2865                2870                2875                2880

Leu Asp Gln Asn Leu Asn Phe Glu Met Tyr Gly Ala Val Tyr Ser Val
            2885                2890                2895

Ser Pro Leu Asp Leu Pro Ala Ile Ile Glu Arg Leu His Gly Leu Asp
            2900                2905                2910

Ala Phe Ser Leu His Thr Tyr Thr Pro His Glu Leu Thr Arg Val Ala
            2915                2920                2925

Ser Ala Leu Arg Lys Leu Gly Ala Pro Pro Leu Arg Ala Trp Lys Ser
    2930                2935                2940

Arg Ala Arg Ala Val Arg Ala Ser Leu Ile Ser Arg Gly Gly Arg Ala
2945                2950                2955                2960

Ala Val Cys Gly Arg Tyr Leu Phe Asn Trp Ala Val Lys Thr Lys Leu
            2965                2970                2975

Lys Leu Thr Pro Leu Pro Glu Ala Arg Leu Leu Asp Leu Ser Ser Trp
            2980                2985                2990

Phe Thr Val Gly Ala Gly Gly Gly Asp Ile Tyr His Ser Val Ser Arg
```

5,428,145
                    49                                                50
                                         -continued

```
            2995                    3000                      3005
    Ala Arg Pro Arg Leu Leu Leu Gly Leu Leu Leu Leu Phe Val Gly
        3010                    3015                  3020

Val Gly Leu Phe Leu Leu Pro Ala Arg
        3025                3030
```

( 2 ) INFORMATION FOR SEQ ID NO:6:

( i ) SEQUENCE CHARACTERISTICS:
        ( A ) LENGTH: 9511 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

| | | | | | | |
|---|---|---|---|---|---|---|
| GCCCGCCCCC | UGAUGGGGGC | GACACUCCGC | CAUGAAUCAC | UCCCCUGUGA | GGAACUACUG | 60 |
| UCUUCACGCA | GAAAGCGUCU | AGCCAUGGCG | UUAGUAUGAG | UGUCGUACAG | CCUCCAGGCC | 120 |
| CCCCCUCCC | GGGAGAGCCA | UAGUGGUCUG | CGGAACCGGU | GAGUACACCG | GAAUUACCGG | 180 |
| AAAGACUGGG | UCCUUUCUUG | GAUAAACCCA | CUCUAUGUCC | GGUCAUUUGG | GCACGCCCCC | 240 |
| GCAAGACUGC | UAGCCGAGUA | GCGUUGGGUU | GCGAAAGGCC | UUGUGGUACU | GCCUGAUAGG | 300 |
| GURCUUGCGA | GUGCCCCGGG | AGGUCUCGUA | GACCGUGCAU | CAUGAGCACA | AUCCUAAAC | 360 |
| CUCAAAGAAA | AACCAAAAGA | AACACAAACC | GCCGCCCACA | GGACGUUAAG | UUCCGGGUG | 420 |
| GCGGUCAGAU | CGUUGGCGGA | GUUUACUUGC | UGCCGCGCAG | GGGCCCCAGG | UUGGGUGUGC | 480 |
| GCGCGACAAG | GAAGACUUCY | GAGCGAUCCC | AGCCGCGUGG | ACGACGCCAG | CCCAUCCCGA | 540 |
| AAGAUCGGCG | CUCCACCGGC | AAGUCCUGGG | GAAAGCCAGG | AUAUCCUUGG | CCCCUGUACG | 600 |
| GAAACGAGGG | UUGCGGCUGG | GCGGGUUGGC | UCCUGUCCCC | CGCGGGUCU | CGUCCUACUU | 660 |
| GGGGCCCCAC | CGACCCCCGG | CAUAGAUCAC | GCAAUUUGGG | CAGAGUCAUC | GAUACCAUUA | 720 |
| CGUGUGGUUU | UGCCGACCUC | AUGGGGUACA | UCCUGUCGU | UGGCGCCCCG | GUYGGAGGCG | 780 |
| UCGCCAGAGC | UCUGGCACAC | GGUGUUAGGG | UCCUGGAGGA | CGGGAUAAAU | UACGCAACAG | 840 |
| GGAAUUUACC | CGGUUGCUCU | UUUUCUAUCU | UUUUGCUUGC | UCUUCUGUCA | UGCGUCACAR | 900 |
| UGCCAGUGUC | UGCAGUGGAA | GUCAGGAACA | UYAGUUCUAG | CUACUACGCC | ACUAAUGAUU | 960 |
| GCUCAAACAA | CAGCAUCACC | UGGCAGCUCA | CUGACGCAGU | UCUCCAUCUU | CCUGGAUGCG | 1020 |
| UCCCAUGUGA | GAAYGAUAAY | GGCACCUUGC | RUUGCUGGAU | ACAAGUAACA | CCCRACGUGG | 1080 |
| CUGUGAAACA | CCGCGGUGCG | CUCACUCGUA | GCCUGCGAAC | ACACGUCGAC | AUGAUCGUAA | 1140 |
| UGGCAGCUAC | GGCCUGCUCG | GCCUUGUAUG | UGGGAGAUGU | GUGCGGGGCC | GUGAUGAUYC | 1200 |
| UAUCGCAGGC | UUUCAUGGUA | UCACCACAAC | GCCACAACUU | CACCCAAGAG | UGCAACUGUU | 1260 |
| CCAUCUACCA | AGGUCACAUC | ACCGGCCAUC | GCAUGGCAUG | GGACAUGAUG | CURARCUGGU | 1320 |
| CUCCAACUCU | URCCAUGAUC | CUCGCCUACG | CYGCUCGYGU | UCCCGARCUG | GUCCUCGAAA | 1380 |
| UYAUYUUCGG | CGGCCAUUGG | GGUGUGGYGU | UYGGCUUGGS | CUAUUUCUCC | AUGCARGGAG | 1440 |
| CGUGGGCCAA | AGUCRUYGCC | AUCCUCCUUC | UUGUUGCGGG | AGUGGAUGCA | W CCACCUAUU | 1500 |
| CCASCGGYCA | GSAAGCGGGU | CGURCCGYCK | MKGGG W UCKC | URGCCUCUUU | AMUACUGGUG | 1560 |
| CCAAGCAGAA | CCUCYAUUUR | AUCAACACCA | AUGGCAGCUG | GCACAUAAAC | CGGACUGCCC | 1620 |
| UCAAUUGCAA | UGACAGCYUA | SAGACGGGUU | UCMUCGCUUC | CYUGKUUUAC | W MCCRCARGU | 1680 |
| UCAACAGCUC | UGGCUGCCCC | GAGCGCUUGU | CUUCCUGCCG | CGGGCUGGAC | GAYUUCGCA | 1740 |
| UCGGCUGGGG | AACCUUGGAA | UACGAAACCA | ACGUCACCAA | CGAUGRGGAC | AUGAGGCCGU | 1800 |
| ACUGCUGGCA | UUACCCCCCG | AGGCCUUGCG | GCAUCGUCCC | GGCUAGGACG | GUUUGCGGAC | 1860 |
| CGGUCUAUUG | YUUCACCCCU | AGCCCUGUUG | UCGUGGGCAC | CACUGACAAG | CAGGGCGUAC | 1920 |

| | | | | | |
|---|---|---|---|---|---|
| CCACCUACAC | CUGGGGRGAA | AACGAGACCG | AUGUCUUCCU | GCRAAAUAGC | ACAAGACCCC | 1980 |
| CGCGAGGAGC | UUGGUUCGGC | UGCACYUGGA | UGAACGGGAC | UGGGUUCACU | AAGACAUGCG | 2040 |
| GUGCACCACC | UUGCCGCAUU | AGGAAAGACU | ACAACAGCAC | UCUCGAUUUA | UUGUGCCCCA | 2100 |
| CAGACUGUUU | UAGGAAGCAC | CCAGAUGCUA | CCUAUCUUAA | GUGUGGAGCA | GGGCCUUGGU | 2160 |
| UAACUCCCAG | GUGCCUGGUA | GACUACCCUU | AUAGRYUGUG | GCAUUAUCCG | UGCACUGUAA | 2220 |
| ACUUCACCAU | CUUYAAGGCG | CGGAUGUAUG | UAGGAGGGGU | GGAGCAUCGA | UUCUCCGCAG | 2280 |
| CAUGCAACUU | CACGCGCGGA | GAUCGCUGCA | GACUGGAAGA | UAGGGAUAGG | GGYCAGCAGA | 2340 |
| GUCCACUGCU | GCAUUCCACU | ACUGAGUGGG | CGGUGYCCC | AUGCUCCUUC | UCUGACCUAC | 2400 |
| CAGCACUAUC | CACUGGCCUA | UUGCACCUCC | ACCAAAACAU | CGUGGACGUG | CAGUACCUYU | 2460 |
| ACGGACUUUC | UCCGGCUCUG | ACAAGAUACA | UCGUGAAGUG | GGAGUGGGUG | AUCCUCCUUU | 2520 |
| UCUUGUUGUU | GGCAGACGCC | AGGRUCUGUG | CAUGCCUUUG | GAUGCUCA W C | AUACUGGGCC | 2580 |
| AAGCCGAAGC | GGCGCUUGAG | AAGCUCAUCA | UCUUGCACUC | CGCUAGYGCU | GCUAGUGCCA | 2640 |
| AUGGUCCGCU | GUGGUUUUUC | AUCUUCUUUA | CAGCGGCCUG | GUACUUAAAG | GGCAGGGUGG | 2700 |
| UCCCCGUGGC | CACGUACUCU | GUBCUCGGCU | URUGGUCCUU | CCUCCUCCUA | GUCCUGGCYU | 2760 |
| UACCACAGCA | GGCUUAUGCC | UUGGACGCUG | CUGAACAAGG | GGAACUGGGG | CUGGCCAUAU | 2820 |
| UAGUAAUUAU | AUCCAUCUUU | ACUCUUACCC | CAGCAUACAA | GAUCCUCCUG | AGCCGUUCAG | 2880 |
| UGUGGUGGCU | GUCCUACAUG | CUGGUCUUGG | CCGAGGCCCA | GAUUCAGCAA | UGGGUUCCCC | 2940 |
| CCCUGGAGGU | CCGAGGGGGG | CGUGACGGGA | UCAUCUGGGU | GGCUGUCAUU | CUACACCCAC | 3000 |
| GCCUUGUGUU | UGAGGUCACG | AAAUGGUUGU | UAGCAAUCCU | GGGGCCUGCC | UACCUCCUUA | 3060 |
| RAGCGUCUCU | GCUACGGAUA | CCGUACUUUG | UGAGGGCCCA | CGCUUUGCUA | CGAGUGUGUA | 3120 |
| CCCUGGUGAA | ACACCUCGCR | GGGGCUAGGU | ACAUCCAGAU | GCUGUURAUC | ACCAUAGGCA | 3180 |
| GAUGGACCGG | CACUUACAUC | UACGACCACC | UCUCCCCUUU | AUCAACUUGG | GCGGCCCAGG | 3240 |
| GUUURCGGGA | CCUGGCAAUC | GCCGUGGAGC | CUGUGGUGUU | CAGCCCAAUG | GAGAAGAAGG | 3300 |
| UCAUUGUGUG | GGGGGCUGAG | ACAGUGGCGU | GGGAGACAU | CCUGCAUGGC | CUCCGGUCU | 3360 |
| CCGCGAGGCU | AGGUAGGGAR | GUUCUGCUCG | GCCCUGCCGA | CGGCUACACC | UCCAAGGGGU | 3420 |
| GGAAKCUCCU | AGCUCCCAUU | ACUGCUUACA | CUCAGCAAAC | UCGUGGUCUC | CUGGGUGCUA | 3480 |
| UCGUGGUCAG | CCUAACGGGC | CGCGACAAAA | AUGAGCAGGC | UGGGCAGGUC | CAGGUUCUGU | 3540 |
| CCUCCGUCAC | ACAAACUUUC | UUGGGGACAU | CCAUUUCGGG | CGUCCUCUGG | ACAGUAUAUC | 3600 |
| ACGGGGCUGG | UAAUAAGACC | UUGGCCGGCC | CCAAGGGACC | AGUCACUCAG | AUGUACACCA | 3660 |
| GCGCAGAAGG | GGACCUCGUG | GGAUGGCCUA | GUCCCCCGG | GACUAAGUCA | UUGGACCCCU | 3720 |
| GUACCUGCGG | GGCCGUAGAC | CUCUACCUGG | UCACCCGAAA | CGCUGAUGUC | AUUCCGGUCC | 3780 |
| GGAGGAAAGA | UGACCGACGG | GGUGCAUUAC | UCUCGCCAAG | GCCCCUCUCA | ACCCUCAAAG | 3840 |
| GAUCAUCCGG | AGGGCCCGUG | CUCUGCUC W A | GGGGACACGC | CGUGGGCUUG | UUCAGAGCGG | 3900 |
| CCGUGUGUGC | CAGGGGUGUA | GCCAAAUCUA | UUGACUUCAU | CCCCGUCGAA | UCACUCGAUR | 3960 |
| UCGCCACACG | GACGCCCAGU | UUCUCUGACA | ACAGUCGCC | GCCAGCUGUG | CCCCAGUCUU | 4020 |
| ACCAGGUGGG | UUACUUGCAC | GCACCAACAG | GCAGCGGAAA | GAGCACCAAG | GUCCCUGCCG | 4080 |
| CGUAUGCCAG | UCAGGGGUAU | AAAGUACUCG | UACUAAAUCC | CUCUGUCGCG | GCCACACUUG | 4140 |
| GUUUUGGGGC | CUACAUGUCC | AAAGCCCACG | GGAUCAACCC | UAAUAUCAGA | ACUGGAGUGC | 4200 |
| GGACCGUUAC | CACCGGGGAC | UCUAUCACUU | ACUCCACUUA | UGGCAAGUUU | AUCGCAGAUG | 4260 |
| GAGGCUGUGC | AGCCGGUGCC | UAUGACAUCA | UCAUAUGCGA | CGAAUGCCAU | UCAGUGGACG | 4320 |
| CUACUACCAU | CCUUGGCAUU | GGAACAGUCC | UUGACCAAGC | UGAGACCGCA | GGCGUCAGGC | 4380 |

```
UAGUGGUYUU  GGCCACAGCC  ACGCCUCCCG  GUACGGUGAC  AACUCCCCAC  AGUAACAUAG    4440
AGGAGGUGGC  CCUUGGUCAC  GAGGGCGAGA  UCCCUUUUUA  UGGCAAAGCU  AUUCCCCUAG    4500
CUUUCAUCAA  GGGGGGCAGA  CACUUGAUCU  UUUGCCAUUC  AAAGAAGAAG  UGCGACGAGC    4560
UCGCAGCGGC  CCUCCGGGGC  AYGGGUGUCA  AUGCCGUUGC  AUACUAUAGG  GGUCUCGACG    4620
UCUCCGUUAU  ACCAACUCAA  GGAGACGUGG  UGGUUGUCGC  CACUGAUGCC  CUAAUGACUG    4680
GGUACACCGG  CGACUUUGAC  UCYGUCAUCG  ACUGUAAUGU  UGCAGUCUCU  CAGAUUGUUG    4740
ACUUCAGCCU  AGACCCAACC  UUCACCAUCA  CCACUCAAAC  CGUCCCUCAG  GACGCUGUCU    4800
CCCGUAGUCA  ACGUAGAGGG  AGAACUGGGA  GGGGGCGAUU  GGGCRUUUAC  AGGUAUGUUU    4860
CGUCAGGYGA  RRGGCCGUCU  GGGAUGUUCG  ACAGCGUAGU  GCYCUGCGAG  UGCUAUGAUG    4920
CCGGGGCAGC  CUGGUACGAG  CUUACACCUG  CUGAGACUAC  GGUGAGACUC  CGGGCYUAUU    4980
UCAACACGCC  CGGUUUGCCC  GUAUGUCAAG  ACCACCUGGA  GUUCGGGAA   GCGGUCUUUA    5040
CAGGUCUCAC  W CACAUURAC  GCCCACUUCC  UCUCCAGAC   GAAGCAAGGA  GGAGAAAACU    5100
UUGCRUAUCU  AACGGCCUAC  CAGGCCACAG  UAUGCGCCAG  GGCAAAGGCC  CUCCUCCUU     5160
CGUGGGACGU  GAUGUGGAAG  UGUCUAACUA  GGCUCAAACC  UACACUGACU  GGUCCCACCC    5220
CCCUCCUGUA  CCGCUUGGGU  GCCGUGACCA  AUGAGGUYAC  CUUGACGCAC  CCCGUGACGA    5280
AAUACAUCGC  CACGUGCAUG  CAAGCUGACC  UYGAGAUCAU  GACAAGCUCA  UGGGUCCUGG    5340
CGGGGGGGGU  GCUAGCCGCC  GUGGCAGCUU  ACUGCCUGGC  GACUGGCUGC  AUUCCAUCA     5400
UUGGCCGCCU  ACACCUGAAU  GAUCGGGUGG  UUGUGRCCCC  YGACAAGGAR  AUCUUAUAUG    5460
AGGCCUUUGA  UGAGAUGGAA  GAAUGCGCCU  CCAAAGCCGC  CCUCAUUGAG  GAAGGGCAGC    5520
GGAUGGCGGA  GAUGCUCAAA  UCUAAGAUAC  AAGGCCUCCU  ACAACAGGCC  ACAAGGCAAG    5580
CUCAAGRCAU  RCAGCCAGCU  AUACAGUCAU  CAUGGCCCAA  GCUUGAACAA  UUUUGGGCCA    5640
AACACAUGUG  GAACUUCAUC  AGUGGUAUAC  AGUACCUAGC  AGGACUCUCC  ACCCUACCGG    5700
GAAAUCCUGC  AGURGCAUCA  AUGAUGGCUU  UUAGCGCCGC  GCUGACUAGC  CCACUACCCA    5760
CCAGCACCAC  CAUCCUCUUG  AACAUCAUGG  GAGGAUGCUU  GGCCUCYCAG  AUUGCCCCCC    5820
CUGCCGGAGC  CACYGGCUUC  GUUGUCAGUG  GUCUAGUGGG  GGCGGCCGUC  GGAAGCAUAG    5880
GCCUGGGUAA  GAUACUGGUG  GACGUUUUGG  CCGGGUACGG  CGCAGGCAUU  UCAGGGGCCC    5940
UCGUAGCUUU  UAAGAUCAUG  AGCGGCGAGA  AGCCCACGGU  AGAAGACGUU  GUGAAUCUCC    6000
UGCCUGCUAU  YCUGUCUCCU  GGUGCGYUGG  UAGUGGGAGU  CAUCUGUGCA  GCAAUYCUGC    6060
GCCGCCACGU  CGGUCAGGGA  GAGGGRGCGG  UCCAGUGGAU  GAACAGACUG  AUCGCCUUCG    6120
CCUCCAGGGG  AAACCACGUU  GCCCUACCC   ACUACGUGGU  GGAGUCUGAC  GCUUCACAGC    6180
GUGURACGCA  GGUGCUGAGU  UCACUUACAA  UUACCAGCUU  ACUUAGGAGA  CUACAUGCCU    6240
GGAUCACUGA  AGAUUGCCCA  RUCCCAUGCU  CGGGGUCUUG  GCUCCAGGAC  AUUUGGGAUU    6300
GGGUUUGUUC  CAUCCUCACA  GACUUYAAAA  ACUGGCUGUC  UUCAAAAUUA  CUCCCCAAGA    6360
UGCCCGGCAU  UCCCUUUAUC  UCUUGCCAGA  AGGGAUACAA  GGGUGUAUGG  GCUGGUACGG    6420
GUGUCAUGAC  YACUCGRURC  CCAUGUGGAG  CAAACAUCUC  GGGCCAUGUC  CGCAUGGGCA    6480
CCAUGAAAAU  AACAGGCCCG  AAGACUUGCU  UGAACCUGUG  GCAGGGACU   UUCCCCAUUA    6540
AUUGUUACAC  AGAAGGGCCY  UGCGUGCCAA  AACCCCCUCC  UAAUUACAAG  ACCGCAAUUU    6600
GGAGGGUGGC  AGCGUCGGAG  UACGUUGAGG  UCACACAGCA  UGGCUCUUUC  UCGUAUGUAA    6660
CRGGGUUAAC  CAGUGACAAC  CUUAAGGUYC  CUUGCCAGGU  ACCAGCUCCA  GAAUUUUUCU    6720
CUUGGGUGGA  CGGGGUGCAA  AUCCACCGAU  UCGCCCCCGU  W CCAGGUCCC  UUCUUUCGGG    6780
AUGAGGUAAC  GUUCACCGUA  GGCCUUAACU  CCUUCGUGGU  CGGCUCUCAG  CUCCCUUGCG    6840
```

```
AUCCUGAGCC GGACACCGAR GUACUGGCCU CYAUGUUGAC AGACCCGUCC CACAUCACCG      6900
CKGAGGCGGC AGCCAGGCGA UUGGCAAGGG GAUCUCCCCC YUCACAGGCU AGCUCCUCAG      6960
CGAGCCAGCU CUCUGCCCCG UCCUUGAAGG CUACCUGUAC CACCCAUAAG ACAGCAUAUG      7020
AUUGUGACAU GGUGGAUGCY AACCUUUUCA UGGGAGGMGA UGUGAYCCGG AUUGAGUCUG      7080
ACUCUAAGGU GAUCGUUCUA GACUCCCUCG AUUCCAUGAC UGAGGUAGAG GAUGAUCGUG      7140
AGCCUUCUGU ACCAUCAGAG UACCUGAUCA AGAGGAGAAA GUUCCCACCG GCGCUGCCUC      7200
CUUGGGCCCG UCCAGACUAC AAUCCUGUUU UGAUCGAGAC AUGGAAGAGG CCGGGCUAUG      7260
AACCACCCAC UGUCCUAGGC UGUGCCCUCC CCCCACACY UCAAACGCCA GUGCCUCCAC      7320
CUCGGAGGCG CCGCGCYAAA RUCCUGACCC AGGACRAUGU GGAGGGGRUC CUCAGGGAGA      7380
UGGCUGACAA AGURCUCAGC CCUCUCCAAG ACAACAAUGA CUCCGGUCAC UCCACUGGAG      7440
CGGAUACCGG AGGAGACAUC GUCCAGCAAC CCUCUGACGA GACUGCCGCU UCAGAAGCGG      7500
GGUCACUGUC CUCCAUGCCU CCCCUUGAGG GAGAGCCGGG AGACCCYGAC CUGGAGUUUG      7560
AACCAGUGGG AUCCGCUCCC CCUUCUGAGG GGAGUGUGA GGUCAUUGAU UCGGACUCUA      7620
AGUCGUGGUC CACAGUCUCU GAUCAAGAGG AUUCUGUUAU CUGCUGCUCU AUGUCAUACU      7680
CCUGGACGGG GGCCCUCAUA ACACCAUGUG GGCCCGAAGA GGAGAAGUUA CCGAUCAACC      7740
CUCUGAGUAA UUCGCUCAUG CGGUUCCAUA AYAAGGUGUA CUCCACAACC UCGAGGAGUG      7800
CCUCUCUGAG GGCAAAGAAG GUGACUUUUG ACAGGGUGCA GGUGCUGGAC GCACACUAUG      7860
ACUCAGUCUU GCAGGACGUU AAGCGGGCCG CCUCUAAGGU URGUGCGAGG CUCCUCACAG      7920
UAGAGGAAGC CUGCGCGCUG ACCCCGCCCC ACUCCGCCAA AUCGCGAUAC GGAUUUGGGG      7980
CAAAAGAGGU GCGCAGCUUA UCCAGGAGGG CCGUUAACCA CAUCCGGUCC GUGUGGGAGG      8040
ACCUCCUGGA AGACCAACRU ACCCCAAUUG ACACAACUAU CAUGGCUAAA AAUGAGGUGU      8100
UCUGCAUUGA UCCAACUAAR GGUGGGAAAA AGCCAGCUCG CCUCAUCGUA UACCCCGACC      8160
UUGGGGUCAG GGUGUGCGAA AAGAUGGCCC UCUAUGACAU CRCACAAAAG CUUCCCAAAG      8220
CGAUAAUGGG GCCAUCCUAU GGGUUCCAAU ACUCUCCGC AGAACGGGUC GAUUUCCUCC      8280
UCAAAGCUUG GGGAAGUAAG AAGGACCCAA UGGGGUUCUC GUAUGACACC CGCUGCUUUG      8340
ACUCAACCGU CACGGAGAGG GACAUAAGAA CAGAAGAAUC CAUAUAUCAG GCUUGUUCUC      8400
UGCCUCAAGA AGCCAGAACU GUCAUACACU CGCUCACUGA GAGACUUUAC GUAGGAGGGC      8460
CCAUGACAAA CAGCAAAGGG CAAUCCUGCG GCUACAGGCG UUGCCGCGCA AGCGGKGUUU      8520
UCACCACCAG CAUGGGGAAU ACCAUGACAU GUUACAUCAA AGCCCUUGCA GCGUGUAAGG      8580
CUGCRGGGAU CGUGGACCCU GUUAUGUUGG UGUGUGGAGA CGACCUGGUC GUCAUCUCAG      8640
AGAGCCAAGG UAACGAGGAG GACGAGCGAA ACCUGAGAGC UUUCACGGAG GCUAUGACCA      8700
GGUAUUCCGC CCCUCCCGGU GACCUUCCCA GACCGGAAUA UGACUUGGAG CUUAUAACAU      8760
CCUGCUCCUC AAACGUAUCG GUAGCGCUGG ACUCUCGGGG UCGCCGCCGG UACUUCCUAA      8820
CCAGAGACCC UACCACUCCA AUCACCCGAG CUGCUUGGGA AACAGUAAGA CACUCCCCUG      8880
UCAAUUCUUG GCUGGGCAAC AUCAUCCAGU ACGCCCCCAC AAUCUGGGUC GGAUGGUCA      8940
UAAUGACUCA CUUCUUCUCC AUACUAUUGG CCCAGGACAC UCUGAACCAA AAUCUCAAUU      9000
UUGAGAUGUA CGGGGCAGUA UACUCGGUCA AUCCAUUAGA CCUACCGGCC AUAAUUGAAA      9060
GGCUACAUGG GCUUGAAGCC UUUUCACUGC ACACAUACUC UCCCCACGAA CUCUCACGGG      9120
UGGCAGCAAC UCUCAGAAAA CUUGGAGCGC CUCCCCUUAG AGCGGGAAG AGUCGGGCGC      9180
GUGCCGUGAG AGCUUCACUC AUCGCCCAAG GAGCGAGGGC GGCCAUUUGU GGCCGCUACC      9240
UCUUCAACUG GGCGGUGAAA ACAAAGCUCA AACUCACUCC AUUGCCCGAG GCGAGCCGCC      9300
```

| | | | | | |
|---|---|---|---|---|---|
| UGGAUUUAUC | CGGGUGGUUC | ACCGUGGGCG | CCGGCGGGGG | CGACAUUUAU | CACAGCGUGU | 9360
| CGCAUGCYCG | ACCCCGCCUA | UUACUCCUUU | GCCUACUCCU | ACUUAGCGUA | GGAGUAGGCA | 9420
| UCUUUUUACU | CCCCGCUCGG | UAGAGCGGCA | AACYCUAGCU | ACACUCCAUA | GCUAGUUUCC | 9480
| GUUUUUUUUU | UUUUUUUUUU | UUUUUUUUUU | U | | | 9511

(2) INFORMATION FOR SEQ ID NO:7:

(i) SEQUENCE CHARACTERISTICS:
        (A) LENGTH: 9511 base pairs
        (B) TYPE: nucleic acid
        (C) STRANDEDNESS: single
        (D) TOPOLOGY: linear (xi) SEQUENCE DESCRIPTION: SEQ ID NO:7:

| | | | | | |
|---|---|---|---|---|---|
| GCCCGCCCCC | TGATGGGGGC | GACACTCCGC | CATGAATCAC | TCCCCTGTGA | GGAACTACTG | 60
| TCTTCACGCA | GAAAGCGTCT | AGCCATGGCG | TTAGTATGAG | TGTCGTACAG | CCTCCAGGCC | 120
| CCCCCCTCCC | GGGAGAGCCA | TAGTGGTCTG | CGGAACCGGT | GAGTACACCG | GAATTACCGG | 180
| AAAGACTGGG | TCCTTTCTTG | GATAAACCCA | CTCTATGTCC | GGTCATTTGG | GCACGCCCCC | 240
| GCAAGACTGC | TAGCCGAGTA | GCGTTGGGTT | GCGAAAGGCC | TTGTGGTACT | GCCTGATAGG | 300
| GTRCTTGCGA | GTGCCCCGGG | AGGTCTCGTA | GACCGTGCAT | CATGAGCACA | AATCCTAAAC | 360
| CTCAAAGAAA | AACCAAAAGA | AACACAAACC | GCCGCCCACA | GGACGTTAAG | TTCCCGGGTG | 420
| GCGGTCAGAT | CGTTGGCGGA | GTTTACTTGC | TGCCGCGCAG | GGGCCCCAGG | TTGGGTGTGC | 480
| GCGCGACAAG | GAAGACTTCY | GAGCGATCCC | AGCCGCGTGG | ACGACGCCAG | CCCATCCCGA | 540
| AGATCGGCG | CTCCACCGGC | AAGTCCTGGG | GAAAGCCAGG | ATATCCTTGG | CCCCTGTACG | 600
| GAAACGAGGG | TTGCGGCTGG | GCGGGTTGGC | TCCTGTCCCC | CCGCGGGTCT | CGTCCTACTT | 660
| GGGGCCCCAC | CGACCCCCGG | CATAGATCAC | GCAATTTGGG | CAGAGTCATC | GATACCATTA | 720
| CGTGTGGTTT | TGCCGACCTC | ATGGGGTACA | TCCCTGTCGT | TGGCGCCCCG | GTYGGAGGCG | 780
| TCGCCAGAGC | TCTGGCACAC | GGTGTTAGGG | TCCTGGAGGA | CGGGATAAAT | TACGCAACAG | 840
| GGAATTTACC | CGGTTGCTCT | TTTTCTATCT | TTTTGCTTGC | TCTTCTGTCA | TGCGTCACAR | 900
| TGCCAGTGTC | TGCAGTGGAA | GTCAGGAACA | TYAGTTCTAG | CTACTACGCC | ACTAATGATT | 960
| GCTCAAACAA | CAGCATCACC | TGGCAGCTCA | CTGACGCAGT | TCTCCATCTT | CCTGGATGCG | 1020
| TCCCATGTGA | GAAYGATAAY | GGCACCTTGC | RTTGCTGGAT | ACAAGTAACA | CCCRACGTGG | 1080
| CTGTGAAACA | CCGCGGTGCG | CTCACTCGTA | GCCTGCGAAC | ACACGTCGAC | ATGATCGTAA | 1140
| TGGCAGCTAC | GGCCTGCTCG | GCCTTGTATG | TGGGAGATGT | GTGCGGGGCC | GTGATGATYC | 1200
| TATCGCAGGC | TTTCATGGTA | TCACCACAAC | GCCACAACTT | CACCCAAGAG | TGCAACTGTT | 1260
| CCATCTACCA | AGGTCACATC | ACCGGCCATC | GCATGGCATG | GGACATGATG | CTRARCTGGT | 1320
| CTCCAACTCT | TRCCATGATC | CTCGCCTACG | CYGCTCGYGT | TCCCGARCTG | GTCCTCGAAA | 1380
| TYATYTTCGG | CGGCCATTGG | GGTGTGGYGT | TYGGCTTGGS | CTATTCTCC | ATGCARGGAG | 1440
| CGTGGGCCAA | AGTCRTYGCC | ATCCTCCTTC | TTGTTGCGGG | AGTGGATGCA | W CCACCTATT | 1500
| CCASCGGYCA | GSAAGCGGGT | CGTRCCGYCK | MKGGG W TCKC | TRGCCTCTTT | AMTACTGGTG | 1560
| CCAAGCAGAA | CCTCYATTTR | ATCAACACCA | ATGGCAGCTG | GCACATAAAC | CGGACTGCCC | 1620
| TCAATTGCAA | TGACAGCYTA | SAGACGGGTT | TCMTCGCTTC | CYTGKTTTAC | W MCCRCARGT | 1680
| TCAACAGCTC | TGGCTGCCCC | GAGCGCTTGT | CTTCCTGCCG | CGGGCTGGAC | GAYTTYCGCA | 1740
| TCGGCTGGGG | AACCTTGGAA | TACGAAACCA | ACGTCACCAA | CGATGRGGAC | ATGAGGCCGT | 1800
| ACTGCTGGCA | TTACCCCCCG | AGGCCTTGCG | GCATCGTCCC | GGCTAGGACG | GTTTGCGGAC | 1860

```
CGGTCTATTG  YTTCACCCCT  AGCCCTGTTG  TCGTGGGCAC  CACTGACAAG  CAGGGCGTAC   1920
CCACCTACAC  CTGGGGRGAA  AACGAGACCG  ATGTCTTCCT  GCTRAATAGC  ACAAGACCCC   1980
CGCGAGGAGC  TTGGTTCGGC  TGCACYTGGA  TGAACGGGAC  TGGGTTCACT  AAGACATGCG   2040
GTGCACCACC  TTGCCGCATT  AGGAAAGACT  ACAACAGCAC  TCTCGATTTA  TTGTGCCCCA   2100
CAGACTGTTT  TAGGAAGCAC  CCAGATGCTA  CCTATCTTAA  GTGTGGAGCA  GGGCCTTGGT   2160
TAACTCCCAG  GTGCCTGGTA  GACTACCCTT  ATAGRYTGTG  GCATTATCCG  TGCACTGTAA   2220
ACTTCACCAT  CTTYAAGGCG  CGGATGTATG  TAGGAGGGGT  GGAGCATCGA  TTCTCCGCAG   2280
CATGCAACTT  CACGCGCGGA  GATCGCTGCA  GACTGGAAGA  TAGGGATAGG  GGYCAGCAGA   2340
GTCCACTGCT  GCATTCCACT  ACTGAGTGGG  CGGTGYTCCC  ATGCTCCTTC  TCTGACCTAC   2400
CAGCACTATC  CACTGGCCTA  TTGCACCTCC  ACCAAAACAT  CGTGGACGTG  CAGTACCTYT   2460
ACGGACTTTC  TCCGGCTCTG  ACAAGATACA  TCGTGAAGTG  GGAGTGGGTG  ATCCTCCTTT   2520
TCTTGTTGTT  GGCAGACGCC  AGGRTCTGTG  CATGCCTTTG  GATGCTCA W C  ATACTGGGCC   2580
AAGCCGAAGC  GGCGCTTGAG  AAGCTCATCA  TCTTGCACTC  CGCTAGYGCT  GCTAGTGCCA   2640
ATGGTCCGCT  GTGGTTTTTC  ATCTTCTTTA  CAGCGGCCTG  GTACTTAAAG  GGCAGGGTGG   2700
TCCCCGTGGC  CACGTACTCT  GTBCTCGGCT  TRTGGTCCTT  CCTCCTCCTA  GTCCTGGCYT   2760
TACCACAGCA  GGCTTATGCC  TTGGACGCTG  CTGAACAAGG  GGAACTGGGG  CTGGCCATAT   2820
TAGTAATTAT  ATCCATCTTT  ACTCTTACCC  CAGCATACAA  GATCCTCCTG  AGCCGTTCAG   2880
TGTGGTGGCT  GTCCTACATG  CTGGTCTTGG  CCGAGGCCCA  GATTCAGCAA  TGGGTTCCCC   2940
CCCTGGAGGT  CCGAGGGGGG  CGTGACGGGA  TCATCTGGGT  GGCTGTCATT  CTACACCCAC   3000
GCCTTGTGTT  TGAGGTCACG  AAATGGTTGT  TAGCAATCCT  GGGGCCTGCC  TACCTCCTTA   3060
RAGCGTCTCT  GCTACGGATA  CCGTACTTTG  TGAGGGCCCA  CGCTTTGCTA  CGAGTGTGTA   3120
CCCTGGTGAA  ACACCTCGCR  GGGGCTAGGT  ACATCCAGAT  GCTGTTRATC  ACCATAGGCA   3180
GATGGACCGG  CACTTACATC  TACGACCACC  TCTCCCCTTT  ATCAACTTGG  GCGGCCCAGG   3240
GTTTRCGGGA  CCTGGCAATC  GCCGTGGAGC  CTGTGGTGTT  CAGCCCAATG  GAGAAGAAGG   3300
TCATTGTGTG  GGGGGCTGAG  ACAGTGGCGT  GTGGAGACAT  CCTGCATGGC  CTCCCGGTCT   3360
CCGCGAGGCT  AGGTAGGGAR  GTTCTGCTCG  GCCCTGCCGA  CGGCTACACC  TCCAAGGGGT   3420
GGAAKCTCCT  AGCTCCCATT  ACTGCTTACA  CTCAGCAAAC  TCGTGGTCTC  CTGGGTGCTA   3480
TCGTGGTCAG  CCTAACGGGC  CGCGACAAAA  ATGAGCAGGC  TGGGCAGGTC  CAGGTTCTGT   3540
CCTCCGTCAC  ACAAACTTTC  TTGGGGACAT  CCATTTCGGG  CGTCCTCTGG  ACAGTATATC   3600
ACGGGGCTGG  TAATAAGACC  TTGGCCGGCC  CCAAGGGACC  AGTCACTCAG  ATGTACACCA   3660
GCGCAGAAGG  GGACCTCGTG  GGATGGCCTA  GTCCCCCCGG  GACTAAGTCA  TTGGACCCCT   3720
GTACCTGCGG  GGCCGTAGAC  CTCTACCTGG  TCACCCGAAA  CGCTGATGTC  ATTCCGGTCC   3780
GGAGGAAAGA  TGACCGACGG  GGTGCATTAC  TCTCGCCAAG  GCCCCTCTCA  ACCCTCAAAG   3840
GATCATCCGG  AGGGCCCGTG  CTCTGCTC W A  GGGGACACGC  CGTGGGCTTG  TTCAGAGCGG   3900
CCGTGTGTGC  CAGGGGTGTA  GCCAAATCTA  TTGACTTCAT  CCCCGTCGAA  TCACTCGATR   3960
TCGCCACACG  GACGCCCAGT  TTCTCTGACA  ACAGTRCGCC  GCCAGCTGTG  CCCCAGTCTT   4020
ACCAGGTGGG  TTACTTGCAC  GCACCAACAG  GCAGCGGAAA  GAGCACCAAG  GTCCCTGCCG   4080
CGTATGCCAG  TCAGGGGTAT  AAAGTACTCG  TACTAAATCC  CTCTGTCGCG  GCCACACTTG   4140
GTTTTGGGGC  CTACATGTCC  AAAGCCCACG  GGATCAACCC  TAATATCAGA  ACTGGAGTGC   4200
GGACCGTTAC  CACCGGGGAC  TCTATCACTT  ACTCCACTTA  TGGCAAGTTT  ATCGCAGATG   4260
GAGGCTGTGC  AGCCGGTGCC  TATGACATCA  TCATATGCGA  CGAATGCCAT  TCAGTGGACG   4320
```

```
CTACTACCAT CCTTGGCATT GGAACAGTCC TTGACCAAGC TGAGACCGCA GGCGTCAGGC     4380
TAGTGGTYTT GGCCACAGCC ACGCCTCCCG GTACGGTGAC AACTCCCCAC AGTAACATAG     4440
AGGAGGTGGC CCTTGGTCAC GAGGGCGAGA TCCCTTTTTA TGGCAAAGCT ATTCCCCTAG     4500
CTTTCATCAA GGGGGGCAGA CACTTGATCT TTTGCCATTC AAAGAAGAAG TGCGACGAGC     4560
TCGCAGCGGC CCTCCGGGGC AYGGGTGTCA ATGCCGTTGC ATACTATAGG GGTCTCGACG     4620
TCTCCGTTAT ACCAACTCAA GGAGACGTGG TGGTTGTCGC CACTGATGCC CTAATGACTG     4680
GGTACACCGG CGACTTTGAC TCYGTCATCG ACTGTAATGT TGCAGTCTCT CAGATTGTTG     4740
ACTTCAGCCT AGACCCAACC TTCACCATCA CCACTCAAAC CGTCCCTCAG GACGCTGTCT     4800
CCCGTAGTCA ACGTAGAGGG AGAACTGGGA GGGGGCGATT GGGCRTTTAC AGGTATGTTT     4860
CGTCAGGYGA RRGGCCGTCT GGGATGTTCG ACAGCGTAGT GCYCTGCGAG TGCTATGATG     4920
CCGGGGCAGC CTGGTACGAG CTTACACCTG CTGAGACTAC GGTGAGACTC CGGGCYTATT     4980
TCAACACGCC CGGTTTGCCC GTATGTCAAG ACCACCTGGA GTTCTGGGAA GCGGTCTTTA     5040
CAGGTCTCAC W CACATTRAC GCCCACTTCC TCTCCCAGAC GAAGCAAGGA GGAGAAAACT    5100
TTGCRTATCT AACGGCCTAC CAGGCCACAG TATGCGCCAG GGCAAAGGCC CCTCCTCCTT     5160
CGTGGGACGT GATGTGGAAG TGTCTAACTA GGCTCAAACC TACACTGACT GGTCCCACCC     5220
CCCTCCTGTA CCGCTTGGGT GCCGTGACCA ATGAGGTYAC CTTGACGCAC CCCGTGACGA     5280
AATACATCGC CACGTGCATG CAAGCTGACC TYGAGATCAT GACAAGCTCA TGGGTCCTGG     5340
CGGGGGGGGT GCTAGCCGCC GTGGCAGCTT ACTGCCTGGC GACTGGCTGC ATTTCCATCA     5400
TTGGCCGCCT ACACCTGAAT GATCGGGTGG TTGTGRCCCC YGACAAGGAR ATCTTATATG     5460
AGGCCTTTGA TGAGATGGAA GAATGCGCCT CCAAAGCCGC CCTCATTGAG GAAGGGCAGC     5520
GGATGGCGGA GATGCTCAAA TCTAAGATAC AAGGCCTCCT ACAACAGGCC ACAAGGCAAG     5580
CTCAAGRCAT RCAGCCAGCT ATACAGTCAT CATGGCCCAA GCTTGAACAA TTTTGGGCCA     5640
AACACATGTG GAACTTCATC AGTGGTATAC AGTACCTAGC AGGACTCTCC ACCCTACCGG     5700
GAAATCCTGC AGTRGCATCA ATGATGGCTT TTAGCGCCGC GCTGACTAGC CCACTACCCA     5760
CCAGCACCAC CATCCTCTTG AACATCATGG GAGGATGCTT GGCCTCYCAG ATTGCCCCCC     5820
CTGCCGGAGC CACYGGCTTC GTTGTCAGTG GTCTAGTGGG GGCGGCCGTC GGAAGCATAG     5880
GCCTGGGTAA GATACTGGTG GACGTTTTGG CCGGGTACGG CGCAGGCATT TCAGGGGCCC     5940
TCGTAGCTTT TAAGATCATG AGCGGCGAGA AGCCCACGGT AGAAGACGTT GTGAATCTCC     6000
TGCCTGCTAT YCTGTCTCCT GGTGCGYTGG TAGTGGGAGT CATCTGTGCA GCAATYCTGC     6060
GCCGCCACGT CGGTCAGGGA GAGGGRCGG TCCAGTGGAT AACAGACTG ATCGCCTTCG      6120
CCTCCAGGGG AAACCACGTT GCCCCTACCC ACTACGTGGT GGAGTCTGAC GCTTCACAGC     6180
GTGTRACGCA GGTGCTGAGT TCACTTACAA TTACCAGCTT ACTTAGGAGA CTACATGCCT     6240
GGATCACTGA AGATTGCCCA RTCCATGCT CGGGGTCTTG GCTCCAGGAC ATTTGGGATT      6300
GGGTTTGTTC CATCCTCACA GACTTYAAAA ACTGGCTGTC TTCAAAATTA CTCCCCAAGA     6360
TGCCCGGCAT TCCCTTTATC TCTTGCCAGA AGGGATACAA GGGTGTATGG GCTGGTACGG     6420
GTGTCATGAC YACTCGRTRC CCATGTGGAG CAAACATCTC GGGCCATGTC CGCATGGGCA     6480
CCATGAAAAT AACAGGCCCG AAGACTTGCT TGAACCTGTG GCAGGGGACT TTCCCCATTA     6540
ATTGTTACAC AGAAGGGCCY TGCGTGCCAA AACCCCCTCC TAATTACAAG ACCGCAATTT     6600
GGAGGGTGGC AGCGTCGGAG TACGTTGAGG TCACACAGCA TGGCTCTTTC TCGTATGTAA     6660
CRGGGTTAAC CAGTGACAAC CTTAAGGTYC CTTGCCAGGT ACCAGCTCCA GAATTTTTCT     6720
CTTGGGTGGA CGGGGTGCAA ATCCACCGAT TCGCCCCCGT W CCAGGTCCC TTCTTTCGGG   6780
```

```
ATGAGGTAAC GTTCACCGTA GGCCTTAACT CCTTCGTGGT CGGCTCTCAG CTCCCTTGCG    6840
ATCCTGAGCC GGACACCGAR GTACTGGCCT CYATGTTGAC AGACCCGTCC CACATCACCG    6900
CKGAGGCGGC AGCCAGGCGA TTGGCAAGGG GATCTCCCCC YTCACAGGCT AGCTCCTCAG    6960
CGAGCCAGCT CTCTGCCCCG TCCTTGAAGG CTACCTGTAC CACCCATAAG ACAGCATATG    7020
ATTGTGACAT GGTGGATGCY AACCTTTTCA TGGGAGGMGA TGTGAYCCGG ATTGAGTCTG    7080
ACTCTAAGGT GATCGTTCTA GACTCCCTCG ATTCCATGAC TGAGGTAGAG GATGATCGTG    7140
AGCCTTCTGT ACCATCAGAG TACCTGATCA AGAGGAGAAA GTTCCCACCG GCGCTGCCTC    7200
CTTGGGCCCG TCCAGACTAC AATCCTGTTT TGATCGAGAC ATGGAAGAGG CCGGGCTATG    7260
AACCACCCAC TGTCCTAGGC TGTGCCCTCC CCCCACACY TCAAACGCCA GTGCCTCCAC     7320
CTCGGAGGCG CCGCGCYAAA RTCCTGACCC AGGACRATGT GGAGGGGRTC CTCAGGAGA    7380
TGGCTGACAA AGTRCTCAGC CCTCTCCAAG ACAACAATGA CTCCGGTCAC TCCACTGGAG    7440
CGGATACCGG AGGAGACATC GTCCAGCAAC CCTCTGACGA GACTGCCGCT TCAGAAGCGG    7500
GGTCACTGTC CTCCATGCCT CCCCTTGAGG GAGAGCCGGG AGACCCYGAC CTGGAGTTTG    7560
AACCAGTGGG ATCCGCTCCC CCTTCTGAGG GGGAGTGTGA GGTCATTGAT TCGGACTCTA    7620
AGTCGTGGTC CACAGTCTCT GATCAAGAGG ATTCTGTTAT CTGCTGCTCT ATGTCATACT    7680
CCTGGACGGG GGCCCTCATA ACACCATGTG GGCCCGAAGA GGAGAAGTTA CCGATCAACC    7740
CTCTGAGTAA TTCGCTCATG CGGTTCCATA AYAAGGTGTA CTCCACAACC TCGAGGAGTG    7800
CCTCTCTGAG GGCAAAGAAG GTGACTTTTG ACAGGGTGCA GGTGCTGGAC GCACACTATG    7860
ACTCAGTCTT GCAGGACGTT AAGCGGGCCG CCTCTAAGGT TRGTGCGAGG CTCCTCACAG    7920
TAGAGGAAGC CTGCGCGCTG ACCCCGCCCC ACTCCGCCAA ATCGCGATAC GGATTTGGGG    7980
CAAAAGAGGT GCGCAGCTTA TCCAGGAGGG CCGTTAACCA CATCCGGTCC GTGTGGGAGG    8040
ACCTCCTGGA AGACCAACRT ACCCCAATTG ACACAACTAT CATGGCTAAA AATGAGGTGT    8100
TCTGCATTGA TCCAACTAAR GGTGGGAAAA AGCCAGCTCG CCTCATCGTA TACCCCGACC    8160
TTGGGGTCAG GGTGTGCGAA AAGATGGCCC TCTATGACAT CRCACAAAAG CTTCCCAAAG    8220
CGATAATGGG GCCATCCTAT GGGTTCCAAT ACTCTCCCGC AGAACGGGTC GATTTCCTCC    8280
TCAAAGCTTG GGGAAGTAAG AAGGACCCAA TGGGGTTCTC GTATGACACC CGCTGCTTTG    8340
ACTCAACCGT CACGGAGAGG GACATAAGAA CAGAAGAATC CATATATCAG GCTTGTTCTC    8400
TGCCTCAAGA AGCCAGAACT GTCATACACT CGCTCACTGA GAGACTTTAC GTAGGAGGGC    8460
CCATGACAAA CAGCAAGGG CAATCCTGCG GCTACAGGCG TTGCCGCGCA AGCGGKGTTT    8520
TCACCACCAG CATGGGGAAT ACCATGACAT GTTACATCAA AGCCCTTGCA GCGTGTAAGG    8580
CTGCRGGGAT CGTGGACCCT GTTATGTTGG TGTGTGGAGA CGACCTGGTC GTCATCTCAG    8640
AGAGCCAAGG TAACGAGGAG GACGAGCGAA ACCTGAGAGC TTTCACGGAG GCTATGACCA    8700
GGTATTCCGC CCCTCCCGGT GACCTTCCCA GACCGGAATA TGACTTGGAG CTTATAACAT    8760
CCTGCTCCTC AAACGTATCG GTAGCGCTGG ACTCTCGGGG TCGCCGCCGG TACTTCCTAA    8820
CCAGAGACCC TACCACTCCA ATCACCCGAG CTGCTTGGGA AACAGTAAGA CACTCCCCTG    8880
TCAATTCTTG GCTGGGCAAC ATCATCCAGT ACGCCCCCAC AATCTGGGTC GGATGGTCA     8940
TAATGACTCA CTTCTTCTCC ATACTATTGG CCCAGGACAC TCTGAACCAA AATCTCAATT    9000
TTGAGATGTA CGGGGCAGTA TACTCGGTCA ATCCATTAGA CCTACCGGCC ATAATTGAAA    9060
GGCTACATGG GCTTGAAGCC TTTTCACTGC ACACATACTC TCCCCACGAA CTCTCACGGG    9120
TGGCAGCAAC TCTCAGAAAA CTTGGAGCGC CTCCCCTTAG AGCGTGGAAG AGTCGGGCGC    9180
GTGCCGTGAG AGCTTCACTC ATCGCCCAAG GAGCGAGGGC GGCCATTTGT GGCCGCTACC    9240
```

-continued

```
TCTTCAACTG GGCGGTGAAA ACAAAGCTCA AACTCACTCC ATTGCCCGAG GCGAGCCGCC    9300

TGGATTTATC CGGGTGGTTC ACCGTGGGCG CCGGCGGGGG CGACATTTAT CACAGCGTGT    9360

CGCATGCYCG ACCCCGCCTA TTACTCCTTT GCCTACTCCT ACTTAGCGTA GGAGTAGGCA    9420

TCTTTTTACT CCCCGCTCGG TAGAGCGGCA AACYCTAGCT ACACTCCATA GCTAGTTTCC    9480

GTTTTTTTTT TTTTTTTTTT TTTTTTTTT T                                    9511
```

( 2 ) INFORMATION FOR SEQ ID NO:8:

( i ) SEQUENCE CHARACTERISTICS:
    ( A ) LENGTH: 3033 amino acids
    ( B ) TYPE: amino acid
    ( C ) STRANDEDNESS: unknown
    ( D ) TOPOLOGY: linear ( x i ) SEQUENCE DESCRIPTION: SEQ ID NO:8:

```
Met Ser Thr Asn Pro Lys Pro Gln Arg Lys Thr Lys Arg Asn Thr Asn
 1               5                  10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Asp Arg Arg Ser Thr Gly Lys Ser Trp Gly Lys Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Thr Trp Gly Pro Thr Asp Pro
            100                 105                 110

Arg His Arg Ser Arg Asn Leu Gly Arg Val Ile Asp Thr Ile Thr Cys
        115                 120                 125

Gly Phe Ala Asp Leu Met Gly Tyr Ile Pro Val Val Gly Ala Pro Val
    130                 135                 140

Gly Gly Val Ala Arg Ala Leu Ala His Gly Val Arg Val Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Val Thr Val Pro Val Ser Ala Val
            180                 185                 190

Glu Val Arg Asn Ile Ser Ser Tyr Tyr Ala Thr Asn Asp Cys Ser
        195                 200                 205

Asn Asn Ser Ile Thr Trp Gln Leu Thr Asp Ala Val Leu His Leu Pro
    210                 215                 220

Gly Cys Val Pro Cys Glu Asn Asp Asn Gly Thr Leu His Cys Trp Ile
225                 230                 235                 240

Gln Val Thr Pro Asn Val Ala Val Lys His Arg Gly Ala Leu Thr Arg
                245                 250                 255

Ser Leu Arg Thr His Val Asp Met Ile Val Met Ala Ala Thr Ala Cys
            260                 265                 270

Ser Ala Leu Tyr Val Gly Asp Val Cys Gly Ala Val Met Ile Leu Ser
        275                 280                 285

Gln Ala Phe Met Val Ser Pro Gln Arg His Asn Phe Thr Gln Glu Cys
    290                 295                 300

Asn Cys Ser Ile Tyr Gln Gly His Ile Thr Gly His Arg Met Ala Trp
305                 310                 315                 320

Asp Met Met Leu Ser Trp Ser Pro Thr Leu Thr Met Ile Leu Ala Tyr
```

|     |     |     |     |     | 325 |     |     |     | 330 |     |     |     | 335 |     |
| --- | --- | --- | --- | --- | --- | --- | --- | --- | --- | --- | --- | --- | --- | --- |
| Ala | Ala | Arg | Val | Pro | Glu | Leu | Val | Leu | Glu | Ile | Ile | Phe | Gly | Gly | His |
|     |     |     | 340 |     |     |     | 345 |     |     |     | 350 |     |     |
| Trp | Gly | Val | Val | Phe | Gly | Leu | Ala | Tyr | Phe | Ser | Met | Gln | Gly | Ala | Trp |
|     |     |     | 355 |     |     |     | 360 |     |     |     | 365 |     |     |
| Ala | Lys | Val | Ile | Ala | Ile | Leu | Leu | Leu | Val | Ala | Gly | Val | Asp | Ala | Thr |
|     | 370 |     |     |     |     | 375 |     |     |     |     | 380 |     |     |
| Thr | Tyr | Ser | Ser | Gly | Gln | Glu | Ala | Gly | Arg | Thr | Val | Ala | Gly | Phe | Ala |
| 385 |     |     |     |     | 390 |     |     |     |     | 395 |     |     |     |     | 400 |
| Gly | Leu | Phe | Thr | Thr | Gly | Ala | Lys | Gln | Asn | Leu | Tyr | Leu | Ile | Asn | Thr |
|     |     |     |     | 405 |     |     |     |     | 410 |     |     |     |     | 415 |
| Asn | Gly | Ser | Trp | His | Ile | Asn | Arg | Thr | Ala | Leu | Asn | Cys | Asn | Asp | Ser |
|     |     |     | 420 |     |     |     |     | 425 |     |     |     |     | 430 |     |
| Leu | Gln | Thr | Gly | Phe | Leu | Ala | Ser | Leu | Phe | Tyr | Thr | His | Lys | Phe | Asn |
|     |     |     | 435 |     |     |     |     | 440 |     |     |     |     | 445 |     |
| Ser | Ser | Gly | Cys | Pro | Glu | Arg | Leu | Ser | Ser | Cys | Arg | Gly | Leu | Asp | Asp |
|     |     | 450 |     |     |     |     |     | 455 |     |     |     |     | 460 |     |
| Phe | Arg | Ile | Gly | Trp | Gly | Thr | Leu | Glu | Tyr | Glu | Thr | Asn | Val | Thr | Asn |
| 465 |     |     |     |     | 470 |     |     |     |     | 475 |     |     |     |     | 480 |
| Asp | Gly | Asp | Met | Arg | Pro | Tyr | Cys | Trp | His | Tyr | Pro | Pro | Arg | Pro | Cys |
|     |     |     |     | 485 |     |     |     |     | 490 |     |     |     |     | 495 |
| Gly | Ile | Val | Pro | Ala | Arg | Thr | Val | Cys | Gly | Pro | Val | Tyr | Cys | Phe | Thr |
|     |     |     | 500 |     |     |     |     | 505 |     |     |     |     | 510 |     |
| Pro | Ser | Pro | Val | Val | Val | Gly | Thr | Thr | Asp | Lys | Gln | Gly | Val | Pro | Thr |
|     |     |     | 515 |     |     |     |     | 520 |     |     |     |     | 525 |     |
| Tyr | Thr | Trp | Gly | Glu | Asn | Glu | Thr | Asp | Val | Phe | Leu | Leu | Asn | Ser | Thr |
|     | 530 |     |     |     |     | 535 |     |     |     |     | 540 |     |     |     |
| Arg | Pro | Pro | Arg | Gly | Ala | Trp | Phe | Gly | Cys | Thr | Trp | Met | Asn | Gly | Thr |
| 545 |     |     |     |     | 550 |     |     |     |     | 555 |     |     |     |     | 560 |
| Gly | Phe | Thr | Lys | Thr | Cys | Gly | Ala | Pro | Pro | Cys | Arg | Ile | Arg | Lys | Asp |
|     |     |     |     | 565 |     |     |     |     | 570 |     |     |     |     | 575 |
| Tyr | Asn | Ser | Thr | Ile | Asp | Leu | Leu | Cys | Pro | Thr | Asp | Cys | Phe | Arg | Lys |
|     |     |     | 580 |     |     |     |     | 585 |     |     |     |     | 590 |     |
| His | Pro | Asp | Ala | Thr | Tyr | Leu | Lys | Cys | Gly | Ala | Gly | Pro | Trp | Leu | Thr |
|     |     | 595 |     |     |     |     |     | 600 |     |     |     |     | 605 |     |
| Pro | Arg | Cys | Leu | Val | Asp | Tyr | Pro | Tyr | Arg | Leu | Trp | His | Tyr | Pro | Cys |
|     | 610 |     |     |     |     | 615 |     |     |     |     | 620 |     |     |     |
| Thr | Val | Asn | Phe | Thr | Ile | Phe | Lys | Ala | Arg | Met | Tyr | Val | Gly | Gly | Val |
| 625 |     |     |     |     | 630 |     |     |     |     | 635 |     |     |     |     | 640 |
| Glu | His | Arg | Phe | Ser | Ala | Ala | Cys | Asn | Phe | Thr | Arg | Gly | Asp | Arg | Cys |
|     |     |     |     | 645 |     |     |     |     | 650 |     |     |     |     | 655 |
| Arg | Leu | Glu | Asp | Arg | Asp | Arg | Gly | Gln | Gln | Ser | Pro | Leu | Leu | His | Ser |
|     |     |     | 660 |     |     |     |     | 665 |     |     |     |     | 670 |     |
| Thr | Thr | Glu | Trp | Ala | Val | Leu | Pro | Cys | Ser | Phe | Ser | Asp | Leu | Pro | Ala |
|     |     |     | 675 |     |     |     |     | 680 |     |     |     |     | 685 |     |
| Leu | Ser | Thr | Gly | Leu | Leu | His | Leu | His | Gln | Asn | Ile | Val | Asp | Val | Gln |
|     | 690 |     |     |     |     | 695 |     |     |     |     | 700 |     |     |     |
| Tyr | Leu | Tyr | Gly | Leu | Ser | Pro | Ala | Leu | Thr | Arg | Tyr | Ile | Val | Lys | Trp |
| 705 |     |     |     |     | 710 |     |     |     |     | 715 |     |     |     |     | 720 |
| Glu | Trp | Val | Ile | Leu | Leu | Phe | Leu | Leu | Leu | Ala | Asp | Ala | Arg | Ile | Cys |
|     |     |     |     | 725 |     |     |     |     | 730 |     |     |     |     | 735 |
| Ala | Cys | Leu | Trp | Met | Leu | Ile | Ile | Leu | Gly | Gln | Ala | Glu | Ala | Ala | Leu |
|     |     |     | 740 |     |     |     |     | 745 |     |     |     |     | 750 |     |
| Glu | Lys | Leu | Ile | Ile | Leu | His | Ser | Ala | Ser | Ala | Ala | Ser | Ala | Asn | Gly |
|     |     |     | 755 |     |     |     |     | 760 |     |     |     |     | 765 |     |

```
Pro Leu Trp Phe Phe Ile Phe Phe Thr Ala Ala Trp Tyr Leu Lys Gly
    770             775             780
Arg Val Val Pro Val Ala Thr Tyr Ser Val Leu Gly Leu Trp Ser Phe
785             790             795             800
Leu Leu Leu Val Leu Ala Leu Pro Gln Gln Ala Tyr Ala Leu Asp Ala
            805             810             815
Ala Glu Gln Gly Glu Leu Gly Leu Ala Ile Leu Val Ile Ile Ser Ile
            820             825             830
Phe Thr Leu Thr Pro Ala Tyr Lys Ile Leu Leu Ser Arg Ser Val Trp
            835             840             845
Trp Leu Ser Tyr Met Leu Val Leu Ala Glu Ala Gln Ile Gln Gln Trp
850             855             860
Val Pro Pro Leu Glu Val Arg Gly Gly Arg Asp Gly Ile Ile Trp Val
865             870             875             880
Ala Val Ile Leu His Pro Arg Leu Val Phe Glu Val Thr Lys Trp Leu
            885             890             895
Leu Ala Ile Leu Gly Pro Ala Tyr Leu Leu Lys Ala Ser Leu Leu Arg
            900             905             910
Ile Pro Tyr Phe Val Arg Ala His Ala Leu Leu Arg Val Cys Thr Leu
        915             920             925
Val Lys His Leu Ala Gly Ala Arg Tyr Ile Gln Met Leu Leu Ile Thr
    930             935             940
Ile Gly Arg Trp Thr Gly Thr Tyr Ile Tyr Asp His Leu Ser Pro Leu
945             950             955             960
Ser Thr Trp Ala Ala Gln Gly Leu Arg Asp Leu Ala Ile Ala Val Glu
            965             970             975
Pro Val Val Phe Ser Pro Met Glu Lys Lys Val Ile Val Trp Gly Ala
            980             985             990
Glu Thr Val Ala Cys Gly Asp Ile Leu His Gly Leu Pro Val Ser Ala
        995             1000            1005
Arg Leu Gly Arg Glu Val Leu Leu Gly Pro Ala Asp Gly Tyr Thr Ser
    1010            1015            1020
Lys Gly Trp Lys Leu Leu Ala Pro Ile Thr Ala Tyr Thr Gln Gln Thr
1025            1030            1035            1040
Arg Gly Leu Leu Gly Ala Ile Val Val Ser Leu Thr Gly Arg Asp Lys
            1045            1050            1055
Asn Glu Gln Ala Gly Gln Val Gln Val Leu Ser Ser Val Thr Gln Thr
            1060            1065            1070
Phe Leu Gly Thr Ser Ile Ser Gly Val Leu Trp Thr Val Tyr His Gly
            1075            1080            1085
Ala Gly Asn Lys Thr Leu Ala Gly Pro Lys Gly Pro Val Thr Gln Met
    1090            1095            1100
Tyr Thr Ser Ala Glu Gly Asp Leu Val Gly Trp Pro Ser Pro Pro Gly
1105            1110            1115            1120
Thr Lys Ser Leu Asp Pro Cys Thr Cys Gly Ala Val Asp Leu Tyr Leu
            1125            1130            1135
Val Thr Arg Asn Ala Asp Val Ile Pro Val Arg Arg Lys Asp Asp Arg
            1140            1145            1150
Arg Gly Ala Leu Leu Ser Pro Arg Pro Leu Ser Thr Leu Lys Gly Ser
            1155            1160            1165
Ser Gly Gly Pro Val Leu Cys Ser Arg Gly His Ala Val Gly Leu Phe
            1170            1175            1180
Arg Ala Ala Val Cys Ala Arg Gly Val Ala Lys Ser Ile Asp Phe Ile
1185            1190            1195            1200
```

| | | | | | | | | | | | | | | |
|---|---|---|---|---|---|---|---|---|---|---|---|---|---|---|
|Pro|Val|Glu|Ser|Leu|Asp|Val|Ala|Thr|Arg|Thr|Pro|Ser|Phe|Ser|Asp|
| | | |1205| | | |1210| | | |1215| | | |

Pro Val Glu Ser Leu Asp Val Ala Thr Arg Thr Pro Ser Phe Ser Asp
                1205                 1210                1215

Asn Ser Thr Pro Pro Ala Val Pro Gln Ser Tyr Gln Val Gly Tyr Leu
            1220             1225             1230

His Ala Pro Thr Gly Ser Gly Lys Ser Thr Lys Val Pro Ala Ala Tyr
            1235             1240             1245

Ala Ser Gln Gly Tyr Lys Val Leu Val Leu Asn Pro Ser Val Ala Ala
            1250             1255             1260

Thr Leu Gly Phe Gly Ala Tyr Met Ser Lys Ala His Gly Ile Asn Pro
1265             1270             1275             1280

Asn Ile Arg Thr Gly Val Arg Thr Val Thr Thr Gly Asp Ser Ile Thr
            1285             1290             1295

Tyr Ser Thr Tyr Gly Lys Phe Ile Ala Asp Gly Gly Cys Ala Ala Gly
            1300             1305             1310

Ala Tyr Asp Ile Ile Ile Cys Asp Glu Cys His Ser Val Asp Ala Thr
            1315             1320             1325

Thr Ile Leu Gly Ile Gly Thr Val Leu Asp Gln Ala Glu Thr Ala Gly
            1330             1335             1340

Val Arg Leu Val Val Leu Ala Thr Ala Thr Pro Pro Gly Thr Val Thr
1345             1350             1355             1360

Thr Pro His Ser Asn Ile Glu Glu Val Ala Leu Gly His Glu Gly Glu
            1365             1370             1375

Ile Pro Phe Tyr Gly Lys Ala Ile Pro Leu Ala Phe Ile Lys Gly Gly
            1380             1385             1390

Arg His Leu Ile Phe Cys His Ser Lys Lys Lys Cys Asp Glu Leu Ala
            1395             1400             1405

Ala Ala Leu Arg Gly Met Gly Val Asn Ala Val Ala Tyr Tyr Arg Gly
1410             1415             1420

Leu Asp Val Ser Val Ile Pro Thr Gln Gly Asp Val Val Val Val Ala
1425             1430             1435             1440

Thr Asp Ala Leu Met Thr Gly Tyr Thr Gly Asp Phe Asp Ser Val Ile
            1445             1450             1455

Asp Cys Asn Val Ala Val Ser Gln Ile Val Asp Phe Ser Leu Asp Pro
            1460             1465             1470

Thr Phe Thr Ile Thr Thr Gln Thr Val Pro Gln Asp Ala Val Ser Arg
            1475             1480             1485

Ser Gln Arg Arg Gly Arg Thr Gly Arg Gly Arg Leu Gly Val Tyr Arg
            1490             1495             1500

Tyr Val Ser Ser Gly Glu Arg Pro Ser Gly Met Phe Asp Ser Val Val
1505             1510             1515             1520

Leu Cys Glu Cys Tyr Asp Ala Gly Ala Ala Trp Tyr Glu Leu Thr Pro
            1525             1530             1535

Ala Glu Thr Thr Val Arg Leu Arg Ala Tyr Phe Asn Thr Pro Gly Leu
            1540             1545             1550

Pro Val Cys Gln Asp His Leu Glu Phe Trp Glu Ala Val Phe Thr Gly
            1555             1560             1565

Leu Thr His Ile Asp Ala His Phe Leu Ser Gln Thr Lys Gln Gly Gly
            1570             1575             1580

Glu Asn Phe Ala Tyr Leu Thr Ala Tyr Gln Ala Thr Val Cys Ala Arg
1585             1590             1595             1600

Ala Lys Ala Pro Pro Pro Ser Trp Asp Val Met Trp Lys Cys Leu Thr
            1605             1610             1615

Arg Leu Lys Pro Thr Leu Thr Gly Pro Thr Pro Leu Leu Tyr Arg Leu
            1620             1625             1630

Gly Ala Val Thr Asn Glu Val Thr Leu Thr His Pro Val Thr Lys Tyr

|  | 1635 |  |  |  | 1640 |  |  |  | 1645 |  |  |
|---|---|---|---|---|---|---|---|---|---|---|---|

Ile Ala Thr Cys Met Gln Ala Asp Leu Glu Ile Met Thr Ser Ser Trp
                1650                    1655                    1660

Val Leu Ala Gly Gly Val Leu Ala Ala Val Ala Ala Tyr Cys Leu Ala
1665                    1670                    1675                    1680

Thr Gly Cys Ile Ser Ile Ile Gly Arg Leu His Leu Asn Asp Arg Val
                1685                    1690                    1695

Val Val Ala Pro Asp Lys Glu Ile Leu Tyr Glu Ala Phe Asp Glu Met
                1700                    1705                    1710

Glu Glu Cys Ala Ser Lys Ala Ala Leu Ile Glu Glu Gly Gln Arg Met
                1715                    1720                    1725

Ala Glu Met Leu Lys Ser Lys Ile Gln Gly Leu Leu Gln Gln Ala Thr
                1730                    1735                    1740

Arg Gln Ala Gln Asp Ile Gln Pro Ala Ile Gln Ser Ser Trp Pro Lys
1745                    1750                    1755                    1760

Leu Glu Gln Phe Trp Ala Lys His Met Trp Asn Phe Ile Ser Gly Ile
                1765                    1770                    1775

Gln Tyr Leu Ala Gly Leu Ser Thr Leu Pro Gly Asn Pro Ala Val Ala
                1780                    1785                    1790

Ser Met Met Ala Phe Ser Ala Ala Leu Thr Ser Pro Leu Pro Thr Ser
                1795                    1800                    1805

Thr Thr Ile Leu Leu Asn Ile Met Gly Gly Trp Leu Ala Ser Gln Ile
                1810                    1815                    1820

Ala Pro Pro Ala Gly Ala Thr Gly Phe Val Val Ser Gly Leu Val Gly
1825                    1830                    1835                    1840

Ala Ala Val Gly Ser Ile Gly Leu Gly Lys Ile Leu Val Asp Val Leu
                1845                    1850                    1855

Ala Gly Tyr Gly Ala Gly Ile Ser Gly Ala Leu Val Ala Phe Lys Ile
                1860                    1865                    1870

Met Ser Gly Glu Lys Pro Thr Val Glu Asp Val Val Asn Leu Leu Pro
                1875                    1880                    1885

Ala Ile Leu Ser Pro Gly Ala Leu Val Val Gly Val Ile Cys Ala Ala
                1890                    1895                    1900

Ile Leu Arg Arg His Val Gly Gln Gly Glu Gly Ala Val Gln Trp Met
1905                    1910                    1915                    1920

Asn Arg Leu Ile Ala Phe Ala Ser Arg Gly Asn His Val Ala Pro Thr
                1925                    1930                    1935

His Tyr Val Val Glu Ser Asp Ala Ser Gln Arg Val Thr Gln Val Leu
                1940                    1945                    1950

Ser Ser Leu Thr Ile Thr Ser Leu Leu Arg Arg Leu His Ala Trp Ile
                1955                    1960                    1965

Thr Glu Asp Cys Pro Val Pro Cys Ser Gly Ser Trp Leu Gln Asp Ile
                1970                    1975                    1980

Trp Asp Trp Val Cys Ser Ile Leu Thr Asp Phe Lys Asn Trp Leu Ser
1985                    1990                    1995                    2000

Ser Lys Leu Leu Pro Lys Met Pro Gly Ile Pro Phe Ile Ser Cys Gln
                2005                    2010                    2015

Lys Gly Tyr Lys Gly Val Trp Ala Gly Thr Gly Val Met Thr Thr Arg
                2020                    2025                    2030

Cys Pro Cys Gly Ala Asn Ile Ser Gly His Val Arg Met Gly Thr Met
                2035                    2040                    2045

Lys Ile Thr Gly Pro Lys Thr Cys Leu Asn Leu Trp Gln Gly Thr Phe
                2050                    2055                    2060

Pro Ile Asn Cys Tyr Thr Glu Gly Pro Cys Val Pro Lys Pro Pro Pro
2065                    2070                    2075                    2080

```
Asn Tyr Lys Thr Ala Ile Trp Arg Val Ala Ala Ser Glu Tyr Val Glu
            2085                2090                2095
Val Thr Gln His Gly Ser Phe Ser Tyr Val Thr Gly Leu Thr Ser Asp
            2100                2105                2110
Asn Leu Lys Val Pro Cys Gln Val Pro Ala Pro Glu Phe Phe Ser Trp
            2115                2120                2125
Val Asp Gly Val Gln Ile His Arg Phe Ala Pro Val Pro Gly Pro Phe
            2130                2135                2140
Phe Arg Asp Glu Val Thr Phe Thr Val Gly Leu Asn Ser Phe Val Val
2145                2150                2155                2160
Gly Ser Gln Leu Pro Cys Asp Pro Glu Pro Asp Thr Glu Val Leu Ala
            2165                2170                2175
Ser Met Leu Thr Asp Pro Ser His Ile Thr Ala Glu Ala Ala Ala Arg
            2180                2185                2190
Arg Leu Ala Arg Gly Ser Pro Pro Ser Gln Ala Ser Ser Ser Ala Ser
            2195                2200                2205
Gln Leu Ser Ala Pro Ser Leu Lys Ala Thr Cys Thr Thr His Lys Thr
            2210                2215                2220
Ala Tyr Asp Cys Asp Met Val Asp Ala Asn Leu Phe Met Gly Gly Asp
2225                2230                2235                2240
Val Thr Arg Ile Glu Ser Asp Ser Lys Val Ile Val Leu Asp Ser Leu
            2245                2250                2255
Asp Ser Met Thr Glu Val Glu Asp Asp Arg Glu Pro Ser Val Pro Ser
            2260                2265                2270
Glu Tyr Leu Ile Lys Arg Arg Lys Phe Pro Pro Ala Leu Pro Pro Trp
            2275                2280                2285
Ala Arg Pro Asp Tyr Asn Pro Val Leu Ile Glu Thr Trp Lys Arg Pro
2290                2295                2300
Gly Tyr Glu Pro Pro Thr Val Leu Gly Cys Ala Leu Pro Pro Thr Pro
2305                2310                2315                2320
Gln Thr Pro Val Pro Pro Pro Arg Arg Arg Arg Ala Lys Val Leu Thr
            2325                2330                2335
Gln Asp Asn Val Glu Gly Val Leu Arg Glu Met Ala Asp Lys Val Leu
            2340                2345                2350
Ser Pro Leu Gln Asp Asn Asn Asp Ser Gly His Ser Thr Gly Ala Asp
            2355                2360                2365
Thr Gly Gly Asp Ile Val Gln Gln Pro Ser Asp Glu Thr Ala Ala Ser
            2370                2375                2380
Glu Ala Gly Ser Leu Ser Ser Met Pro Pro Leu Glu Gly Glu Pro Gly
2385                2390                2395                2400
Asp Pro Asp Leu Glu Phe Glu Pro Val Gly Ser Ala Pro Pro Ser Glu
            2405                2410                2415
Gly Glu Cys Glu Val Ile Asp Ser Asp Ser Lys Ser Trp Ser Thr Val
            2420                2425                2430
Ser Asp Gln Glu Asp Ser Val Ile Cys Cys Ser Met Ser Tyr Ser Trp
            2435                2440                2445
Thr Gly Ala Leu Ile Thr Pro Cys Gly Pro Glu Glu Glu Lys Leu Pro
            2450                2455                2460
Ile Asn Pro Leu Ser Asn Ser Leu Met Arg Phe His Asn Lys Val Tyr
2465                2470                2475                2480
Ser Thr Thr Ser Arg Ser Ala Ser Leu Arg Ala Lys Lys Val Thr Phe
            2485                2490                2495
Asp Arg Val Gln Val Leu Asp Ala His Tyr Asp Ser Val Leu Gln Asp
            2500                2505                2510
```

Val Lys Arg Ala Ala Ser Lys Val Ser Ala Arg Leu Leu Thr Val Glu
2515                2520                     2525

Glu Ala Cys Ala Leu Thr Pro Pro His Ser Ala Lys Ser Arg Tyr Gly
2530                2535                     2540

Phe Gly Ala Lys Glu Val Arg Ser Leu Ser Arg Arg Ala Val Asn His
2545                2550                2555                2560

Ile Arg Ser Val Trp Glu Asn Leu Leu Glu Asp Gln His Thr Pro Ile
               2565                2570                2575

Asp Thr Thr Ile Met Ala Lys Asn Glu Val Phe Cys Ile Asp Pro Thr
              2580                2585                2590

Lys Gly Gly Lys Lys Pro Ala Arg Leu Ile Val Tyr Pro Asp Leu Gly
              2595                2600                2605

Val Arg Val Cys Glu Lys Met Ala Leu Tyr Asp Ile Ala Gln Lys Leu
2610                2615                2620

Pro Lys Ala Ile Met Gly Pro Ser Tyr Gly Phe Gln Tyr Ser Pro Ala
2625                2630                2635                2640

Glu Arg Val Asp Phe Leu Leu Lys Ala Trp Gly Ser Lys Lys Asp Pro
               2645                2650                2655

Met Gly Phe Ser Tyr Asp Thr Arg Cys Phe Asp Ser Thr Val Thr Glu
              2660                2665                2670

Arg Asp Ile Arg Thr Glu Glu Ser Ile Tyr Gln Ala Cys Ser Leu Pro
              2675                2680                2685

Gln Glu Ala Arg Thr Val Ile His Ser Leu Thr Glu Arg Leu Tyr Val
2690                2695                2700

Gly Gly Pro Met Thr Asn Ser Lys Gly Gln Ser Cys Gly Tyr Arg Arg
2705                2710                2715                2720

Cys Arg Ala Ser Gly Val Phe Thr Thr Ser Met Gly Asn Thr Met Thr
              2725                2730                2735

Cys Tyr Ile Lys Ala Leu Ala Ala Cys Lys Ala Ala Gly Ile Val Asp
              2740                2745                2750

Pro Val Met Leu Val Cys Gly Asp Asp Leu Val Val Ile Ser Glu Ser
              2755                2760                2765

Gln Gly Asn Glu Glu Asp Glu Arg Asn Leu Arg Ala Phe Thr Glu Ala
    2770                2775                2780

Met Thr Arg Tyr Ser Ala Pro Pro Gly Asp Leu Pro Arg Pro Glu Tyr
2785                2790                2795                2800

Asp Leu Glu Leu Ile Thr Ser Cys Ser Ser Asn Val Ser Val Ala Leu
              2805                2810                2815

Asp Ser Arg Gly Arg Arg Arg Tyr Phe Leu Thr Arg Asp Pro Thr Thr
              2820                2825                2830

Pro Ile Thr Arg Ala Ala Trp Glu Thr Val Arg His Ser Pro Val Asn
              2835                2840                2845

Ser Trp Leu Gly Asn Ile Ile Gln Tyr Ala Pro Thr Ile Trp Val Arg
              2850                2855                2860

Met Val Ile Met Thr His Phe Phe Ser Ile Leu Leu Ala Gln Asp Thr
2865                2870                2875                2880

Leu Asn Gln Asn Leu Asn Phe Glu Met Tyr Gly Ala Val Tyr Ser Val
              2885                2890                2895

Asn Pro Leu Asp Leu Pro Ala Ile Ile Glu Arg Leu His Gly Leu Glu
              2900                2905                2910

Ala Phe Ser Leu His Thr Tyr Ser Pro His Glu Leu Ser Arg Val Ala
              2915                2920                2925

Ala Thr Leu Arg Lys Leu Gly Ala Pro Pro Leu Arg Ala Trp Lys Ser
    2930                2935                2940

Arg Ala Arg Ala Val Arg Ala Ser Leu Ile Ala Gln Gly Ala Arg Ala

|      | 2945 |     |     | 2950 |     |     |     | 2955 |     |     |     | 2960 |     |
|------|------|-----|-----|------|-----|-----|-----|------|-----|-----|-----|------|-----|

Ala Ile Cys Gly Arg Tyr Leu Phe Asn Trp Ala Val Lys Thr Lys Leu
              2965                 2970               2975

Lys Leu Thr Pro Leu Pro Glu Ala Ser Arg Leu Asp Leu Ser Gly Trp
              2980                 2985               2990

Phe Thr Val Gly Ala Gly Gly Gly Asp Ile Tyr His Ser Val Ser His
              2995                 3000               3005

Ala Arg Pro Arg Leu Leu Leu Cys Leu Leu Leu Leu Ser Val Gly
    3010                 3015                 3020

Val Gly Ile Phe Leu Leu Pro Ala Arg
3025                3030

( 2 ) INFORMATION FOR SEQ ID NO:9:

( i ) SEQUENCE CHARACTERISTICS:
        ( A ) LENGTH: 3033 amino acids
        ( B ) TYPE: amino acid
        ( C ) STRANDEDNESS: unknown
        ( D ) TOPOLOGY: linear ( x i ) SEQUENCE DESCRIPTION: SEQ ID NO:9:

Met Ser Thr Asn Pro Lys Pro Gln Arg Lys Thr Lys Arg Asn Thr Asn
1                 5                     10                   15

Arg Arg Pro Gln Asp Val Lys Phe Pro Gly Gly Gly Gln Ile Val Gly
              20                   25                   30

Gly Val Tyr Leu Leu Pro Arg Arg Gly Pro Arg Leu Gly Val Arg Ala
            35                 40                  45

Thr Arg Lys Thr Ser Glu Arg Ser Gln Pro Arg Gly Arg Arg Gln Pro
   50                   55                 60

Ile Pro Lys Asp Arg Arg Ser Thr Gly Lys Ser Trp Gly Lys Pro Gly
65               70                  75                  80

Tyr Pro Trp Pro Leu Tyr Gly Asn Glu Gly Cys Gly Trp Ala Gly Trp
                 85                   90                 95

Leu Leu Ser Pro Arg Gly Ser Arg Pro Thr Trp Gly Pro Thr Asp Pro
          100                  105               110

Arg His Arg Ser Arg Asn Leu Gly Arg Val Ile Asp Thr Ile Thr Cys
       115                  120               125

Gly Phe Ala Asp Leu Met Gly Tyr Ile Pro Val Val Gly Ala Pro Val
  130                   135                 140

Gly Gly Val Ala Arg Ala Leu Ala His Gly Val Arg Val Leu Glu Asp
145               150                  155                160

Gly Ile Asn Tyr Ala Thr Gly Asn Leu Pro Gly Cys Ser Phe Ser Ile
              165                 170               175

Phe Leu Leu Ala Leu Leu Ser Cys Val Thr Met Pro Val Ser Ala Val
          180                 185               190

Glu Val Arg Asn Ile Ser Ser Ser Tyr Tyr Ala Thr Asn Asp Cys Ser
       195                  200               205

Asn Asn Ser Ile Thr Trp Gln Leu Thr Asp Ala Val Leu His Leu Pro
  210                   215                 220

Gly Cys Val Pro Cys Glu Asn Asp Asn Gly Thr Leu Arg Cys Trp Ile
225               230                  235                240

Gln Val Thr Pro Asp Val Ala Val Lys His Arg Gly Ala Leu Thr Arg
              245                 250               255

Ser Leu Arg Thr His Val Asp Met Ile Val Met Ala Ala Thr Ala Cys
          260                 265               270

Ser Ala Leu Tyr Val Gly Asp Val Cys Gly Ala Val Met Ile Leu Ser
       275                  280               285

| | | | | | | | | | | | | | | |
|---|---|---|---|---|---|---|---|---|---|---|---|---|---|---|
| Gln | Ala | Phe | Met | Val | Ser | Pro | Gln | Arg | His | Asn | Phe | Thr | Gln | Glu | Cys |
| | 290 | | | | 295 | | | | | 300 | | | | | |
| Asn | Cys | Ser | Ile | Tyr | Gln | Gly | His | Ile | Thr | Gly | His | Arg | Met | Ala | Trp |
| 305 | | | | | 310 | | | | 315 | | | | | | 320 |
| Asp | Met | Met | Leu | Asn | Trp | Ser | Pro | Thr | Leu | Ala | Met | Ile | Leu | Ala | Tyr |
| | | | | 325 | | | | | 330 | | | | | 335 | |
| Ala | Ala | Arg | Val | Pro | Glu | Leu | Val | Leu | Glu | Ile | Ile | Phe | Gly | Gly | His |
| | | | 340 | | | | | 345 | | | | | 350 | | |
| Trp | Gly | Val | Ala | Phe | Gly | Leu | Gly | Tyr | Phe | Ser | Met | Gln | Gly | Ala | Trp |
| | | | 355 | | | | 360 | | | | | 365 | | | |
| Ala | Lys | Val | Val | Ala | Ile | Leu | Leu | Val | Ala | Gly | Val | Asp | Ala | Ser | |
| | 370 | | | | | 375 | | | | | 380 | | | | |
| Thr | Tyr | Ser | Thr | Gly | Gln | Gln | Ala | Gly | Arg | Ala | Ala | Tyr | Gly | Ile | Ser |
| 385 | | | | | 390 | | | | | 395 | | | | | 400 |
| Ser | Leu | Phe | Asn | Thr | Gly | Ala | Lys | Gln | Asn | Leu | His | Leu | Ile | Asn | Thr |
| | | | | 405 | | | | | 410 | | | | | 415 | |
| Asn | Gly | Ser | Trp | His | Ile | Asn | Arg | Thr | Ala | Leu | Asn | Cys | Asn | Asp | Ser |
| | | | | 420 | | | | | 425 | | | | | 430 | |
| Leu | Glu | Thr | Gly | Phe | Ile | Ala | Ser | Leu | Val | Tyr | Tyr | Arg | Arg | Phe | Asn |
| | | | | 435 | | | | | 440 | | | | 445 | | |
| Ser | Ser | Gly | Cys | Pro | Glu | Arg | Leu | Ser | Ser | Cys | Arg | Gly | Leu | Asp | Asp |
| | 450 | | | | | 455 | | | | | 460 | | | | |
| Phe | Arg | Ile | Gly | Trp | Gly | Thr | Leu | Glu | Tyr | Glu | Thr | Asn | Val | Thr | Asn |
| 465 | | | | | 470 | | | | | 475 | | | | | 480 |
| Asp | Glu | Asp | Met | Arg | Pro | Tyr | Cys | Trp | His | Tyr | Pro | Pro | Arg | Pro | Cys |
| | | | | 485 | | | | | 490 | | | | | 495 | |
| Gly | Ile | Val | Pro | Ala | Arg | Thr | Val | Cys | Gly | Pro | Val | Tyr | Cys | Phe | Thr |
| | | | 500 | | | | | 505 | | | | | 510 | | |
| Pro | Ser | Pro | Val | Val | Val | Gly | Thr | Thr | Asp | Lys | Gln | Gly | Val | Pro | Thr |
| | | | 515 | | | | | 520 | | | | | 525 | | |
| Tyr | Thr | Trp | Gly | Glu | Asn | Glu | Thr | Asp | Val | Phe | Leu | Leu | Asn | Ser | Thr |
| | 530 | | | | | 535 | | | | | 540 | | | | |
| Arg | Pro | Pro | Arg | Gly | Ala | Trp | Phe | Gly | Cys | Thr | Trp | Met | Asn | Gly | Thr |
| 545 | | | | | 550 | | | | | 555 | | | | | 560 |
| Gly | Phe | Thr | Lys | Thr | Cys | Gly | Ala | Pro | Pro | Cys | Arg | Ile | Arg | Lys | Asp |
| | | | | 565 | | | | | 570 | | | | | 575 | |
| Tyr | Asn | Ser | Thr | Ile | Asp | Leu | Leu | Cys | Pro | Thr | Asp | Cys | Phe | Arg | Lys |
| | | | 580 | | | | | 585 | | | | | 590 | | |
| His | Pro | Asp | Ala | Thr | Tyr | Leu | Lys | Cys | Gly | Ala | Gly | Pro | Trp | Leu | Thr |
| | | | 595 | | | | | 600 | | | | | 605 | | |
| Pro | Arg | Cys | Leu | Val | Asp | Tyr | Pro | Tyr | Arg | Leu | Trp | His | Tyr | Pro | Cys |
| | 610 | | | | | 615 | | | | | 620 | | | | |
| Thr | Val | Asn | Phe | Thr | Ile | Phe | Lys | Ala | Arg | Met | Tyr | Val | Gly | Gly | Val |
| 625 | | | | | 630 | | | | | 635 | | | | | 640 |
| Glu | His | Arg | Phe | Ser | Ala | Ala | Cys | Asn | Phe | Thr | Arg | Gly | Asp | Arg | Cys |
| | | | | 645 | | | | | 650 | | | | | 655 | |
| Arg | Leu | Glu | Asp | Arg | Asp | Arg | Gly | Gln | Gln | Ser | Pro | Leu | Leu | His | Ser |
| | | | 660 | | | | | 665 | | | | | 670 | | |
| Thr | Thr | Glu | Trp | Ala | Val | Phe | Pro | Cys | Ser | Phe | Ser | Asp | Leu | Pro | Ala |
| | | | 675 | | | | | 680 | | | | | 685 | | |
| Leu | Ser | Thr | Gly | Leu | Leu | His | Leu | His | Gln | Asn | Ile | Val | Asp | Val | Gln |
| | | | 690 | | | | | 695 | | | | | 700 | | |
| Tyr | Leu | Tyr | Gly | Leu | Ser | Pro | Ala | Leu | Thr | Arg | Tyr | Ile | Val | Lys | Trp |
| 705 | | | | | 710 | | | | | 715 | | | | | 720 |
| Glu | Trp | Val | Ile | Leu | Leu | Phe | Leu | Leu | Leu | Ala | Asp | Ala | Arg | Val | Cys |

-continued

|  |  |  |  |  | 725 |  |  |  | 730 |  |  |  | 735 |  |
|---|---|---|---|---|---|---|---|---|---|---|---|---|---|---|
| Ala | Cys | Leu | Trp 740 | Met | Leu | Asn | Ile | Leu 745 | Gly | Gln | Ala | Glu 750 | Ala | Leu |
| Glu | Lys | Leu 755 | Ile | Ile | Leu | His | Ser 760 | Ala | Ser | Ala | Ala | Ser 765 | Ala | Asn | Gly |
| Pro | Leu | Trp 770 | Phe | Phe | Ile | Phe 775 | Phe | Thr | Ala | Ala | Trp 780 | Tyr | Leu | Lys | Gly |
| Arg 785 | Val | Val | Pro | Val | Ala 790 | Thr | Tyr | Ser | Val | Leu 795 | Gly | Leu | Trp | Ser | Phe 800 |
| Leu | Leu | Leu | Val | Leu 805 | Ala | Leu | Pro | Gln | Gln 810 | Ala | Tyr | Ala | Leu | Asp 815 | Ala |
| Ala | Glu | Gln | Gly 820 | Glu | Leu | Gly | Leu | Ala 825 | Ile | Leu | Val | Ile 830 | Ile | Ser | Ile |
| Phe | Thr | Leu 835 | Thr | Pro | Ala | Tyr | Lys 840 | Ile | Leu | Leu | Ser | Arg 845 | Ser | Val | Trp |
| Trp | Leu 850 | Ser | Tyr | Met | Leu | Val 855 | Leu | Ala | Glu | Ala | Gln 860 | Ile | Gln | Gln | Trp |
| Val 865 | Pro | Pro | Leu | Glu | Val 870 | Arg | Gly | Gly | Arg | Asp 875 | Gly | Ile | Ile | Trp | Val 880 |
| Ala | Val | Ile | Leu | His 885 | Pro | Arg | Leu | Val | Phe 890 | Glu | Val | Thr | Lys | Trp 895 | Leu |
| Leu | Ala | Ile | Leu 900 | Gly | Pro | Ala | Tyr | Leu 905 | Leu | Arg | Ala | Ser | Leu 910 | Leu | Arg |
| Ile | Pro | Tyr 915 | Phe | Val | Arg | Ala | His 920 | Ala | Leu | Leu | Arg | Val 925 | Cys | Thr | Leu |
| Val | Lys 930 | His | Leu | Ala | Gly | Ala 935 | Arg | Tyr | Ile | Gln | Met 940 | Leu | Leu | Ile | Thr |
| Ile 945 | Gly | Arg | Trp | Thr | Gly 950 | Thr | Tyr | Ile | Tyr | Asp 955 | His | Leu | Ser | Pro | Leu 960 |
| Ser | Thr | Trp | Ala | Ala 965 | Gln | Gly | Leu | Arg | Asp 970 | Leu | Ala | Ile | Ala | Val 975 | Glu |
| Pro | Val | Val 980 | Phe | Ser | Pro | Met | Glu 985 | Lys | Lys | Val | Ile | Val 990 | Trp | Gly | Ala |
| Glu | Thr | Val 995 | Ala | Cys | Gly | Asp | Ile 1000 | Leu | His | Gly | Leu | Pro 1005 | Val | Ser | Ala |
| Arg | Leu 1010 | Gly | Arg | Glu | Val | Leu 1015 | Leu | Gly | Pro | Ala | Asp 1020 | Gly | Tyr | Thr | Ser |
| Lys 1025 | Gly | Trp | Asn | Leu | Leu 1030 | Ala | Pro | Ile | Thr | Ala 1035 | Tyr | Thr | Gln | Gln | Thr 1040 |
| Arg | Gly | Leu | Leu | Gly 1045 | Ala | Ile | Val | Val | Ser 1050 | Leu | Thr | Gly | Arg | Asp 1055 | Lys |
| Asn | Glu | Gln | Ala | Gly 1060 | Gln | Val | Gln | Val | Leu 1065 | Ser | Ser | Val | Thr 1070 | Gln | Thr |
| Phe | Leu | Gly | Thr 1075 | Ser | Ile | Ser | Gly 1080 | Val | Leu | Trp | Thr | Val 1085 | Tyr | His | Gly |
| Ala | Gly | Asn 1090 | Lys | Thr | Leu | Ala 1095 | Gly | Pro | Lys | Gly | Pro 1100 | Val | Thr | Gln | Met |
| Tyr 1105 | Thr | Ser | Ala | Glu | Gly 1110 | Asp | Leu | Val | Gly | Trp 1115 | Pro | Ser | Pro | Pro | Gly 1120 |
| Thr | Lys | Ser | Leu | Asp 1125 | Pro | Cys | Thr | Cys | Gly 1130 | Ala | Val | Asp | Leu | Tyr 1135 | Leu |
| Val | Thr | Arg | Asn | Ala 1140 | Asp | Val | Ile | Pro | Val 1145 | Arg | Arg | Lys | Asp 1150 | Asp | Arg |
| Arg | Gly | Ala | Leu | Leu 1155 | Ser | Pro | Arg | Pro | Leu 1160 | Ser | Thr | Leu | Lys 1165 | Gly | Ser |

```
Ser Gly Gly Pro Val Leu Cys Ser Arg Gly His Ala Val Gly Leu Phe
    1170                1175                1180
Arg Ala Ala Val Cys Ala Arg Gly Val Ala Lys Ser Ile Asp Phe Ile
1185                1190                1195                1200
Pro Val Glu Ser Leu Asp Ile Ala Thr Arg Thr Pro Ser Phe Ser Asp
                1205                1210                1215
Asn Ser Ala Pro Pro Ala Val Pro Gln Ser Tyr Gln Val Gly Tyr Leu
            1220                1225                1230
His Ala Pro Thr Gly Ser Gly Lys Ser Thr Lys Val Pro Ala Ala Tyr
            1235                1240                1245
Ala Ser Gln Gly Tyr Lys Val Leu Val Leu Asn Pro Ser Val Ala Ala
        1250                1255                1260
Thr Leu Gly Phe Gly Ala Tyr Met Ser Lys Ala His Gly Ile Asn Pro
1265                1270                1275                1280
Asn Ile Arg Thr Gly Val Arg Thr Val Thr Thr Gly Asp Ser Ile Thr
                1285                1290                1295
Tyr Ser Thr Tyr Gly Lys Phe Ile Ala Asp Gly Gly Cys Ala Ala Gly
                1300                1305                1310
Ala Tyr Asp Ile Ile Ile Cys Asp Glu Cys His Ser Val Asp Ala Thr
            1315                1320                1325
Thr Ile Leu Gly Ile Gly Thr Val Leu Asp Gln Ala Glu Thr Ala Gly
        1330                1335                1340
Val Arg Leu Val Val Leu Ala Thr Ala Thr Pro Pro Gly Thr Val Thr
1345                1350                1355                1360
Thr Pro His Ser Asn Ile Glu Glu Val Ala Leu Gly His Glu Gly Glu
                1365                1370                1375
Ile Pro Phe Tyr Gly Lys Ala Ile Pro Leu Ala Phe Ile Lys Gly Gly
            1380                1385                1390
Arg His Leu Ile Phe Cys His Ser Lys Lys Lys Cys Asp Glu Leu Ala
            1395                1400                1405
Ala Ala Leu Arg Gly Thr Gly Val Asn Ala Val Ala Tyr Tyr Arg Gly
        1410                1415                1420
Leu Asp Val Ser Val Ile Pro Thr Gln Gly Asp Val Val Val Val Ala
1425                1430                1435                1440
Thr Asp Ala Leu Met Thr Gly Tyr Thr Gly Asp Phe Asp Ser Val Ile
                1445                1450                1455
Asp Cys Asn Val Ala Val Ser Gln Ile Val Asp Phe Ser Leu Asp Pro
            1460                1465                1470
Thr Phe Thr Ile Thr Thr Gln Thr Val Pro Gln Asp Ala Val Ser Arg
        1475                1480                1485
Ser Gln Arg Arg Gly Arg Thr Gly Arg Gly Arg Leu Gly Ile Tyr Arg
    1490                1495                1500
Tyr Val Ser Ser Gly Glu Gly Pro Ser Gly Met Phe Asp Ser Val Val
1505                1510                1515                1520
Pro Cys Glu Cys Tyr Asp Ala Gly Ala Ala Trp Tyr Glu Leu Thr Pro
            1525                1530                1535
Ala Glu Thr Thr Val Arg Leu Arg Ala Tyr Phe Asn Thr Pro Gly Leu
            1540                1545                1550
Pro Val Cys Gln Asp His Leu Glu Phe Trp Glu Ala Val Phe Thr Gly
        1555                1560                1565
Leu Thr His Ile Asn Ala His Phe Leu Ser Gln Thr Lys Gln Gly Gly
    1570                1575                1580
Glu Asn Phe Ala Tyr Leu Thr Ala Tyr Gln Ala Thr Val Cys Ala Arg
1585                1590                1595                1600
```

```
Ala Lys Ala Pro Pro Pro Ser Trp Asp Val Met Trp Lys Cys Leu Thr
            1605                1610                1615
Arg Leu Lys Pro Thr Leu Thr Gly Pro Thr Pro Leu Leu Tyr Arg Leu
1620                    1625                1630
Gly Ala Val Thr Asn Glu Val Thr Leu Thr His Pro Val Thr Lys Tyr
            1635                1640                1645
Ile Ala Thr Cys Met Gln Ala Asp Leu Glu Ile Met Thr Ser Ser Trp
            1650                1655                1660
Val Leu Ala Gly Gly Val Leu Ala Ala Val Ala Ala Tyr Cys Leu Ala
1665                    1670                1675                1680
Thr Gly Cys Ile Ser Ile Ile Gly Arg Leu His Leu Asn Asp Arg Val
            1685                1690                1695
Val Val Thr Pro Asp Lys Glu Ile Leu Tyr Glu Ala Phe Asp Glu Met
            1700                1705                1710
Glu Glu Cys Ala Ser Lys Ala Ala Leu Ile Glu Glu Gly Gln Arg Met
            1715                1720                1725
Ala Glu Met Leu Lys Ser Lys Ile Gln Gly Leu Leu Gln Gln Ala Thr
            1730                1735                1740
Arg Gln Ala Gln Gly Met Gln Pro Ala Ile Gln Ser Ser Trp Pro Lys
1745                    1750                1755                1760
Leu Glu Gln Phe Trp Ala Lys His Met Trp Asn Phe Ile Ser Gly Ile
                1765                1770                1775
Gln Tyr Leu Ala Gly Leu Ser Thr Leu Pro Gly Asn Pro Ala Val Ala
            1780                1785                1790
Ser Met Met Ala Phe Ser Ala Ala Leu Thr Ser Pro Leu Pro Thr Ser
            1795                1800                1805
Thr Thr Ile Leu Leu Asn Ile Met Gly Gly Trp Leu Ala Ser Gln Ile
1810                    1815                1820
Ala Pro Pro Ala Gly Ala Thr Gly Phe Val Val Ser Gly Leu Val Gly
1825                    1830                1835                1840
Ala Ala Val Gly Ser Ile Gly Leu Gly Lys Ile Leu Val Asp Val Leu
            1845                1850                1855
Ala Gly Tyr Gly Ala Gly Ile Ser Gly Ala Leu Val Ala Phe Lys Ile
            1860                1865                1870
Met Ser Gly Glu Lys Pro Thr Val Glu Asp Val Val Asn Leu Leu Pro
            1875                1880                1885
Ala Ile Leu Ser Pro Gly Ala Leu Val Val Gly Val Ile Cys Ala Ala
            1890                1895                1900
Ile Leu Arg Arg His Val Gly Gln Gly Glu Gly Ala Val Gln Trp Met
1905                    1910                1915                1920
Asn Arg Leu Ile Ala Phe Ala Ser Arg Gly Asn His Val Ala Pro Thr
                1925                1930                1935
His Tyr Val Val Glu Ser Asp Ala Ser Gln Arg Val Thr Gln Val Leu
            1940                1945                1950
Ser Ser Leu Thr Ile Thr Ser Leu Leu Arg Arg Leu His Ala Trp Ile
            1955                1960                1965
Thr Glu Asp Cys Pro Ile Pro Cys Ser Gly Ser Trp Leu Gln Asp Ile
            1970                1975                1980
Trp Asp Trp Val Cys Ser Ile Leu Thr Asp Phe Lys Asn Trp Leu Ser
1985                    1990                1995                2000
Ser Lys Leu Leu Pro Lys Met Pro Gly Ile Pro Phe Ile Ser Cys Gln
                2005                2010                2015
Lys Gly Tyr Lys Gly Val Trp Ala Gly Thr Gly Val Met Thr Thr Arg
            2020                2025                2030
Tyr Pro Cys Gly Ala Asn Ile Ser Gly His Val Arg Met Gly Thr Met
```

```
                        2035                       2040                         2045
Lys  Ile  Thr  Gly  Pro  Lys  Thr  Cys  Leu  Asn  Leu  Trp  Gln  Gly  Thr  Phe
               2050                      2055                     2060

Pro  Ile  Asn  Cys  Tyr  Thr  Glu  Gly  Pro  Cys  Val  Pro  Lys  Pro  Pro  Pro
2065                     2070                     2075                     2080

Asn  Tyr  Lys  Thr  Ala  Ile  Trp  Arg  Val  Ala  Ala  Ser  Glu  Tyr  Val  Glu
                         2085                     2090                     2095

Val  Thr  Gln  His  Gly  Ser  Phe  Ser  Tyr  Val  Thr  Gly  Leu  Thr  Ser  Asp
               2100                      2105                     2110

Asn  Leu  Lys  Val  Pro  Cys  Gln  Val  Pro  Ala  Pro  Glu  Phe  Phe  Ser  Trp
               2115                      2120                     2125

Val  Asp  Gly  Val  Gln  Ile  His  Arg  Phe  Ala  Pro  Val  Pro  Gly  Pro  Phe
2130                     2135                     2140

Phe  Arg  Asp  Glu  Val  Thr  Phe  Thr  Val  Gly  Leu  Asn  Ser  Phe  Val  Val
2145                     2150                     2155                     2160

Gly  Ser  Gln  Leu  Pro  Cys  Asp  Pro  Glu  Pro  Asp  Thr  Glu  Val  Leu  Ala
                    2165                     2170                     2175

Ser  Met  Leu  Thr  Asp  Pro  Ser  His  Ile  Thr  Ala  Glu  Ala  Ala  Ala  Arg
               2180                      2185                     2190

Arg  Leu  Ala  Arg  Gly  Ser  Pro  Pro  Ser  Gln  Ala  Ser  Ser  Ser  Ala  Ser
               2195                      2200                     2205

Gln  Leu  Ser  Ala  Pro  Ser  Leu  Lys  Ala  Thr  Cys  Thr  Thr  His  Lys  Thr
               2210                      2215                     2220

Ala  Tyr  Asp  Cys  Asp  Met  Val  Asp  Ala  Asn  Leu  Phe  Met  Gly  Gly  Asp
2225                     2230                     2235                     2240

Val  Thr  Arg  Ile  Glu  Ser  Asp  Ser  Lys  Val  Ile  Val  Leu  Asp  Ser  Leu
                    2245                     2250                     2255

Asp  Ser  Met  Thr  Glu  Val  Glu  Asp  Asp  Arg  Glu  Pro  Ser  Val  Pro  Ser
               2260                      2265                     2270

Glu  Tyr  Leu  Ile  Lys  Arg  Arg  Lys  Phe  Pro  Pro  Ala  Leu  Pro  Pro  Trp
               2275                      2280                     2285

Ala  Arg  Pro  Asp  Tyr  Asn  Pro  Val  Leu  Ile  Glu  Thr  Trp  Lys  Arg  Pro
               2290                      2295                     2300

Gly  Tyr  Glu  Pro  Pro  Thr  Val  Leu  Gly  Cys  Ala  Leu  Pro  Pro  Thr  Leu
2305                     2310                     2315                     2320

Gln  Thr  Pro  Val  Pro  Pro  Arg  Arg  Arg  Arg  Ala  Lys  Ile  Leu  Thr
                    2325                     2330                     2335

Gln  Asp  Asp  Val  Glu  Gly  Ile  Leu  Arg  Glu  Met  Ala  Asp  Lys  Val  Leu
                    2340                     2345                     2350

Ser  Pro  Leu  Gln  Asp  Asn  Asn  Asp  Ser  Gly  His  Ser  Thr  Gly  Ala  Asp
               2355                      2360                     2365

Thr  Gly  Gly  Asp  Ile  Val  Gln  Gln  Pro  Ser  Asp  Glu  Thr  Ala  Ala  Ser
               2370                      2375                     2380

Glu  Ala  Gly  Ser  Leu  Ser  Ser  Met  Pro  Pro  Leu  Glu  Gly  Glu  Pro  Gly
2385                     2390                     2395                     2400

Asp  Pro  Asp  Leu  Glu  Phe  Glu  Pro  Val  Gly  Ser  Ala  Pro  Pro  Ser  Glu
                    2405                     2410                     2415

Gly  Glu  Cys  Glu  Val  Ile  Asp  Ser  Asp  Ser  Lys  Ser  Trp  Ser  Thr  Val
               2420                      2425                     2430

Ser  Asp  Gln  Glu  Asp  Ser  Val  Ile  Cys  Cys  Ser  Met  Ser  Tyr  Ser  Trp
               2435                      2440                     2445

Thr  Gly  Ala  Leu  Ile  Thr  Pro  Cys  Gly  Pro  Glu  Glu  Glu  Lys  Leu  Pro
               2450                      2455                     2460

Ile  Asn  Pro  Leu  Ser  Asn  Ser  Leu  Met  Arg  Phe  His  Asn  Lys  Val  Tyr
2465                     2470                     2475                     2480
```

```
Ser  Thr  Thr  Ser  Arg  Ser  Ala  Ser  Leu  Arg  Ala  Lys  Lys  Val  Thr  Phe
               2485                2490                     2495

Asp  Arg  Val  Gln  Val  Leu  Asp  Ala  His  Tyr  Asp  Ser  Val  Leu  Gln  Asp
               2500                2505                     2510

Val  Lys  Arg  Ala  Ala  Ser  Lys  Val  Gly  Ala  Arg  Leu  Leu  Thr  Val  Glu
               2515                2520                     2525

Glu  Ala  Cys  Ala  Leu  Thr  Pro  Pro  His  Ser  Ala  Lys  Ser  Arg  Tyr  Gly
          2530                2535                     2540

Phe  Gly  Ala  Lys  Glu  Val  Arg  Ser  Leu  Ser  Arg  Arg  Ala  Val  Asn  His
2545                2550                     2555                          2560

Ile  Arg  Ser  Val  Trp  Glu  Asn  Leu  Leu  Glu  Asp  Gln  Arg  Thr  Pro  Ile
               2565                2570                     2575

Asp  Thr  Thr  Ile  Met  Ala  Lys  Asn  Glu  Val  Phe  Cys  Ile  Asp  Pro  Thr
               2580                2585                     2590

Lys  Gly  Gly  Lys  Lys  Pro  Ala  Arg  Leu  Ile  Val  Tyr  Pro  Asp  Leu  Gly
               2595                2600                     2605

Val  Arg  Val  Cys  Glu  Lys  Met  Ala  Leu  Tyr  Asp  Ile  Thr  Gln  Lys  Leu
          2610                2615                     2620

Pro  Lys  Ala  Ile  Met  Gly  Pro  Ser  Tyr  Gly  Phe  Gln  Tyr  Ser  Pro  Ala
2625                2630                     2635                          2640

Glu  Arg  Val  Asp  Phe  Leu  Leu  Lys  Ala  Trp  Gly  Ser  Lys  Lys  Asp  Pro
               2645                2650                     2655

Met  Gly  Phe  Ser  Tyr  Asp  Thr  Arg  Cys  Phe  Asp  Ser  Thr  Val  Thr  Glu
               2660                2665                     2670

Arg  Asp  Ile  Arg  Thr  Glu  Glu  Ser  Ile  Tyr  Gln  Ala  Cys  Ser  Leu  Pro
               2675                2680                     2685

Gln  Glu  Ala  Arg  Thr  Val  Ile  His  Ser  Leu  Thr  Glu  Arg  Leu  Tyr  Val
          2690                2695                     2700

Gly  Gly  Pro  Met  Thr  Asn  Ser  Lys  Gly  Gln  Ser  Cys  Gly  Tyr  Arg  Arg
2705                2710                     2715                          2720

Cys  Arg  Ala  Ser  Gly  Val  Phe  Thr  Thr  Ser  Met  Gly  Asn  Thr  Met  Thr
               2725                2730                     2735

Cys  Tyr  Ile  Lys  Ala  Leu  Ala  Ala  Cys  Lys  Ala  Ala  Gly  Ile  Val  Asp
               2740                2745                     2750

Pro  Val  Met  Leu  Val  Cys  Gly  Asp  Asp  Leu  Val  Val  Ile  Ser  Glu  Ser
               2755                2760                     2765

Gln  Gly  Asn  Glu  Glu  Asp  Glu  Arg  Asn  Leu  Arg  Ala  Phe  Thr  Glu  Ala
          2770                2775                     2780

Met  Thr  Arg  Tyr  Ser  Ala  Pro  Pro  Gly  Asp  Leu  Pro  Arg  Pro  Glu  Tyr
2785                2790                     2795                          2800

Asp  Leu  Glu  Leu  Ile  Thr  Ser  Cys  Ser  Ser  Asn  Val  Ser  Val  Ala  Leu
               2805                2810                     2815

Asp  Ser  Arg  Gly  Arg  Arg  Arg  Tyr  Phe  Leu  Thr  Arg  Asp  Pro  Thr  Thr
               2820                2825                     2830

Pro  Ile  Thr  Arg  Ala  Ala  Trp  Glu  Thr  Val  Arg  His  Ser  Pro  Val  Asn
               2835                2840                     2845

Ser  Trp  Leu  Gly  Asn  Ile  Ile  Gln  Tyr  Ala  Pro  Thr  Ile  Trp  Val  Arg
2850                2855                     2860

Met  Val  Ile  Met  Thr  His  Phe  Phe  Ser  Ile  Leu  Leu  Ala  Gln  Asp  Thr
2865                2870                     2875                          2880

Leu  Asn  Gln  Asn  Leu  Asn  Phe  Glu  Met  Tyr  Gly  Ala  Val  Tyr  Ser  Val
               2885                2890                     2895

Asn  Pro  Leu  Asp  Leu  Pro  Ala  Ile  Ile  Glu  Arg  Leu  His  Gly  Leu  Glu
               2900                2905                     2910
```

```
Ala  Phe  Ser  Leu  His  Thr  Tyr  Ser  Pro  His  Glu  Leu  Ser  Arg  Val  Ala
          2915            2920                2925

Ala  Thr  Leu  Arg  Lys  Leu  Gly  Ala  Pro  Pro  Leu  Arg  Ala  Trp  Lys  Ser
     2930                2935                     2940

Arg  Ala  Arg  Ala  Val  Arg  Ala  Ser  Leu  Ile  Ala  Gln  Gly  Ala  Arg  Ala
2945                2950                     2955                          2960

Ala  Ile  Cys  Gly  Arg  Tyr  Leu  Phe  Asn  Trp  Ala  Val  Lys  Thr  Lys  Leu
                2965                     2970                          2975

Lys  Leu  Thr  Pro  Leu  Pro  Glu  Ala  Ser  Arg  Leu  Asp  Leu  Ser  Gly  Trp
          2980                     2985                     2990

Phe  Thr  Val  Gly  Ala  Gly  Gly  Asp  Ile  Tyr  His  Ser  Val  Ser  His
          2995                3000                     3005

Ala  Arg  Pro  Arg  Leu  Leu  Leu  Leu  Cys  Leu  Leu  Leu  Leu  Ser  Val  Gly
3010                     3015                     3020

Val  Gly  Ile  Phe  Leu  Leu  Pro  Ala  Arg
3025                3030
```

NON-A, NON-B, HEPATITIS VIRUS GENOME, POLYNUCLEOTIDES, POLYPEPTIDES, ANTIGEN, ANTIBODY AND DETECTION SYSTEMS

REFERENCE TO A RELATED APPLICATION

The present application is a continuation-in-part of our U.S. patient application Ser. No. 07/866,045, filed on Apr. 9, 1992, now abandoned, which is incorporated by reference in its entirety.

BACKGROUND OF THE INVENTION

The present invention concerns non-A, non-B hepatitis (hereinafter called NANB hepatitis) virus genome, polynucleotides, polypeptides, related antigen, antibody and detection systems for detecting NANB antigens or antibodies.

Viral hepatitis of which DNA and RNA of the causative viruses have been elucidated, and their diagnosis and even prevention in some have been established, are hepatitis A and hepatitis B. The general name NANB hepatitis was given to the other forms of vital hepatitis.

Post-transfusion hepatitis was remarkably reduced after introduction of diagnostic systems for screening hepatitis B in transfusion bloods. However, there are still an estimated 280,000 annual cases of post-transfusion hepatitis caused by NANB hepatitis in Japan.

NANB hepatitis viruses were recently named C,D and E according to their types, and scientists started a world wide effort to conduct research for the causative viruses and subsequent extermination of the causative viruses.

In 1988, Chiron Corp. claimed that they had succeeded in cloning RNA virus genome, which they termed hepatitis C virus (hereinafter called HCV), as the causative agent of NANB hepatitis and reported on its nucleotide sequence (British Patent 2,212,511 which is the equivalent of European Patent Application 0,318,216). HCV (C100-3) antibody detection systems based on the sequence are now being introduced for screening of transfusion bloods and for diagnosis of patients in Japan and in many other countries. The detection systems for the C100-3 antibody have proven their partial association with NANB hepatitis; however, they capture only about 70% of carriers and chronic hepatitis patients, or they fail to detect the antibody in acute phase infection, thus leaving problems yet to be solved even after development of the C100-3 antibody by Chiron Corp.

The course of NANB hepatitis is troublesome and most patients are considered to become carriers, then to develop chronic hepatitis. In addition, most patients with chronic hepatitis develop liver cirrhosis, then hepatocellular carcinoma. It is therefore very imperative to isolate the virus itself and to develop effective diagnostic reagents enabling earlier diagnosis.

The presence of a number of NANB hepatitis which cannot be diagnosed by Chiron's C100-3 antibody detection kits suggests a possibility of a difference in subtype between Chiron's HCV and Japanese NANB hepatitis virus.

In order to develop NANB hepatitis diagnostic kits of more specificity and to develop effective vaccines, it becomes an absolutely important task to analyze each subtype of NANB hepatitis causative virus at its genetic and corresponding amino acid level.

SUMMARY OF THE INVENTION

An object of the present invention is to provide the nucleotide sequence coding for the structural protein of NANB hepatitis virus and, with such information, to analyze amino acids of the protein to locate and provide polypeptides useful as antigen for establishment of detection systems for NANB virus, its related antigens and antibodies.

A further object of the present invention is to locate polynucleotides essential to treatment, prevention and diagnosis, and polypeptides effective as antigens, by isolating NANB hepatitis virus RNA from human and chimpanzee virus carriers, cloning the cDNA covering the whole structural gene of the virus to determine its nucleotide sequence, and studying the amino acid sequence of the cDNA. As a result, the inventors have determined the nucleotides of the whole genome of a strain of NANB virus called HC-J6 and a strain called HC-J8. NANB hepatitis virus genome of HC-J6 and HC-J8 differ from that of Chiron's HCV.

DETAILED DESCRIPTION OF THE INVENTION

Figure 1:
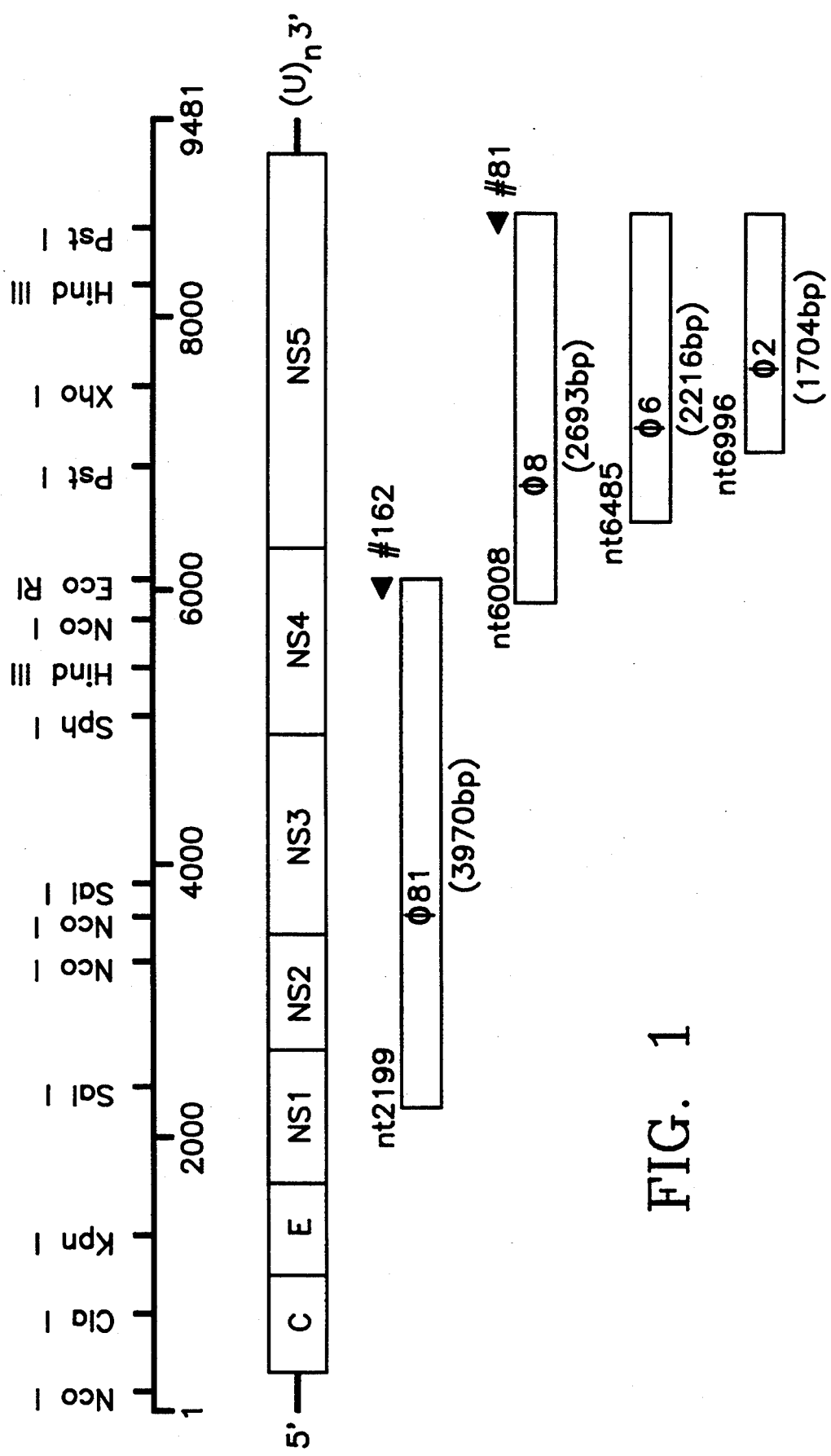
FIG. 1 shows the restriction map and structure of the coding region of NANB hepatitis virus genome (HC-J6) and positions of clones. C, E, NS-1, NS-2, NS-3, NS-4 and NS-5 are the abbreviation of core, envelope, non-structure-1, -2, -3, -4 and -5.

The present invention provides NANB hepatitis virus enome RNA for strain HC-J6 (sequence list 1) consisting of 340 nucleotides on the 5' terminus that follow an open reading frame consisting of 9099 nucleotides coding for the structural protein and non-structural protein that follow a noncoding region consisting of 150 nucleotides containing an U-stretch consisting of 108 uracils on the 3' terminus of NANB hepatitis virus, and NANB hepatitis virus genome having substantially the nucleotide sequence of sequence list 1.

The present invention provides polynucleotide N-9589 (strain HC-J6) comprising the DNA nucleotide sequence of sequence list 2; cDNA clone J6-φ81 comprising the nucleotide sequence of sequence list 3; cDNA clone J6-φ8 comprising the nucleotide sequence of sequence list 4; and NANB hepatitis virus polynucleotides having substantially the sequence of nucleotides of NANB hepatitis virus nucleotides shown in sequence lists 2 through 4.

The invention provides polypeptide coded for by genome or polynucleotide of HC-J6 above, polypeptide P-J6-3033, comprising the polypeptide sequence of sequence list 5, polypeptides produced by using recombinant genome, recombinant polynucleotides and recombinant cDNA of whole or a part of cDNA above, and polyclonal or monoclonal antibodies against the polypeptides described above.

The present invention also provides NANB hepatitis virus genome for strain HC-J8 comprising sequence list 6, NANB hepatitis virus RNA consisting of noncoding region consisting of 341 nucleotides on 5' terminus followed by an open reading frame consisting of 9099 nucleotides coding for the structural protein and nonstructural protein followed by a noncoding region consisting of 71 nucleotides containing an U-stretch consisting of 30 uracils on 3' terminus of NANB hepatitis virus comprising sequence list 6, and NANB hepatitis virus genome having substantially the nucleotide sequence of sequence list 6.

The present invention provides polynucleotide N-9511 for strain HC-J8 comprising the DNA nucleotide sequence of sequence list 7 and NANB hepatitis virus polynucleotide having substantially the sequence of nucleotides of NANB hepatitis virus nucleotides comprising sequence list 7.

The invention provides polypeptide coded for by genome or polynucleotide of HC-J8 above, polypeptide P-J8-3033, comprising the polypeptide sequence of sequence list 8 and polypeptide P-J8-3033-2 comprising the polypeptide sequence of sequence list 9, polypeptides produced by using recombinant genome, recombinant polynucleotides and recombinant cDNA of whole or a part of cDNA above, and polyclonal or monoclonal antibodies against the polypeptides described above.

The present invention, furthermore, provides NANB hepatitis diagnostic system using polypeptides or antibodies described above.

In the method described below, NANB hepatitis virus RNA of the present invention was obtained and its nucleotide sequence was determined.

Plasma samples (HC-J1, HC-J4, HC-J6 and HC-J8) were obtained from human and chimpanzee. HC-J1, HC-J6 and HC-J8 were obtained from Japanese blood donors who had tested positive for HCV antibody. HC-J4 was obtained from the chimpanzee subjected to the challenge test but was negative for Chiron's C100-3 antibody previously mentioned.

RNA was isolated from each of the plasma samples. Following the study of 5' terminus of approximately 2,500 nucleotides and 3' terminus of approximately 1,100 nucleotides disclosed in Japanese patent application No. 196175/91, the inventors have completed the study of the region coding for non-structural protein of strain HC-J6 and the study of the full length sequence of 9,589 nucleotides of HC-J6 genome RNA and have completed the study of the region coding for non-structural protein of strain HC-J8 and the study of the full length sequence of 9,589 nucleotides of HC-J8 genome RNA.

As described in the Example below, strain HC-J6 had a 5' noncoding region cons]sting of 340 nucleotides, and strain HC-J8 had a 5' noncoding region consisting of 341 nucleotides, followed by region coding for structural protein and region coding for non-structural protein.

Concerning the 3' terminus, strain HC-J6 was found to have a region consisting of 150 nucleotides containing an U-stretch consisting of 108 uracils following after the region coding for non-structural protein and strain HC-J8 was found to have a region consisting of 71 nucleotides containing an U-stretch consisting of 30 uracils following after the region coding for non-structural protein.

The coding region starting with adenine (341st nucleotide from the 5' terminus for strain HC-J6 and 342nd nucleotide from the 5' terminus for strain HC-J8) was found to have a long *Open Reading Frame* consisting of 9099 nucleotides which codes for 3033 amino acids. HCV or hepatitis C virus is supposed to be closely allied to flavivirus in regard to its genetic structure. The coding of the NANB hepatitis virus genome of the present invention was considered to be consisting of regions named C (core), E (envelope), NS-1 (non-structural-1), NS-2 (non-structural-2), NS-3 (non-structural-3), NS-4 (non-structural-4) and NS-5 (non-structural-5).

As compared with the sequence of HCV disclosed in the European Patent Application by Chiron Corp. (Publication No. 388,232), homology of sequences of the strain HC-J6 was 67.9% for the full nucleotide sequence and 72.3% for the full amino acid sequence, and homology of sequences of the strain HC-J8 was 66.4% for the full nucleotide sequence and 71.0% for the full amino acid sequence.

From an examination of homology for regions, the homology of nucleotide sequences (strain HC-J6) of the 5' terminal noncoding region was 94.4% and that of the amino acid sequences of the C region was 90.1%, showing comparatively high homology; on the other hand, concerning lower stream than envelope, homologies of amino acid sequence were found to be as low as 60.4% for E, 71.1% for NS-1, 57.8% for N8-2, 81.1% for NS-3, 73.1% for NS-4, and 69.9% for NS-5. As a result, HC-J6 strain was found to be significantly different from HCV strain found by Chiron Corp.

From an examination of homology for regions, the homology of nucleotide sequences (strain HC-J8) of the 5' terminal noncoding region was 93.8% and that of the amino acid sequences of the C region was 90.1%, showing comparatively high homology; on the other hand, concerning lower stream than envelope, homologies of amino acid sequence were found to be as low as 54.7% for E, 73.1% for NS-1, 55.6% for NS-2, 81o3% for NS-3, 72.1% for NS-4, 67.3% for NS-5, and 25.9% for 3' terminal noncoding region. As a result, HC-J8 strain was found to be significantly different from HCV strain found by Chiron Corp.

From the comparison of amino acid sequence of HC-J6 strain with strain HC-J1 (American type) and strain HC-J4 (Japanese type) disclosed by the inventors (Japan. J. Exp. Med. (1990), 60: 167–177), homology in the core region was more than 90% for each strain while that in the envelope region was 60.9% for HC-J1 and 53.1% for HC-J4. Thus, in the present invention, strain HC-J6 was found to be a different type of virus than strains HC-J1 or HC-J4.

From the comparison of amino acid sequence of HC-J8 strain with strain HC-J1 (type I) and strain HC-J4 (type II), homology of approximately 3,000 nucleotides of 5' terminus was 70.1% for HC-J1 and 67.1% for HC-J4, and from the comparison of all nucleotides with HC-J6 (type III) genome homology was as low as 76.9%. On the other hand, HC-J8 showed high homology with strain HC-J7 (type IV) disclosed in Japanese patent application 196175/91 as 93.1% for approximately 3,000 nucleotides of 5' terminus.

Nucleotides among stains assumed to belong to same type were supposed to show high homology. For example, homology of 95.6% for approximately 3,000 nucleotides of 5' terminus between HCV disclosed by Chiron Corp. and HC-J1 appears to show that they should be classified into type I. On the other hand, low homology of HC-J8 with HCV, HC-J1, HC-J4 and HC-J6 appeared to show that it was not to be classified into type I, II or III, but into type IV (the same as HC-J7).

Strain HC-J8 has some mutations in the nucleotides as shown in sequence lists 6 and 7 by symbols M, R, W, S, Y, K and B. It also can be easily understood that it has some mutations of amino acids from comparison of sequences in sequences lists 8 and 9. Mutation of nucleotides was observed up to approximately 1.4% in the whole genome and that of amino acids was observed up to approximately 1.7% in whole ORF. Thus the present invention includes genomes, polynucleotides and polypeptides of strain HC-J8 having some mutations.

In addition, envelope (E) region (576 nucleotides/192 amino acids of amino acids 192–383) and NS-1 region (1050 nucleotides/350 amino acids of amino acids 384–733) having many mutations in HC-J8 are called hyper-variable region since mutations were observed as 20 nucleotides/7 amino acids (3.47%/3.64%) in E region and 37 nucleotides/19 amino acids (3.52%/5.42%) in NS-1 region. According to these findings, the present invention can be recognized to include genomes and polypeptides coded for by the genomes of strain HC-J8 having mutations of 3.5% to 5.5% in those regions.

The genome, polynucleotide, and cDNA clones of the present invention can be used as material to produce peptides of the invention by integration into a host genome, e.g. *E. coli* or Bacillus, by means of known genetic engineering techniques.

Polypeptides of the invention are useful as material for diagnostic agents to detect NANB hepatitis antibodies with high specificity and as material to produce polyclonal and monoclonal antibodies by known techniques.

Polyclonal and monoclonal antibodies of the invention are useful as materials for diagnostic agents to detect NANB hepatitis antigens with high specificity.

A detection system using each polypeptide of the present invention or polypeptide with partial replacement of amino acids, and a detection system using monoclonal or polyclonal antibodies to such polypeptides, are useful as diagnostic agents of NANB hepatitis with high specificity and are effective to screen out NANB hepatitis virus from transfusion bloods or blood derivatives. The polypeptides, or antibodies to such polypeptides, can be used as a material for a vaccine against NANB hepatitis virus.

It is well known in the art that one or more nucleotides in a DNA sequence can be replaced by other nucleotides in order to produce the same protein. The present invention also concerns such nucleotide substitutions which yield DNA sequences which code for polypeptides as described above. It is also well known in the art that one or more amino acids in an amino acid sequence can be replaced by equivalent other amino acids, as demonstrated by U.S. Pat. No. 4,737,487 which is incorporated by reference, in order to produce an analog of the amino acid sequence. Any analogs of the polypeptides of the present invention involving amino acid deletions, amino acid replacements, such as replacements by other amino acids, or by isosteres (modified amino acids that bear close structural and spatial similarity to protein amino acids), amino acid additions, or isosteres additions can be utilized, so long as the sequences elicit antibodies recognizing NANB antigens.

Examples of application of this invention are shown below, however, the invention shall in no way be limited to those examples.

EXAMPLES

The 5' terminal nucleotide sequence and amino acid sequence of NANB hepatitis virus genome were determined in the following way:

(1) Isolation of RNA

RNA of the sample (HC-J1, HC-J6, HC-J8) from plasma of Japanese blood donor testing positive for HCV (C100-3) antibody (by Ortho HCV Ab ELISA, Ortho Diagnostic System, Tokyo), and that of the sample (HC-J4) from the chimpanzee challenged with NANB hepatitis for infectivity and negative for HCV antibody were isolated in the following method:

Each plasma sample was added with Tris chloride buffer (10 mM, pH 8.0) and centrifuged at $68 \times 10^3$ rpm for 1 hour. Its precipitate was suspended in Tris chloride buffer (50 mM, pH 8.0) containing 200 mM NaCl, 10 mM EDTA, 2% (w/v) sodium dodecyl sulfate (SDS), and proteinase K 1 mg/ml, incubated at 60° C. for 1 hour, then their nucleic acids were extracted by phenol/chloroform and precipitated by ethanol to obtain RNA.

(2) HC-J1 and HC-J8 cDNA Synthesis

After heating the RNA isolated from HC-J1 or HC-J8 plasma at 70° C. for 1 minute, this was used as a template; 10 units of reverse transcriptase (cDNA Synthesis System Plus, Amersham Japan) and 20 pmol of oligonucleotide primer (20 mer) were added and incubated at 42° C. for 1.5 hours to obtain cDNA. Primer #8 (5'-GATGCTTGCGGAAGCAATCA-3') was prepared by referring to the basic sequence shown in European Patent Application No. 88310922.5, which is relied on and incorporated herein by reference.

(3) cDNA Was Amplified by the following Polymerase Chain Reaction (PCR)

cDNA was amplified for 35 cycles according to Saiki's method (Science (1988) 239: 487–491) using Gene Amp DNA Amplifier Reagent (Perkin-Elmer.Cetus) on a DNA Thermal Cycler (Perkin-Elmer.Cetus).

Figure 2:
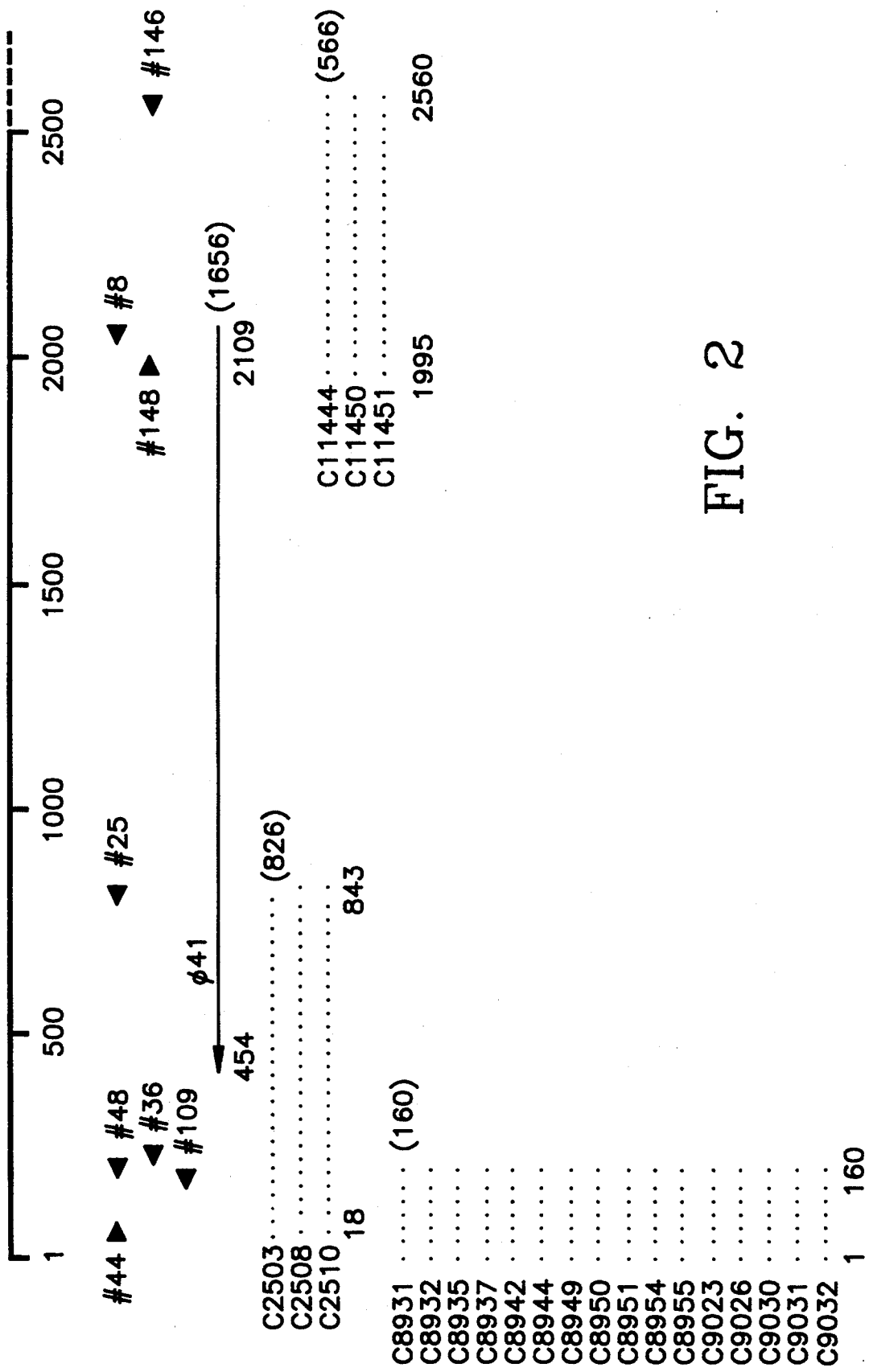
FIG. 2 shows the method of determination of the nucleotide sequence of 5' terminus of NANB hepatitis virus genome of strains HC-J1.
Figure 3:
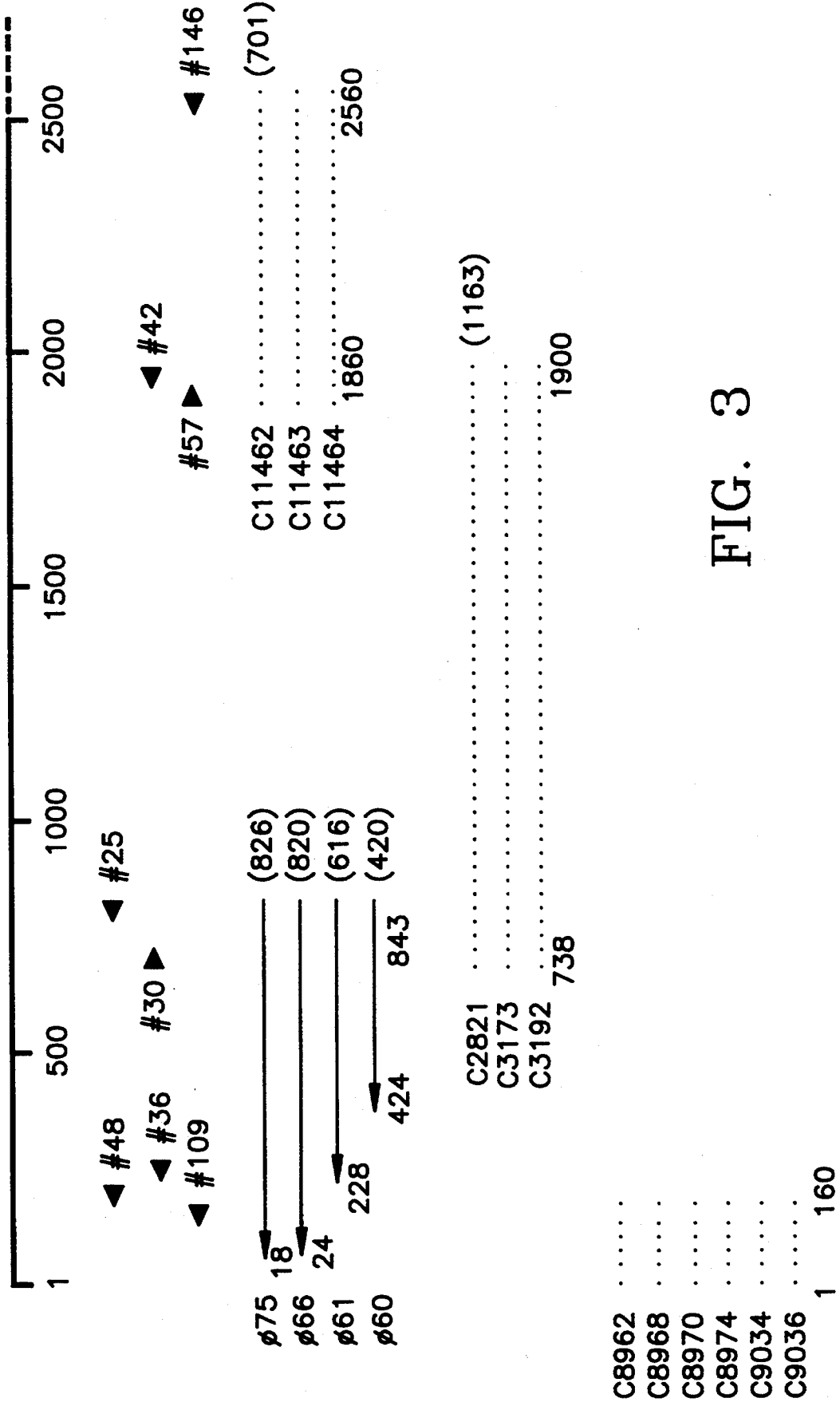
FIG. 3 shows the method of determination of the nucleotide sequence of the 5' terminus of NANB hepatitis virus strain HC-J4 genome.

For cDNA synthesis and for PCR for HC-J8, synthesized primers disclosed in Japanese patent application 153402/90 and those based on HC-J1, HC-J4 and HC-J6 genomes disclosed in Japanese patent applications 196175/91 and below were utilized, (4) Determination of 5' Terminal Nucleotide Sequence of HC-J1 and HC-J4 by Assembling cDNA Clones As shown in FIGS. 2 and 3, nucleotide sequences of 5' termini of the genomes of strains HC-J1 and HC-J4 were determined by combined analysis of clones obtained from the cDNA library constructed in bacteriophage λgt10 and clones obtained by amplification of HCV specific cDNA by PCR, FIGS. 2 and 3 show 5' termini of NANB hepatitis virus genome together with cleavage site by restriction endonuclease and sequence of primers used. In the figures, solid lines are nucleotide sequences determined by clones from bacteriophage λgt10 library while dotted lines show sequences determined by clones obtained by PCR.

A 1656 nucleotide sequence of HC-J1 spanning nt454–2109 was determined by clone φ41 which was obtained by inserting the cDNA synthesized with the primer #8 into λgt10 phage vector (Amersham).

Another primer #25 (5'-TCCCTGTTGCATAGTTCACG -3') corresponding to nt824–843 was synthesized based on the φ41 sequence, and four clones (φ60, φ61, φ66 and φ75) were obtained to cover the upstream sequence nt18–843.

(5) Determination of 5' Terminal Nucleotide Sequence of HC-J6.

Figure 4:
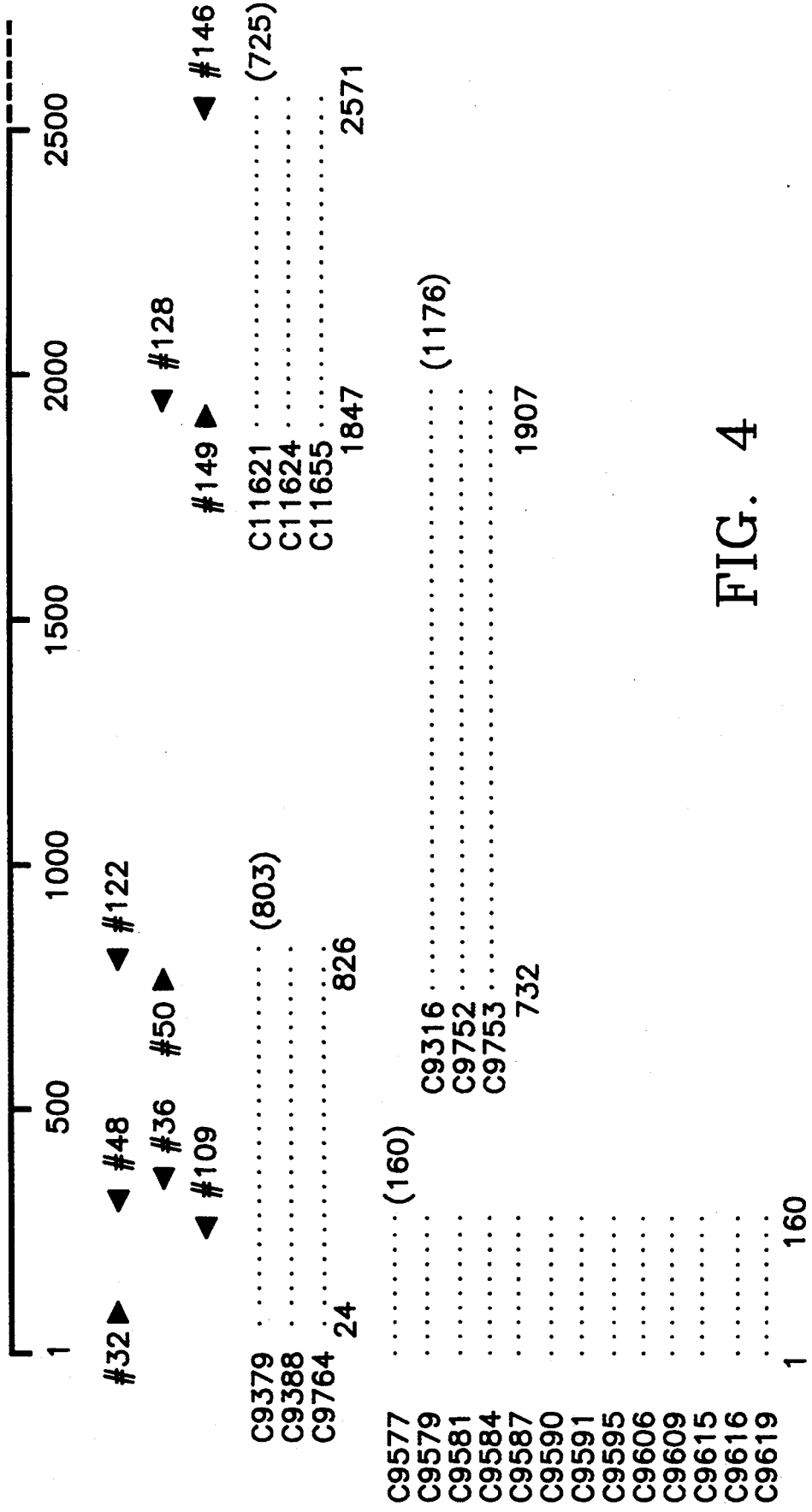
FIG. 4 shows the method of determination of the nucleotide sequence of the 5' terminus of NANB hepatitis virus strain HC-J6 genome.

The nucleotide sequence of the 5' terminus of strain HC-J6 was determined from analysis of clones obtained by PCR amplification as shown in FIG. 4.

Isolation of RNA from HC-J6 and determination of its sequence was made in the same manner as described in (2) above. Sequences in the range of nt24–2551 of the RNA were determined from consensus sequence of respective clones obtained by amplification by PCR using each pair of primers based on nucleotide sequence of HC-J4.

nt24–826
32 (5'-ACTCCACCATAGATCACTCC-3')
122 (5'-AGGTTCCCTGTTGCATAATT-3')
Clones: C9397, C9388, C9764
nt732–1907
50 (5'-GCCGACCTCATGGGGTACAT-3')
128 (5'-TCGGTCGTGCCCACTACCAC-3')
Clones: C9316, C9752, C9753
nt1847–2571
149 (5'-TCTGTGTGTGGCCCAGTGTA-3')
146 (5'-AGTAGCATCATCCACAAGCA-3')
Clones: C11621, C11624, C11655

In order to determine further upstream of the 5' terminus, antisense primer #36 (5'- AACACTACTCGGCTAGCAGT -3') corresponding to nt246–265, followed by dAs were added to 5'terminus of cDNA using terminal deoxynucleotidyl transferase, and one-sided PCR amplification was made twice as described below.

cDNA was amplified for 35 cycles as first stage PCR using oligo dT primer (20-mer) and antisense primer #48 (5'-GTTGATCCAAGAAAGGACCC -3') of nt188–207, followed by the second stage of PCR by 30 cycle amplification using the first PCR product as a template, oligo dT primer (20 -mer) and antisense primer #109 (21-mer; 5'-ACCGGATCCGCAGACCACTAT-3') corresponding to nt140 to 160. The obtained PCR product was subcloned to M13 phage vector.

Nucleotide sequence from nt1 to 23 was determined from consensus sequence of 13 isolated clones C9577, C9579, C9581, C9587, C9590, C9591, C9595, C9606, C9609, C9615, C9616 and C9619 obtained above which were considered having complete 5' terminus.

(6) Determination of nucelotide sequence of HC-J6 middle region cDNA library was constructed with using λgt10 according to the method described in (2) above from 100 ml of HC-J6 plasma as a starting materials. Primers #162 and #81 were prepared for synthesis by referring to the basic sequence shown in the European Patent Application Publication No, 318,216, Clones were selected by plaque hybridization.

Nucleotide sequence from 2552 to 8700 was determined from consensus sequence of four obtained cDNA clones φ2 (nt6996 to 8700), φ6(nt6485 to 8700), φ8(nt6008 to 8700) and φ81 (nt2199 to 6168) as shown in FIG. 1. Clones φ81 and φ8 were found to have nucleotide sequences shown in sequence lists 3 and 4 respectively.

(7) Determination of 3' terminal nucleotide sequence of HC-J6 strain

Figure 5:
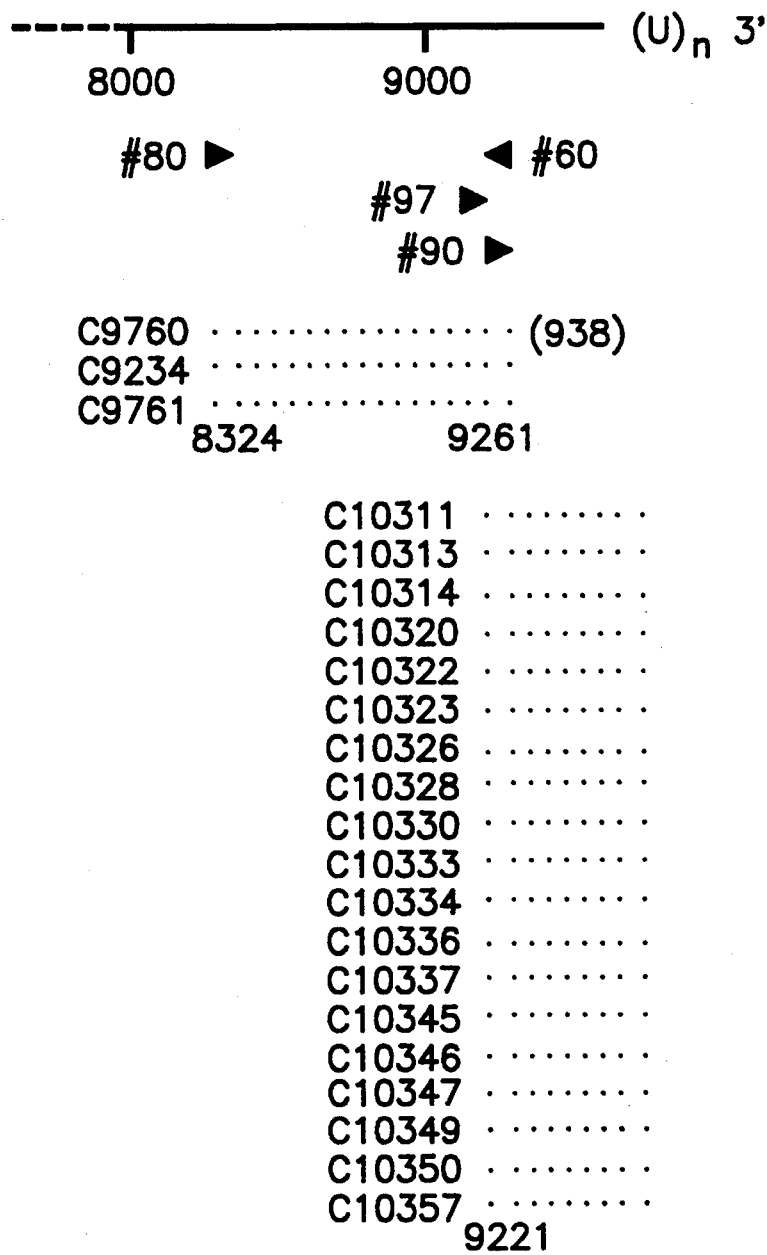
FIG. 5 shows the method of determination of the nucleotide sequence of 3' terminus of HC-J6 genome. Solid lines show nucleotide sequences determined by clones from libraries of bacteriophage lambda gt10, and broken lines show nucleotide sequences determined by clones obtained by PCR.

As shown in FIG. 5, the nucleotide sequence of the 3' terminus of HC-J6 genome was determined by analysis of clones obtained by amplification of HCV specific cDNA by PCR.

Nucleotide sequence of HC-J6 from nt8701 to 9241 was determined from consensus sequence of three clones consisting of 938 nucleotides, C9760, C9234 and C9761, obtained by amplification of sample using primer #80 (5'-GACACCCGCTGTTTTGACTC-3') and #60 (5'-GTTCTTACTGCCCAGTTGAA-3').

Nucleotide sequence of 3' terminus down stream from nt9242 was determined in the method described below.

Isolation of RNA from HC-J6 was made in the same manner as described in (1) above. The obtained RNA was added poly (A) to its 3' terminus using poly (A) polymerase and cDNA was synthesized using oligo (dT)$_{20}$ as a primer, and obtained cDNA was provided to PCR as a template.

First PCR product was made with using #97 (5'-AGTCAGGGCGTCCCTCATCT-3') as a sense primer and oligo (dT)$_{20}$ as an antisense primer. Second PCR product was made with using #90 (5'-GCCGTTTGCGGCCGATATCT-3') corresponding to downstream sequence of #97 as a sense primer, and oligo (dT)$_{20}$ as an antisense primer as well as first PCR product. PCR product obtained by two step amplification was smoothened on both ends by treatment with T$_4$DNA polymerase, followed by phosphorylation of 5'terminus by T$_4$polynucleotide kinase. The obtained product was subcloned into Hinc II position of M13mp19 phage vector.

Nucleotide sequence of 3' terminus was determined from consensus sequence of 19 obtained clones, C10311, C10313, C10314, C10320, C10322, C10323, C10326, C10328, C10330, C10333, C10334, C10336, C10337, C10345, C10346, C10347, C10349, C10350 and C10357.

As a result, the nucleotide sequence of cDNA to HC-J6 genome RNA was determined as shown in sequence list 2, and full sequence of genome RNA was determined as shown in sequence list 1.

(8) Determination of amino acid sequences

According to the nucleotide sequence of the genome of strain HC-J6, determination was made of sequence of coded region starting with ATG. As a result, HC-J6 genome was found to have a long *Open Reading Frame* coding for polypeptide precursor consisting of 3033 amino acid residues.

(9) Determination of 5' terminal nucleotide sequence of HC-J8

Figure 6:
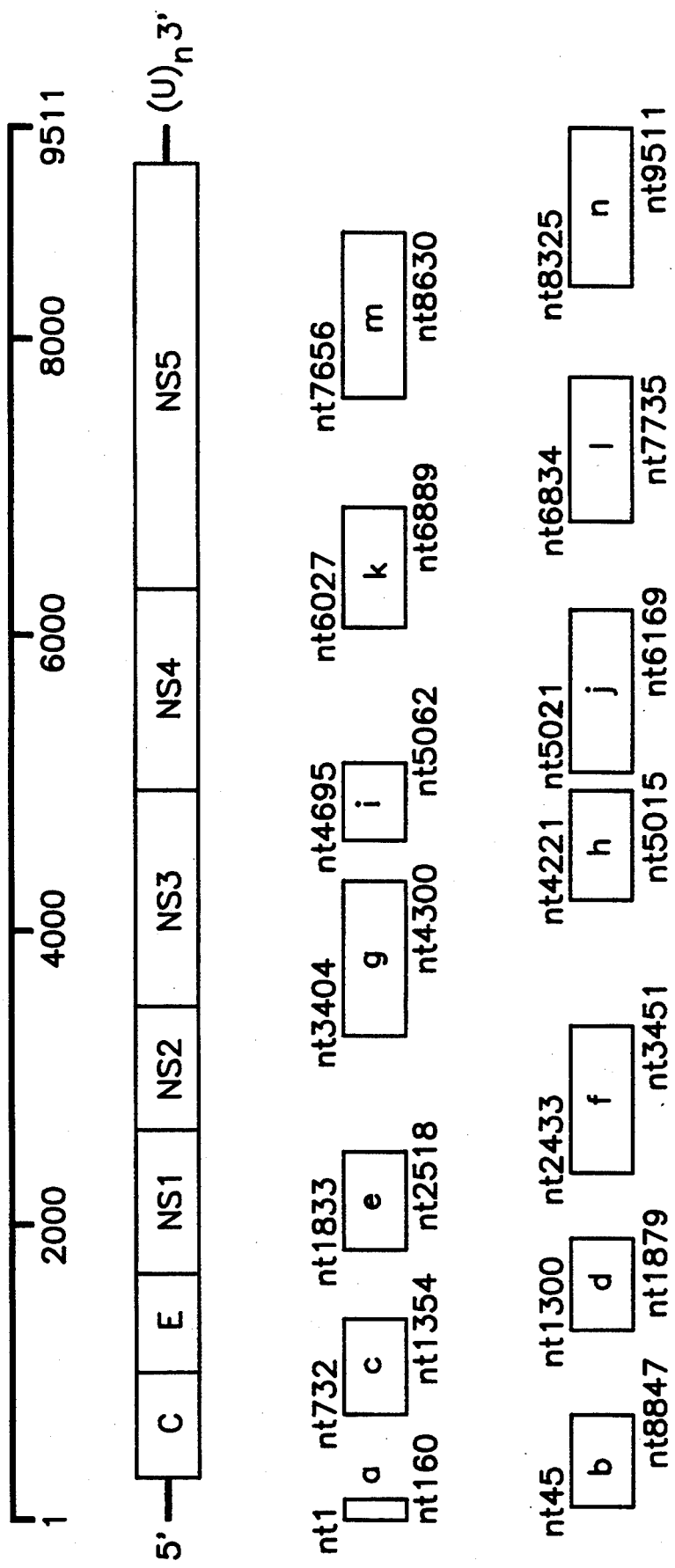
FIG. 6 shows the structure of coding region of NANB hepatitis virus genome (HC-J8) and positions of clones. Regions a to n indicate positions of amplification by PCR.

As shown in FIG. 6, the nucleotide sequence of 5' terminus of HC-J8 genome (a region) was determined by analysis of clones obtained by amplification of HCV specific cDNA by PCR.

Single-stranded cDNA was synthesized using antisense primer #36 (5'-AACACTACTCGGCTAGCAGT-3') of nt246 to 265 in the same manner as (2) above, then it was added with dATP tail at its 3' terminus by terminal deoxynucleotidyl transferase, then amplified by one-sided PCR in two stages.

That is, in the first stage, antisense primer #48 (5'-GTTGATCCAAGAAAGGACCC-3') of nt188 to 207 was used with sense primer selected from non-specific primer #165 (5'AAGGATCCGTCGACATCGATAATACG (A)₁₇-3') and #171 (5'-AAGGATCCGTCGACATCGATAATACG(T)₁₇-3') to amplify the dA-tailed cDNA by PCR for 35 cycles; and in the second stage, using the product of the first-stage PCR as a template, non-specific primer #166 (5' AAGGATCCGTCGACATCGAT -3') and antisense primer #109 (21-mer; 5'-ACCGGATCCGCAGACCACTAT -3') were added to initiate PCR for 30 cycles. The product of PCR was subcloned to M13 phage vector.

Thirteen independent clones (poly dT-tailed: C14951, C14952, C14953, C14958, C14960, C14968, C14971, C14972 and C14974; poly dA-tailed: C14987, C14996, C14999 and C15000) were obtained (each considered having complete length of 5' terminus), and the consensus sequence of nt1–139 of the respective clones was determined.

(10) cDNA amplification of ORF region and 3' terminus by PCR

As shown in FIG. 6, the nucleotide sequence of downstream from nt140 of HC-J8 genome was determined by analysis of clones obtained by amplification of HCV specific cDNA by PCR.

Single-stranded cDNAs to HC-J8 RNA were synthesized in the same manner as (2) above using antisense primers described below, then they were amplified by PCR using sense and antisense primers described below. Each product of PCR was subcloned to M13 phage vector, then consensus sequence of the respective clones of each region was determined.

The primers for cDNA synthesis and PCR amplification, and the numbers of obtained clones are shown below for each region. Alphabetical symbol of each amplified region corresponds to that in FIG. 6.

b region
nt45–847
Primer for cDNA synthesis: #122 (5'-AGGTTCCCTGTTGCATAATT-3')
Primer for PCR: sense: #32A (5'-CTGTGAGGAACTACTGTCTT-3') antisense #122
Clones: C15221, C15222, C15223 c region
nt732–1354
Primmer for cDNA synthesis: #54 (5'-ATCGCGTACGCCAGGATCAT-3')
Primer for PCR: sense: #50 (5'-GCCGATCTCATGGGGTACAT-3') antisense: #54
Clones: C15256, C15257, C15258 d region
nt1300–1879
Primer for cDNA synthesis: #199 (5'-GGGGTGAAACAATACACCGG-3')
Primer for PCR:sense: #205 (5'-GGGACATGATGATCAACTGG-3') antisense: #199
Clones: C14221, C14222, C14223 e region
nt1833–2518
Primer for cDNA synthesis: #146 (5'-AGTAGCATCATCCACAAGCA-3')
Primer for PCR: sense: #150 (5'-ATCGTCTCGGCTAAGACGGT-3') antisense: #146
Clones: Cl1535, Cl1540, Cl1566 f region
nt2433–3451
Primer for cDNA synthesis: #170 (5'-GCATAAGCAGTGATGGGGGC-3')
Primer for PCR: sense: #160 (5'-CAGAACATCGTGGACGTGCA-3') antisense: #170
Clones: C15348, C15349, C15356 g region
nt3404–4300
Primer for cDNA synthesis: #225 (5'-TCGCATATGATGATGTCATA-3')
Primer for PCR: sense: #238 (5'-CTACACCTCCAAGGGGTGGA-3') antisense: #225
Clones: C15701, C15702, C15703 h reqion
nt4221–5015
Primer for cDNA synthesis: #216 (5'-GTGGTCTAGACATACGGGCA-3')
Primer for PCR: sense: #230 (5'-CCCATCACGTACTCCACATA-3') antisense: #216
Clones: C15391, C15392, C15393 i region
nt4695–5062
Primer for cDNA synthesis: #210 (5'-GCATCTATGTGTGTGAGGCC-3')
Primer for PCR: sense: #209 (5'-TTCGACTCCGTGATCGACTG-3') antisense: #210
Clones: C14087, C14088, C14089 j region
nt5021–6169
Primer for cDNA synthesis: #162 (5'-TCCGACTCCGTCACGTAGTG-3')
Primer for PCR: sense:#227 (5'-GTTCTGGGAAGCGGTCTTTA-3') antisense: #162
Clones: C15421, C15422, C15423 k region
nt6027–6889
Primer for cDNA synthesis: #232 (5'-GATGGGTCTGTTAGCATGGA-3')
Primer for PCR: sense: #242 (5'-TTGGTAGTGGGAGTCATCTG-3') antisense: #232
Clones: C15733, C15734, C15735 l region
nt6834–7735
Primer for cDNA synthesis #239 (5'-ATCGGTAACTTCTCCTCTTC-3')
Primer for PCR: sense: #241 (5'-CCTTGCGATCCTGAACCTGA-3') antisense:#239
Clones: C15798, C15799, C15800 m region
nt7656–8630
Primer for cDNA synthesis: #222 (5'-GACCAGGTCGTCTCCACACA-3')
Primer for PCR: sense: #229 (5'-GTCGTGTGCTGCTCCATGTC-3') antisense: #222
Clones: C15376, C15378, C15381 n region
nt8325–9511
Primer for cDNA synthesis: #165
Primer for PCR: sense: #80 (5'-GACACCCGCTGTTTTGACTC-3') non-specific: #165
Clones: C15270, C15271, C15272

From the analysis described above, full nucleotide sequence of cDNA to HC-J8 was determined as shown in sequence list 7, then full nucleotide sequence of HC-J8 genome RNA as shown in sequence list 6. Two amino acid sequences shown in sequence lists 8 and 9 represent those coded for by HC-J8 genome.

Utilizing known immunological techniques, it is possible to determine epitopes (e.g., from the core region, etc.) from the polypeptides of sequence lists 5, 8 and 9. Determination of such epitopes of the NANB hepatitis virus opens access to chemical synthesis of the peptide, manufacturing of the peptide by genetic engineering techniques, synthesis of the polynucleotides, manufacturing of the antibody, manufacturing of NANB hepatitis diagnostic reagents, and development of products such as NANB hepatitis vaccines.

According to the well-known method described by Merrifield, NANB peptides can be synthesized. Furthermore, the polynucleotides in sequence lists 2–4 and 7 can be used to express polypeptides in host cells such as *Escherichia coli* by means of genetic engineering technique.

A detection system for antibody against NANB hepatitis virus can be developed using polyvinyl microtiter plates and the sandwich method. For example, 50 μl of 5 μg/ml concentration of a NANB peptide can be dispensed in each well of the microtiter plates and incubated overnight at room temperature for consolidation. The microplate wells can be washed five times with physiological saline containing 0.05% Tween 20. For overcoating, 100 μl of NaCl buffer containing 30% (v/v) of calf serum and 0.05% Tween 20 (CS buffer) can be dispensed in each well and discarded after incubation for 30 minutes at room temperature.

For determination of NANB antibodies in samples, in the primary reaction, 50 μl of the CS buffer containing 30% calf serum and 10 μl of a sample can be dispensed in each microplate well and incubated on a microplate vibrator for one hour at room temperature. After completion of the reaction, microplate wells can be washed five times in the same way as previously described.

In the secondary reaction, as labeled antibody 1 ng of horseradish peroxidase labeled anti-human IgG mouse monoclonal antibodies (Fab' fragment: 22G, Institute of Immunology Co., Ltd., Tokyo, Japan) dissolved in 50 μl of calf serum can be dispensed in each microplate well, and incubated on a microplate vibrator for one hour at room temperature. Wells can be washed five times in the same way. After addition of hydrogen peroxide (as substrate) and 50 μl of O-phenylendiamine solution (as color developer) in each well, and after incubation for 30 minutes at room temperature, 50 μl of 4M sulphuric acid can be dispensed in each well to stop further color development and for reading absorbance at 492 nm.

The cut-off level of this assay system can be set by measuring a number of donor samples with normal serum ALT (alanine aminotransferase) value of 34 Karmen unit or below and which tested negative for anti-HCV.

The present invention makes possible detection of NANB hepatitis virus infection which could not be detected by conventional determination methods, and provide NANB hepatitis detection kits capable of highly specific and sensitive detection at an early phase of infection.

These features allow accurate diagnosis of patients at an early stage of the disease and also help to remove at higher rate NANB hepatitis virus carrier bloods through screening test of donor bloods.

Polypeptides and their antibodies under this invention can be utilized for manufacture of vaccines and immunological pharmaceuticals, and structural gene of NANB hepatitis virus provides indispensable tools for detection of polypeptide antigens and antibodies.

Antigen-antibody complexes can be detected by methods known in this art. Specific monoclonal and polyclonal antibodies can be obtained by immunizing such animals as mice, guinea pigs, rabbits, goats and horses with NANB peptides (e.g., bearing NANB hepatitis antigenic epitope).

The present invention is based on studies on isolated virus genome of NANB hepatitis virus named HC-J6 and HC-J8, and is completed by clarification of the full sequence of the nucleotides. The invention makes possible highly specific detection of NANB hepatitis virus and provision of polypeptide, polyclonal antibody and monoclonal antibody to prepare the test system.

Further variations and modifications of the invention will become apparent to those skilled in the art from the foregoing and are intended to be encompassed by the claims appended hereto.

Japanese Priority Applications 287402/91 filed Aug. 9, 1991 and 360441/91 filed on Dec. 5, 1991 are relied on and incorporated by reference. U.S. patent applications Ser. Nos. 07/540,604 (filed Jun. 19, 1990), 07/653,090 (filed Feb. 8, 1991), and 07/712,875 (filed Jun. 11, 1991) are incorporated by reference in their entirety.

Sequence list

Sequence list 1: whole nucleotides of HC-J6 genome RNA

Sequence list 2: N-9589 whole nucleotides of cDNA to HC-J6 genome RNA

Sequence list 3: J6-ϕ81 nucleotides of clone J6-ϕ81

Sequence list 4: J6-ϕ8 nucleotides of clone J6-ϕ8

Sequence list 5: P-J6-3033 whole amino acids of ORF of HC-J6 genome

Sequence list 6: whole nucleotides of HC-J8 genome RNA

Sequence list 7: whole nucleotides of cDNA to HC-J8 genome RNA

Sequence list 8: whole amino acids of a variation of ORF of HC-J8 genome

Sequence list 9: whole amino acids of a variation of ORF of HC-J8 genome

What is claimed:

1. Isolated RNA of non-A, non-B hepatitis virus, strain HC-J6, having SEQ ID NO. 1.
2. Recombinant cDNA of non-A, non-B hepatitis virus, strain HC-J6, having SEQ ID NO. 4.